(12) United States Patent
Lee et al.

(10) Patent No.: US 12,126,465 B2
(45) Date of Patent: Oct. 22, 2024

(54) SERVER FOR CONTROLLING HOME NETWORK BASED ON SLEEP STATE AND METHOD FOR OPERATING THE SAME

(71) Applicant: Samsung Electronics Co., Ltd., Suwon-si (KR)

(72) Inventors: Jongkee Lee, Suwon-si (KR); Seongkook Hong, Suwon-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 94 days.

(21) Appl. No.: 18/153,122

(22) Filed: Jan. 11, 2023

(65) Prior Publication Data

US 2023/0254178 A1   Aug. 10, 2023

Related U.S. Application Data

(63) Continuation of application No. PCT/KR2022/021236, filed on Dec. 23, 2022.

(30) Foreign Application Priority Data

Feb. 7, 2022  (KR) .................. 10-2022-0015754
Feb. 24, 2022 (KR) .................. 10-2022-0024557

(51) Int. Cl.
*H04L 12/28* (2006.01)
*G06F 3/01* (2006.01)
*H04L 12/12* (2006.01)

(52) U.S. Cl.
CPC ............ *H04L 12/282* (2013.01); *G06F 3/011* (2013.01); *H04L 12/12* (2013.01)

(58) Field of Classification Search
CPC ....... H04L 12/282; H04L 12/12; H04L 12/28; H04L 67/535; H04L 12/2818;
(Continued)

(56) References Cited

U.S. PATENT DOCUMENTS

| 5,309,145 A * | 5/1994 | Branch ................ G08B 19/005 340/567 |
| 8,423,194 B2 * | 4/2013 | Besore .................... H02J 3/007 307/29 |

(Continued)

FOREIGN PATENT DOCUMENTS

| CN | 111781842 A | 10/2020 |
| CN | 113746708 A | 12/2021 |

(Continued)

OTHER PUBLICATIONS

International Search report dated Mar. 24, 2023, issued in International Patent Application No. PCT/KR2022/021236.

*Primary Examiner* — Curtis J King
(74) *Attorney, Agent, or Firm* — Jefferson IP Law, LLP

(57) ABSTRACT

A server comprising a communication circuit and at least one processor is provided. The at least one processor is configured to identify whether a designated sleep preparation execution condition is met, if the sleep preparation execution condition is met, determine whether sleep states of one or more users corresponding to one or more electronic devices present in a home network are detected, and if the sleep states of the one or more users are detected, transmit a first control command indicating a designated first sleep start operation to a plurality of home devices present in the home network through the communication circuit.

20 Claims, 29 Drawing Sheets

(58) Field of Classification Search
CPC ........... G06F 3/011; G06F 1/16; G16Y 10/80; G16Y 20/40; G16Y 40/30; A61M 16/161; A61M 2021/0022; A61M 2021/0027; A61M 2021/005; A61M 2021/0055; A61M 2205/18; A61M 2205/3306; A61M 2205/3317; A61M 2205/332; A61M 2205/3358; A61M 2205/3368; A61M 2205/8206; A61M 2209/088; A61M 2230/06; A61M 2230/65; A61M 21/02; A61M 2205/3375; A61M 2205/3561; A61M 2205/3592; A61M 2205/505; H04W 4/33; A61B 5/4806
See application file for complete search history.

(56) References Cited

U.S. PATENT DOCUMENTS

| | | | |
|---|---|---|---|
| 10,052,061 | B2 | 8/2018 | Raymann et al. |
| 10,054,329 | B1* | 8/2018 | Hutz ................ G08B 25/002 |
| 10,092,219 | B2 | 10/2018 | Arnold et al. |
| 10,133,443 | B2 | 11/2018 | Von Dehsen et al. |
| 10,510,220 | B1* | 12/2019 | Moore, Jr. ............. G10K 11/00 |
| 10,911,911 | B1* | 2/2021 | Wang ................... H04W 4/029 |
| 11,100,922 | B1* | 8/2021 | Mutagi ................... G06F 3/167 |
| 11,194,297 | B2 | 12/2021 | Xie |
| 11,399,636 | B2* | 8/2022 | Demirli ................. G05B 15/02 |
| 11,688,271 | B2* | 6/2023 | Wright ................. G08B 25/005 |
| | | | 340/506 |
| 11,790,759 | B2* | 10/2023 | Hutz ..................... G08B 25/008 |
| | | | 340/506 |
| 2001/0025349 | A1* | 9/2001 | Sharood ............. G06Q 30/0236 |
| | | | 713/340 |
| 2001/0048030 | A1* | 12/2001 | Sharood ............. H02J 13/00016 |
| | | | 236/49.3 |
| 2002/0000092 | A1* | 1/2002 | Sharood ............. H02J 13/00026 |
| | | | 62/127 |
| 2004/0222879 | A1* | 11/2004 | Sawyer ..................... G08B 6/00 |
| | | | 340/407.1 |
| 2005/0125083 | A1* | 6/2005 | Kiko ..................... H04L 12/282 |
| | | | 700/20 |
| 2005/0216580 | A1* | 9/2005 | Raji ....................... G06Q 30/02 |
| | | | 709/223 |
| 2006/0172782 | A1* | 8/2006 | Planning ............. H01M 10/465 |
| | | | 455/572 |
| 2008/0231468 | A1* | 9/2008 | Myllymaki ......... H04L 12/2816 |
| | | | 340/870.17 |
| 2011/0096637 | A1* | 4/2011 | Chiang ................. G04G 13/026 |
| | | | 368/256 |
| 2011/0313579 | A1* | 12/2011 | Ling ................... H04L 12/2814 |
| | | | 700/291 |
| 2012/0066168 | A1* | 3/2012 | Fadell ................... H05B 47/115 |
| | | | 702/140 |
| 2013/0311807 | A1* | 11/2013 | Woo ...................... G06F 1/3234 |
| | | | 713/323 |
| 2014/0142773 | A1* | 5/2014 | Ling .................... G05B 13/02 |
| | | | 700/291 |
| 2014/0248802 | A1* | 9/2014 | Hieda ................. H04L 12/2825 |
| | | | 439/620.01 |
| 2014/0282967 | A1* | 9/2014 | Maguire ............... H04L 67/125 |
| | | | 726/7 |
| 2015/0026647 | A1 | 1/2015 | Park et al. |
| 2015/0032505 | A1* | 1/2015 | Kusukame ......... G06Q 30/0269 |
| | | | 705/7.31 |
| 2015/0194040 | A1* | 7/2015 | Fiedler ................... H04W 4/70 |
| | | | 340/870.09 |
| 2015/0256399 | A1* | 9/2015 | Kim .................... H04L 41/0226 |
| | | | 370/254 |
| 2015/0276254 | A1* | 10/2015 | Nemcek .................. G10L 15/22 |
| | | | 700/278 |
| 2015/0334440 | A1* | 11/2015 | Lee .................. H04N 21/47217 |
| | | | 725/133 |
| 2015/0348554 | A1* | 12/2015 | Orr ........................ G05B 15/02 |
| 2016/0091879 | A1* | 3/2016 | Marti .................. H04L 12/2816 |
| | | | 700/275 |
| 2016/0113595 | A1* | 4/2016 | Bingley ................. G16H 20/17 |
| | | | 340/286.07 |
| 2016/0136385 | A1* | 5/2016 | Scorcioni ............. A61B 5/4812 |
| | | | 600/26 |
| 2016/0334772 | A1* | 11/2016 | Nguyen .............. H04L 12/2818 |
| 2016/0344815 | A1* | 11/2016 | Hyun .................. H04L 12/2803 |
| 2017/0143252 | A1 | 5/2017 | Zou et al. |
| 2017/0160703 | A1* | 6/2017 | Heo ....................... G08B 21/22 |
| 2017/0214540 | A1* | 7/2017 | Wang .................. H04L 12/2827 |
| 2018/0091326 | A1* | 3/2018 | McLaughlin ....... H04L 41/0893 |
| 2018/0139069 | A1* | 5/2018 | Rawlins ................. G06F 3/04886 |
| 2018/0210437 | A1* | 7/2018 | Ashar ..................... G08B 21/04 |
| 2018/0262362 | A1* | 9/2018 | Goldstein ........... H04L 12/2832 |
| 2018/0323991 | A1* | 11/2018 | Segal ..................... G10L 15/26 |
| 2018/0367330 | A1* | 12/2018 | Kang .................... H04L 65/40 |
| 2019/0045046 | A1 | 2/2019 | Ma |
| 2019/0074988 | A1* | 3/2019 | Lee ..................... A61B 5/0002 |
| 2019/0081810 | A1* | 3/2019 | Jung ........................ G06F 3/167 |
| 2019/0087076 | A1* | 3/2019 | Dey ....................... H04N 23/63 |
| 2019/0150251 | A1* | 5/2019 | Yang ..................... H05B 45/12 |
| | | | 315/152 |
| 2019/0206416 | A1* | 7/2019 | Demirli ................. H04R 3/002 |
| 2020/0014552 | A1* | 1/2020 | Tan .................... H04L 12/2809 |
| 2020/0178892 | A1* | 6/2020 | Maslik ................. A61B 5/4836 |
| 2020/0258503 | A1* | 8/2020 | Maeda .................... G10L 15/22 |
| 2020/0357263 | A1* | 11/2020 | Peterson .............. G04G 21/08 |
| 2020/0382335 | A1* | 12/2020 | Trim ..................... G06N 20/00 |
| 2021/0144024 | A1* | 5/2021 | Wang ..................... H04L 67/34 |
| 2021/0190351 | A1* | 6/2021 | Hilbig .................... A61B 5/746 |
| 2021/0191345 | A1* | 6/2021 | Pabla .................. H04L 12/2829 |
| 2021/0194717 | A1* | 6/2021 | Yoon .................. H04L 12/2816 |
| 2021/0282248 | A1* | 9/2021 | Magielse ............. H05B 47/175 |
| 2021/0349617 | A1 | 11/2021 | Crowley et al. |
| 2022/0051553 | A1* | 2/2022 | Reimer ................ G08B 29/181 |
| 2022/0208319 | A1* | 6/2022 | Ansari ................... G16H 10/60 |
| 2022/0317641 | A1* | 10/2022 | Wang ..................... H04L 12/282 |
| 2023/0006855 | A1* | 1/2023 | Robertsson .............. G06T 7/55 |
| 2023/0107712 | A1* | 4/2023 | Gil ........................ G16H 20/70 |
| | | | 700/28 |
| 2023/0127500 | A1* | 4/2023 | Burks ................. H04L 12/2818 |
| | | | 700/19 |
| 2023/0132171 | A1* | 4/2023 | Jedwab ............. G08B 13/19608 |
| | | | 340/541 |
| 2023/0216702 | A1* | 7/2023 | Shen .................... H04L 67/1051 |
| | | | 709/224 |
| 2024/0048401 | A1* | 2/2024 | Takei ..................... H04L 12/282 |
| 2024/0173499 | A1* | 5/2024 | Shouldice ............. A61M 16/024 |

FOREIGN PATENT DOCUMENTS

| | | |
|---|---|---|
| JP | 2020-116304 A2 | 8/2020 |
| KR | 10-2011-0032605 A | 3/2011 |
| KR | 10-2015-0125214 A | 11/2015 |
| KR | 10-2016-0018146 | 2/2016 |
| KR | 10-2017-0057038 A | 5/2017 |
| KR | 10-2017-0073548 | 6/2017 |
| KR | 10-2017-0124423 A | 11/2017 |
| KR | 10-2018-0083188 | 7/2018 |
| KR | 10-2019-0047697 | 5/2019 |
| KR | 10-2020-0044432 | 4/2020 |
| KR | 10-2135351 B1 | 7/2020 |
| KR | 10-2021-0137878 A | 11/2021 |

* cited by examiner

SERVER FOR CONTROLLING HOME NETWORK BASED ON SLEEP STATE AND METHOD FOR OPERATING THE SAME

CROSS-REFERENCE TO RELATED APPLICATION(S)

This application is a continuation application, claiming priority under § 365(c), of an International application No. PCT/KR2022/021236, filed on Dec. 23, 2022, which is based on and claims the benefit of a Korean patent application number 10-2022-0015754, filed on Feb. 7, 2022, in the Korean Intellectual Property Office, and of a Korean patent application number 10-2022-0024557, filed on Feb. 24, 2022, in the Korean Intellectual Property Office, the disclosure of each of which is incorporated by reference herein in its entirety.

TECHNICAL FIELD

The disclosure relates to a server for controlling a home network based on sleep states of users and a method for operating the same.

BACKGROUND ART

More and more services and additional functions are being provided through user terminals, e.g., smartphones, or other portable electronic devices. To meet the needs of various users and raise use efficiency of electronic devices, communication service carriers or device manufacturers are jumping into competitions to develop electronic devices with differentiated and diversified functionalities. Accordingly, various functions that are provided through electronic devices are evolving more and more.

As wireless communication technology develops, devices using artificial intelligence (AI) have been widely introduced. For example, home appliances connected over a network through Internet of things (IoT) technology utilize artificial intelligence. The IoT environment may provide intelligent Internet technology services that create new values in human life by collecting and analyzing data generated by devices. Through the convergence and combination of existing Internet technologies and various industries, IoT may be applied to fields, such as smart homes, smart buildings, smart cities, smart cars, and smart home appliances.

Meanwhile, the home is equipped with various home appliances for user convenience. Various services have been proposed to make manipulation or control of home appliances more convenient by way of IoT technology. The home network technology may provide various services through the home network to users in the home. For example, the user may control various electronic devices constituting a home network (e.g., home devices, such as home appliances to which IoT technology is applied) using a personal electronic device (e.g., a smart phone). Users of the home network may wish to receive more diverse services through the home network. Accordingly, the development of a technology for controlling the home devices constituting the home network by reflecting the user's intention has been requested.

The above information is presented as background information only to assist with an understanding of the disclosure. No determination has been made, and no assertion is made, as to whether any of the above might be applicable as prior art with regard to the disclosure.

DISCLOSURE

Means to Address the Problems

Aspects of the disclosure are to address at least the above-mentioned problems and/or disadvantages and to provide at least the advantages described below. Accordingly, an aspect of the disclosure is to provide a server for controlling home network based on sleep state and method for operating the same.

Additional aspects will be set forth in part in the description which follows and, in part, will be apparent from the description, or may be learned by practice of the presented embodiments.

In accordance with an aspect of the disclosure, a server is provided. The server includes a communication circuit and at least one processor. The at least one processor may be configured to identify whether a designated sleep preparation execution condition is met. The at least one processor may be configured to, in response to the sleep preparation execution condition being met, determine whether sleep states of one or more users corresponding to one or more electronic devices present in the home network are detected. The at least one processor may be configured to, in response to the sleep states of the one or more users being detected, transmit a first control command indicating a designated first sleep start operation to a plurality of home devices present in the home network through the communication circuit.

In accordance with another aspect of the disclosure, a method for operating a server is provided. The method may comprise identifying whether a designated sleep preparation execution condition is met. The method may comprise, if the sleep preparation execution condition is met, determining whether sleep states of one or more users corresponding to one or more electronic devices present in a home network are detected. The method may comprise, in response to the sleep states of the one or more users being detected, transmitting a first control command indicating a designated first sleep start operation to a plurality of home devices present in the home network through the communication circuit.

In accordance with another aspect of the disclosure, a non-transitory computer readable storage medium storing one or more programs, the one or more programs comprising instructions configured to, when executed by at least one processor of an electronic device, cause the electronic device to: identify whether a sleep preparation execution condition is met, if the sleep preparation execution condition is met, determine whether sleep states of one or more users corresponding to one or more electronic devices present in a home network are detected, and if the sleep states of the one or more users are detected, transmit a first control command indicating a designated first sleep start operation to a plurality of home devices present in the home network.

Other aspects, advantages, and salient features of the disclosure will become apparent to those skilled in the art from the following detailed description, which, taken in conjunction with the annexed drawings, discloses various embodiments of the disclosure.

DESCRIPTION OF THE DRAWINGS

The above and other aspects, features, and advantages of certain embodiments of the disclosure will be more apparent from the following description taken in conjunction with the accompanying drawings, in which.

Throughout the drawings, like reference numerals will be understood to refer to like parts, components, and structures.

MODE FOR INVENTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and construction may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
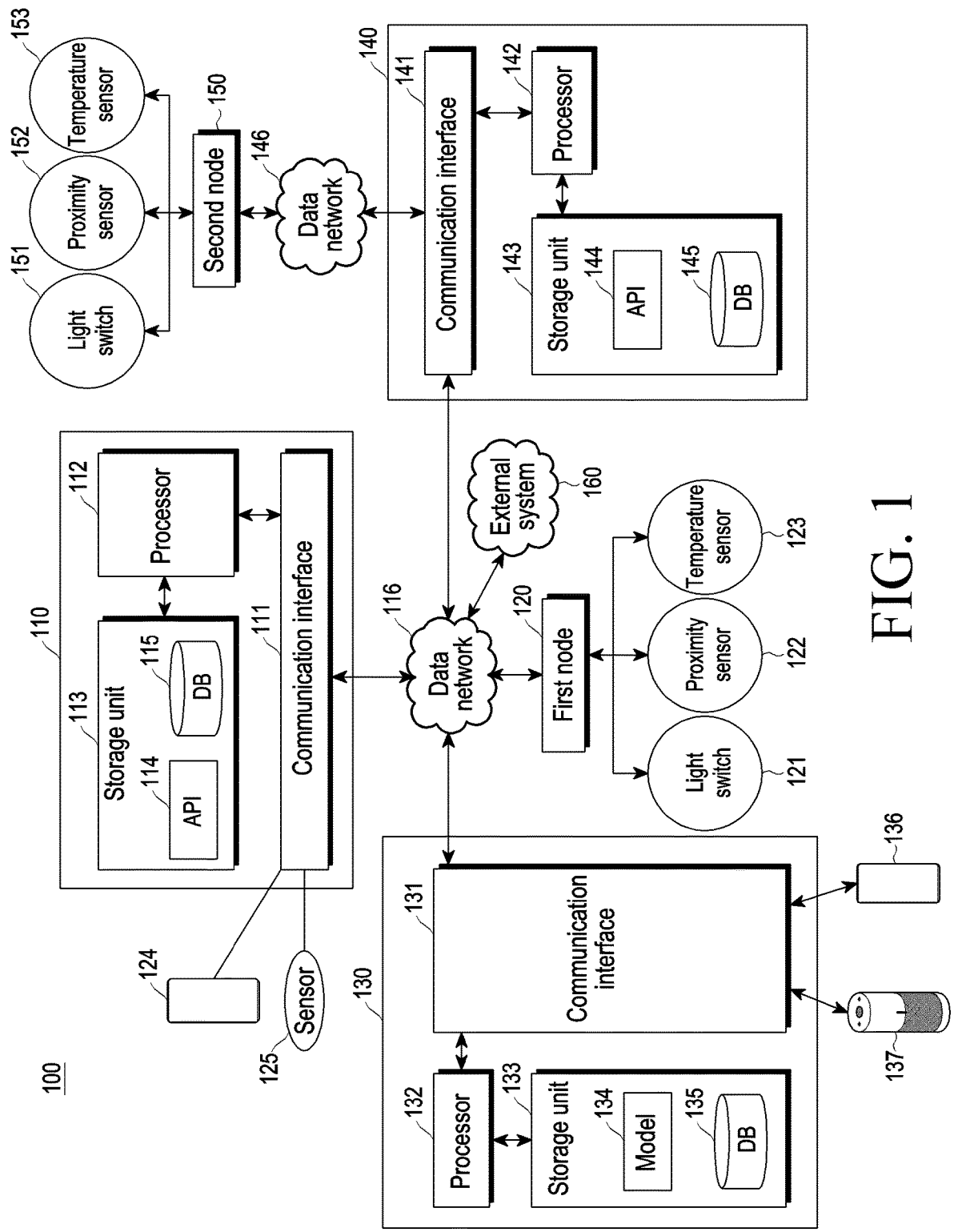
FIG. 1 illustrates an internet-of-things (IoT) system according to an embodiment of the disclosure.

FIG. 1 illustrates an internet-of-things (IoT) system according to an embodiment of the disclosure. At least some of the components shown in FIG. 1 may be omitted, or at least one component not shown may be added.

Referring to FIG. 1, according to an embodiment of the disclosure, the IoT system 100 includes a plurality of electronic devices connectable to a data network 116 or 146. For example, the IoT system 100 may include at least one of a first IoT server 110, a first node 120, a voice assistance server 130, a second IoT server 140, a second node 150, or devices 121, 122, 123, 124, 125, 136, 137, 151, 152, and 153.

According to an embodiment of the disclosure, the first IoT server 110 may include at least one of a communication interface 111, a processor 112, or a storage unit 113. The second IoT server 140 may include at least one of a communication interface 141, a processor 142, or a storage unit 143. In the disclosure, the "IoT server" may remotely control and/or monitor one or more devices (e.g., the devices 121, 122, 123, 124, 125, 136, 137, 151, 152, and 153) directly without a relay device, or via a relay device (e.g., the first node 120 or the second node 150), based on, e.g., a data network (e.g., the data network 116 or data network 146). Here, "device" refers to, e.g., a sensor, home appliance, office electronic device, or processing device placed (or positioned) in a local environment, such as a home, office, factory, building, external place, or other types of sites, and is not limited to a specific type. A device that receives a control command and performs an operation corresponding to the control command may be referred to as a "target device." The IoT server may be referred to as a central server in light that it selects a target device from among a plurality of devices and provides control commands.

According to an embodiment of the disclosure, the first IoT server 110 may communicate with devices 121, 122, and 123 via the data network 116. The data network 116 may mean a network for remote communication, such as, e.g., the Internet or a computer network (e.g., a local area network (LAN) or wide area network (WAN)), or may encompass cellular networks.

According to an embodiment of the disclosure, the first IoT server 110 may connect to the data network 116 via the communication interface 111. The communication interface 111 may include a communication device (or communication module) for supporting communication of the data network 116 and may be implemented as a single integrated component (e.g., a single chip) or as a plurality of separate components (e.g., multiple chips). The first IoT server 110 may communicate with the devices 121, 122, and 123 via the first node 120. The first node 120 may receive data from the first IoT server 110 via the data network 116 and transmit the received data to at least some of the devices 121, 122, and 123. The first node 120 may receive data from at least some of the devices 121, 122, and 123 and transmit the received data to the first IoT server 110 via the data network 116. The first node 120 may function as a bridge between the data network 116 and the devices 121, 122, and 123. Although FIG. 1 illustrates only one first node 120, this is merely an example, and embodiments of the disclosure are not limited thereto.

In the disclosure, "node" may refer to an edge computing system or a hub device. According to an embodiment of the disclosure, the first node 120 may support wired and/or wireless communication of the data network 116 and may support wired and/or wireless communication with the devices 121, 122, and 123. For example, the first node 120 may connect to the devices 121, 122, and 123 via a short-range communication network, e.g., at least one of Bluetooth, wireless fidelity (Wi-Fi), Wi-Fi direct, Z-wave, Zigbee, INSETEON, X10, or infrared data association (IrDA), but the type of communication is not limited to a specific one. The first node 120 may be placed (or positioned) in an environment, such as, e.g., a home, office, factory, building, external place, or other types of sites. Thus, the devices 121, 122, and 123 may be monitored and/or controlled by a service provided by the first IoT server 110, and the devices 121, 122, and 123 may not be required to have the capability of full network communication (e.g., Internet communication) for direct connection to the first IoT server 110. Although in the illustrated example, the devices 121, 122, and 123 are implemented as electronic devices in a home environment, such as, e.g., a lamp switch, proximity sensor, and temperature sensor, this is merely an example, and the devices 121, 122, and 123 are not limited thereto.

According to an embodiment of the disclosure, the first IoT server 110 may also support direct communication with devices 124 and 125. Here, "direct communication" may mean communication that does not rely on a relay device, such as the first node 120. For example, "direct communication" may mean communication via, e.g., a cellular communication network and/or data network.

According to an embodiment of the disclosure, the first IoT server 110 may transmit control commands to at least some of devices 121, 122, 123, 124, and 125. Here, "control command" may mean data to trigger a controllable device to perform a specific operation. The specific operation may be an operation performed by a device, including outputting, sensing, reporting, or managing (e.g., deleting or creating) information, but not limited thereto. For example, the processor 112 may obtain information (or a request) for creating a control command from an outside (e.g., at least some of the voice assistance server 130, a second IoT server 140, an external system 160, or devices 121, 122, 123, 124, and 125) and create a control command based on the obtained information. Alternatively, the processor 112 may create a control command based on a designated condition being met by a result of monitoring of at least some of the devices 121, 122, 123, 124, and 125. The processor 112 may control the communication interface 111 to transmit the control command to the target device.

According to an embodiment of the disclosure, the processor 112, processor 132, or processor 142 may be implemented as a combination of one or more of general-purpose processors, such as central processing units (CPUs), digital signal processors (DSPs), application processors (APs), communication processors (CPs), graphics dedicated processors, such as graphical processing units (GPUs) or vision processing units (VPUs), or artificial intelligence dedicated processors, such as neural processing units (NPUs). The above-described processing units are merely examples. It will be easily appreciated by one of ordinary skill in the art that the processor 112 is not limited thereto as long as it is a computational means capable of executing instructions stored in the memory 113 and outputting the results of execution.

According to an embodiment of the disclosure, the processor 112 may configure a web-based interface based on an application programming interface (API) 114 or may expose the resource managed by the first IoT server 110 to the outside. For example, the web-based interface may support communication between the first IoT server 110 and an external web service. For example, the processor 112 may allow the external system 160 to control and/or access the devices 121, 122, and 123. For example, the external system 160 may be an independent (or standalone) system that is not associated with the system 100 or is not part of the system 100. The external system 160 may be, e.g., an external server or website. However, access, by the external system 160, to the devices 121, 122, and 123 or the resource of the first IoT server 110 needs to be secured. According to an embodiment of the disclosure, for automated applications, the processor 112 may expose the API (114)-based API end point (e.g., universal resource locator (URL)) to the outside. As set forth above, the first IoT server 110 may transfer the control command to the target device among the devices 121, 122, and 123. The description of the communication interface 141, the processor 142, the API 144 of the storage unit 143, and the database 145 of the second IoT server 140 may be substantially the same as the description of the communication interface 111, processor 112, the API 114 of the storage unit 113, and a database 115 of the first IoT server 110. The description of the second node 150 may be substantially the same as the description of the first node 120. The second IoT server 140 may transfer the control command to the target device among the devices 151, 152, and 153. The first IoT server 110 and the second IoT server 140 may be operated by the same service provider in an embodiment but, in another embodiment of the disclosure, the servers 110 and 140, respectively, may be operated by different service providers.

According to an embodiment of the disclosure, the voice assistance server 130 may transmit and receive data to/from the first IoT server 110 via the data network 116. According to an embodiment of the disclosure, the voice assistance server 130 may include at least one of a communication interface 131, a processor 132, or a storage unit 133. The communication interface 131 may communicate with a smartphone 136 or AI speaker 137 via a data network (not shown) and/or cellular network (not shown). The smartphone 136 or AI speaker 137 may include a microphone and may obtain a user voice, convert the user voice into a voice signal, and transmit the voice signal to the voice assistance server 130. The processor 132 may receive the voice signal from the smartphone 136 or AI speaker 137 via the communication interface 131. The processor 132 may process the received voice signal based on a stored model 134. The processor 132 may create (or identify) a control command using a processing result, based on information stored in a database 135. According to an embodiment of the disclosure, the storage unit 113, 133, or 143 may include, but is not limited to, at least one non-transitory type of storage medium of flash memory types, hard disk types, multimedia card micro types, card-type memories (e.g., secure digital (SD) or extreme digital (XD) memory cards), random access memories (RAMs), static random access memories (SRAMs), read-only memories (ROMs), electrically erasable programmable read-only memories (EEPROMs), programmable read-only memories (PROMs), magnetic memories, magnetic disks, or optical discs.

In an embodiment of the disclosure, at least one device (e.g., the device 124) communicating with the first IoT server 110 may be a smartphone (e.g., the electronic device 201 of FIG. 2) in a network environment.

Figure 2:
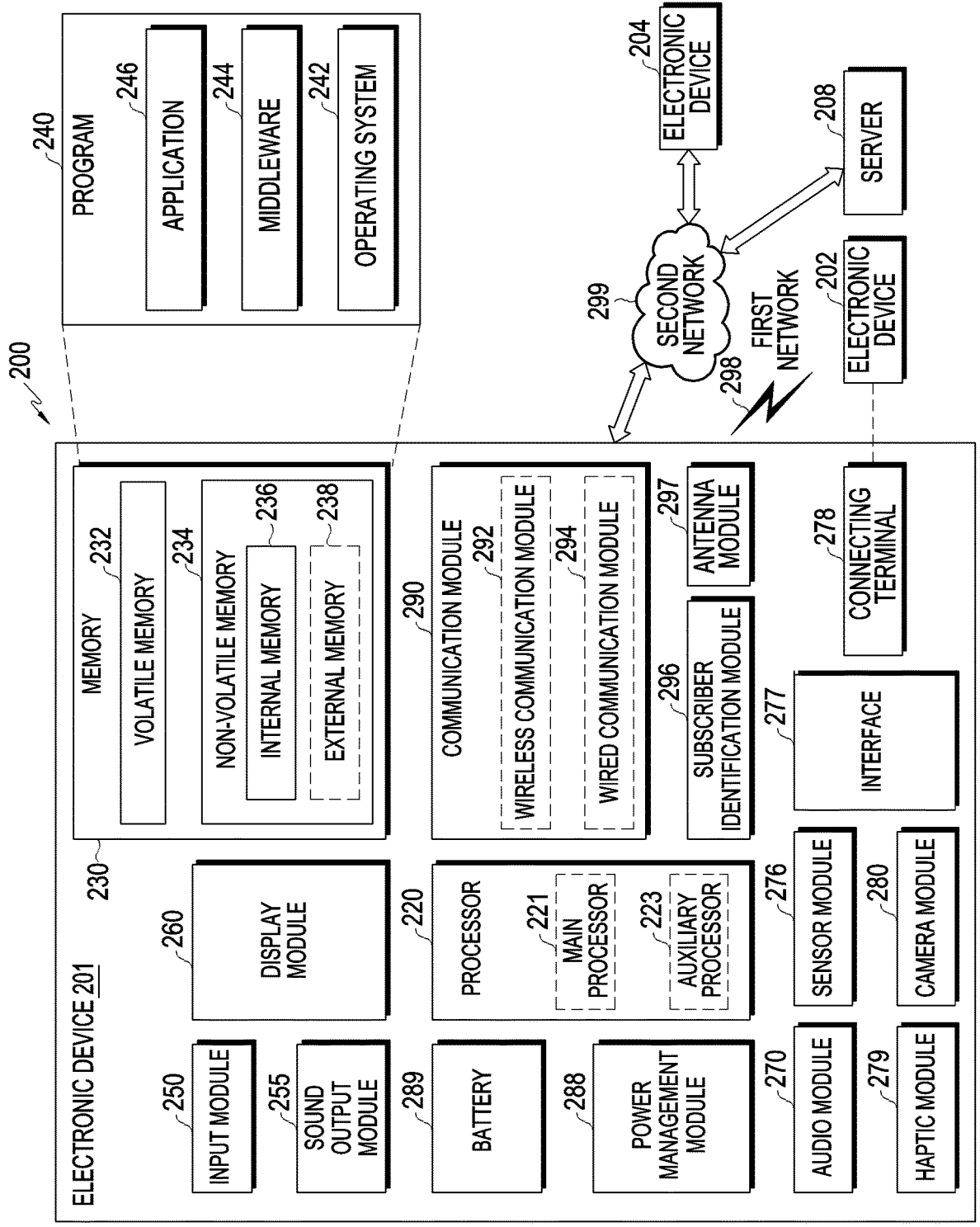
FIG. 2 is a block diagram illustrating an electronic device 201 in a network environment according to an embodiment of the disclosure.

FIG. 2 is a block diagram illustrating an electronic device 201 in a network environment 200 according to an embodiment of the disclosure.

Referring to FIG. 2, the electronic device 201 in the network environment 200 may communicate with at least one of an external electronic device 202 via a first network 298 (e.g., a short-range wireless communication network), or an external electronic device 204 or a server 208 via a second network 299 (e.g., a long-range wireless communication network). According to an embodiment of the disclosure, the electronic device 201 may communicate with the external electronic device 204 via the server 208. According to an embodiment of the disclosure, the electronic device 201 may include a processor 220, a memory 230, an input module 250, a sound output module 255, a display module 260, an audio module 270, a sensor module 276, an interface 277, a connecting terminal 278, a haptic module 279, a camera module 280, a power management module 288, a battery 289, a communication module 290, a subscriber identification module (SIM) 296, or an antenna module 297. In some embodiments of the disclosure, at least one (e.g., the connecting terminal 278) of the components may be omitted from the electronic device 201, or one or more other components may be added in the electronic device 101. According to an embodiment of the disclosure, some (e.g., the sensor module 276, the camera module 280, or the antenna module 297) of the components may be integrated into a single component (e.g., the display module 260).

The processor 220 may execute, for example, software (e.g., a program 240) to control at least one other component (e.g., a hardware or software component) of the electronic device 201 coupled with the processor 220, and may perform various data processing or computation. According to one embodiment of the disclosure, as at least part of the data processing or computation, the processor 220 may store a command or data received from another component (e.g., the sensor module 276 or the communication module 290) in a volatile memory 232, process the command or the data stored in the volatile memory 232, and store resulting data in a non-volatile memory 234. According to an embodiment of the disclosure, the processor 220 may include a main processor 221 (e.g., a central processing unit (CPU) or an application processor (AP)), or an auxiliary processor 223 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 201 includes the main processor 221 and the auxiliary processor 223, the auxiliary processor 223 may be configured to use lower power than the main processor 221 or to be specified for a designated function. The auxiliary processor 223 may be implemented as separate from, or as part of the main processor 221.

The auxiliary processor 223 may control at least some of functions or states related to at least one component (e.g., the display module 260, the sensor module 276, or the communication module 290) among the components of the electronic device 201, instead of the main processor 221 while the main processor 221 is in an inactive (e.g., sleep) state, or together with the main processor 221 while the main processor 221 is in an active state (e.g., executing an application). According to an embodiment of the disclosure, the auxiliary processor 223 (e.g., an image signal processor or a communication processor) may be implemented as part of another component (e.g., the camera module 280 or the communication module 290) functionally related to the auxiliary processor 123. According to an embodiment of the disclosure, the auxiliary processor 223 (e.g., the neural processing unit) may include a hardware structure specified for artificial intelligence model processing. The artificial intelligence model may be generated via machine learning. Such learning may be performed, e.g., by the electronic device 201 where the artificial intelligence is performed or via a separate server (e.g., the server 208). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 230 may store various data used by at least one component (e.g., the processor 220 or the sensor module 276) of the electronic device 201. The various data may include, for example, software (e.g., the program 240) and input data or output data for a command related thereto. The memory 230 may include the volatile memory 232 or the non-volatile memory 234.

The program 240 may be stored in the memory 230 as software, and may include, for example, an operating system (OS) 242, middleware 244, or an application 246.

The input module 250 may receive a command or data to be used by other component (e.g., the processor 220) of the electronic device 201, from the outside (e.g., a user) of the electronic device 201. The input module 250 may include, for example, a microphone, a mouse, a keyboard, keys (e.g., buttons), or a digital pen (e.g., a stylus pen).

The sound output module 255 may output sound signals to the outside of the electronic device 201. The sound output module 255 may include, for example, a speaker or a receiver. The speaker may be used for general purposes, such as playing multimedia or playing record. The receiver may be used for receiving incoming calls. According to an embodiment of the disclosure, the receiver may be implemented as separate from, or as part of the speaker.

The display module 260 may visually provide information to the outside (e.g., a user) of the electronic device 201. The display 260 may include, for example, a display, a hologram device, or a projector and control circuitry to control a corresponding one of the display, hologram device, and projector. According to an embodiment of the disclosure, the display 260 may include a touch sensor configured to detect a touch, or a pressure sensor configured to measure the intensity of a force generated by the touch.

The audio module 270 may convert a sound into an electrical signal and vice versa. According to an embodiment of the disclosure, the audio module 270 may obtain the sound via the input module 250, or output the sound via the sound output module 255 or a headphone of an external electronic device (e.g., an external electronic device 202) directly (e.g., wiredly) or wirelessly coupled with the electronic device 201.

The sensor module 276 may detect an operational state (e.g., power or temperature) of the electronic device 201 or an environmental state (e.g., a state of a user) external to the electronic device 101, and then generate an electrical signal or data value corresponding to the detected state. According to an embodiment of the disclosure, the sensor module 276 may include, for example, a gesture sensor, a gyro sensor, an atmospheric pressure sensor, a magnetic sensor, an accelerometer, a grip sensor, a proximity sensor, a color sensor, an infrared (IR) sensor, a biometric sensor, a temperature sensor, a humidity sensor, or an illuminance sensor.

The interface 277 may support one or more specified protocols to be used for the electronic device 201 to be coupled with the external electronic device (e.g., the external electronic device 202) directly (e.g., wiredly) or wirelessly. According to an embodiment of the disclosure, the interface 277 may include, for example, a high definition multimedia interface (HDMI), a universal serial bus (USB) interface, a secure digital (SD) card interface, or an audio interface.

A connecting terminal 278 may include a connector via which the electronic device 201 may be physically connected with the external electronic device (e.g., the external electronic device 202). According to an embodiment of the disclosure, the connecting terminal 278 may include, for example, a HDMI connector, a USB connector, a SD card connector, or an audio connector (e.g., a headphone connector).

The haptic module 279 may convert an electrical signal into a mechanical stimulus (e.g., a vibration or motion) or electrical stimulus which may be recognized by a user via his tactile sensation or kinesthetic sensation. According to an embodiment of the disclosure, the haptic module 279 may include, for example, a motor, a piezoelectric element, or an electric stimulator.

The camera module 280 may capture a still image or moving images. According to an embodiment of the disclosure, the camera module 280 may include one or more lenses, image sensors, image signal processors, or flashes.

The power management module 288 may manage power supplied to the electronic device 201. According to one embodiment of the disclosure, the power management module 288 may be implemented as at least part of, for example, a power management integrated circuit (PMIC).

The battery 289 may supply power to at least one component of the electronic device 201. According to an embodiment of the disclosure, the battery 289 may include, for example, a primary cell which is not rechargeable, a secondary cell which is rechargeable, or a fuel cell.

The communication module 290 may support establishing a direct (e.g., wired) communication channel or a wireless communication channel between the electronic device 201 and the external electronic device (e.g., the external electronic device 202, the external electronic device 204, or the server 208) and performing communication via the established communication channel. The communication module 290 may include one or more communication processors that are operable independently from the processor 220 (e.g., the application processor (AP)) and supports a direct (e.g., wired) communication or a wireless communication. According to an embodiment of the disclosure, the communication module 290 may include a wireless communication module 292 (e.g., a cellular communication module, a short-range wireless communication module, or a global navigation satellite system (GNSS) communication module) or a wired communication module 294 (e.g., a local area network (LAN) communication module or a power line communication (PLC) module). A corresponding one of these communication modules may communicate with the external electronic device 204 via a first network 298 (e.g., a short-range communication network, such as Bluetooth™, wireless-fidelity (Wi-Fi) direct, or infrared data association (IrDA)) or a second network 299 (e.g., a long-range communication network, such as a legacy cellular network, a 5th generation (5G) network, a next-generation communication network, the Internet, or a computer network (e.g., local area network (LAN) or wide area network (WAN)). These various types of communication modules may be implemented as a single component (e.g., a single chip), or may be implemented as multi components (e.g., multi chips) separate from each other. The wireless communication module 292 may identify or authenticate the electronic device 201 in a communication network, such as the first network 298 or the second network 299, using subscriber information (e.g., international mobile subscriber identity (IMSI)) stored in the subscriber identification module 296.

The wireless communication module 292 may support a 5G network, after a 4th generation (4G) network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 292 may support a high-frequency band (e.g., the millimeter wave (mmWave) band) to achieve, e.g., a high data transmission rate. The wireless communication module 292 may support various technologies for securing performance on a high-frequency band, such as, e.g., beamforming, massive multiple-input and multiple-output (massive MIMO), full dimensional MIMO (FD-MIMO), array antenna, analog beam-forming, or large-scale antenna. The wireless communication module 292 may support various requirements specified in the electronic device 201, an external electronic device (e.g., the external electronic device 204), or a network system (e.g., the second network 299). According to an embodiment of the disclosure, the wireless communication module 292 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 297 may transmit or receive a signal or power to or from the outside (e.g., the external electronic device). According to an embodiment of the disclosure, the antenna module 297 may include one antenna including a radiator formed of a conductor or conductive pattern formed on a substrate (e.g., a printed circuit board (PCB)). According to an embodiment of the disclosure, the antenna module 297 may include a plurality of antennas (e.g., an antenna array). In this case, at least one antenna appropriate for a communication scheme used in a communication network, such as the first network 298 or the second network 299, may be selected from the plurality of antennas by, e.g., the communication module 290. The signal or the power may then be transmitted or received between the communication module 290 and the external electronic device via the selected at least one antenna. According to an embodiment of the disclosure, other parts (e.g., radio frequency integrated circuit (RFIC)) than the radiator may be further formed as part of the antenna module 297.

According to various embodiments of the disclosure, the antenna module 297 may form a mmWave antenna module. According to an embodiment of the disclosure, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment of the disclosure, commands or data may be transmitted or received between the electronic device 201 and the external electronic device 204 via the server 208 coupled with the second network 299. The external electronic devices 202 or 204 each may be a device of the same or a different type from the electronic device 201. According to an embodiment of the disclosure, all or some of operations to be executed at the electronic device 201 may be executed at one or more of the external electronic devices 202, 204, or 208. For example, if the electronic device 201 should perform a function or a service automatically, or in response to a request from a user or another device, the electronic device 201, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 201. The electronic device 201 may provide the outcome, with or without further processing of the outcome, as at least part of a reply to the request. To that end, a cloud computing, distributed computing, mobile edge computing (MEC), or client-server computing technology may be used, for example. The electronic device 201 may provide ultra low-latency services using, e.g., distributed computing or mobile edge computing. In another embodiment of the disclosure, the external electronic device 204 may include an Internet-of-things (IoT) device. The server 208 may be an intelligent server using machine learning and/or a neural network. According to an embodiment of the disclosure, the external electronic device 204 or the server 208 may be included in the second network 299. The electronic device 201 may be applied to intelligent services (e.g., smart home, smart city, smart car, or healthcare) based on 5G communication technology or IoT-related technology.

In an embodiment of the disclosure, the server (e.g., the first IoT server 110 or the second IoT server 140) that controls the home network may control home devices based on the states of one or more users present in the home network (e.g., go out, sleep, or wakeup). The users may be individually in a go out state or in a sleep state. The server needs to control the home devices according to the state of each user.

In an embodiment of the disclosure, the server may control the home devices to operate in a sleep mode in response to a specific condition being met, e.g., according to a designated bedtime. In the sleep mode, the server may control the home devices to provide a comfortable environment for users to sleep. However, users may not fall asleep exactly at bedtime, and some users may be asleep while others may be awake. Since the server cannot know when the users actually fall asleep, the sleep mode after falling asleep should be set manually. Accordingly, there is a need for techniques for individually detecting the sleep states of one or more users in a home network and automatically controlling home devices based on the detection of the sleep state.

Embodiments of the disclosure may use smart home network technology to control home devices to configure a good sleep environment in response to a specific condition being met.

Embodiments of the disclosure may control home devices in a home network to enhance the sleep environment of users.

According to embodiments of the disclosure, there may be provided a server for controlling a home network based on sleep states of users and an operation method thereof.

Embodiments of the disclosure may utilize the sleep states of a plurality of users to control home devices positioned around each user.

In an embodiment of the disclosure, the IoT system 100 may further include a wearable device (e.g., the wearable device 302 of FIG. 3) that may communicate with the first IoT server 110 directly or via another device (e.g., the device 124 or the first node 120).

Figure 3:
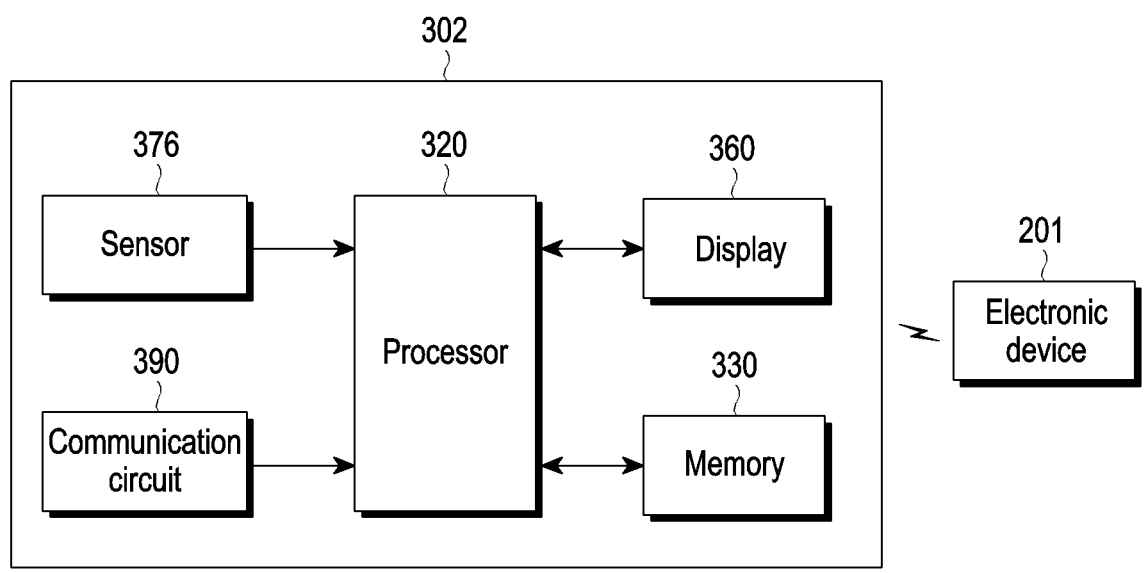
FIG. 3 is a block diagram illustrating an internal configuration of a wearable device according to an embodiment of the disclosure.

FIG. 3 is a block diagram illustrating an internal configuration of a wearable device 302 according to an embodiment of the disclosure.

Referring to FIG. 3, a wearable device 302 may include a processor 320, a memory 330, a display 360, a sensor 376, and a communication circuit 390. In an embodiment of the disclosure, the sensor 376 may operate substantially in the same manner as the sensor module 276 of FIG. 2. For example, the sensor 376 may detect the operational state (e.g., wearing state) of the wearable device 302 and the state (e.g., sleep state, health state, or exercise state) of the user wearing the wearable device 302, or external environmental state (e.g., temperature) and generate an electrical signal or data value corresponding to the detected state.

In an embodiment of the disclosure, the sensor 376 may include at least one sensor for detecting the operational state of the wearable device 302, the state of the user wearing the wearable device 302, and/or the ambient environment. In an embodiment of the disclosure, the sensor 376 may include an accelerometer or gyroscope for detecting the motion of the wearable device 302. In an embodiment of the disclosure, the sensor 376 may include a bio sensor for obtaining bio signals related to the state (e.g., sleep state, health state, or exercise state) of the user wearing the wearable device 302.

In an embodiment of the disclosure, the sensor 376 may include, e.g., a distance sensor or an illuminance sensor and may obtain, e.g., sensor data related to the user's ambient environment. In an embodiment of the disclosure, the sensor 376 may include an air sensor. For example, the sensor 376 may obtain sensor data including temperature information, humidity information, wind information, or air cleanliness information from the air sensor.

According to an embodiment of the disclosure, the memory 330 may store information, data and parameters necessary for the operation of the wearable device 302, and sensor data.

According to an embodiment of the disclosure, the processor 320 may generate report information based on the sensor data obtained by the sensor 376 upon communication connection with the electronic device 201. In an embodiment of the disclosure, the report information may include the sensor data itself, or the user's state or the operational state of the wearable device 302 obtained by analyzing the sensor data. The processor 320 may store the report information in the memory 330 and/or transmit it to the electronic device 201 through the communication circuit 390.

According to an embodiment of the disclosure, the display 360 may display a user interface related to the operation of the wearable device 302 under the control of the processor 320. According to an embodiment of the disclosure, the display 360 may display the sensor data from the sensor 376 and the state information analyzed by the processor 320 (e.g., the operational state of the wearable device 302 or the user's state).

According to an embodiment of the disclosure, the display 360 may include a touch sensor for detecting a touch as well as simultaneously supporting an input/output function of data. In an embodiment of the disclosure, the display 360 may display a notification (e.g., a wearing notification or a charging notification) for controlling the wearable device 302 under the control of the processor 320. In an embodiment of the disclosure, the processor 320 may receive a notification from the IoT server (e.g., the first IoT server 110) directly or through the electronic device 201 and may control the display 360 to display the notification.

According to an embodiment of the disclosure, the communication circuit 390 may communicate with the electronic device 201 under the control of the processor 320. According to an embodiment of the disclosure, the communication circuit 390 may perform communication using at least one communication scheme among communication schemes including Zigbee, Z-Wave, Wi-Fi, Bluetooth, ultra-wide band (UWB), wireless USB, or near field communication (NFC). For example, the communication circuit 390 may be communicatively connected to the electronic device 201 through short-range communication, such as Bluetooth or BLE. If the user wearing the wearable device 302 is not positioned within a short-range communication connectable radius of the electronic device 201, the communication circuit 390 may perform communication with the electronic device 201 based on a network communication scheme, such as long-term evolution (LTE).

Figure 4:
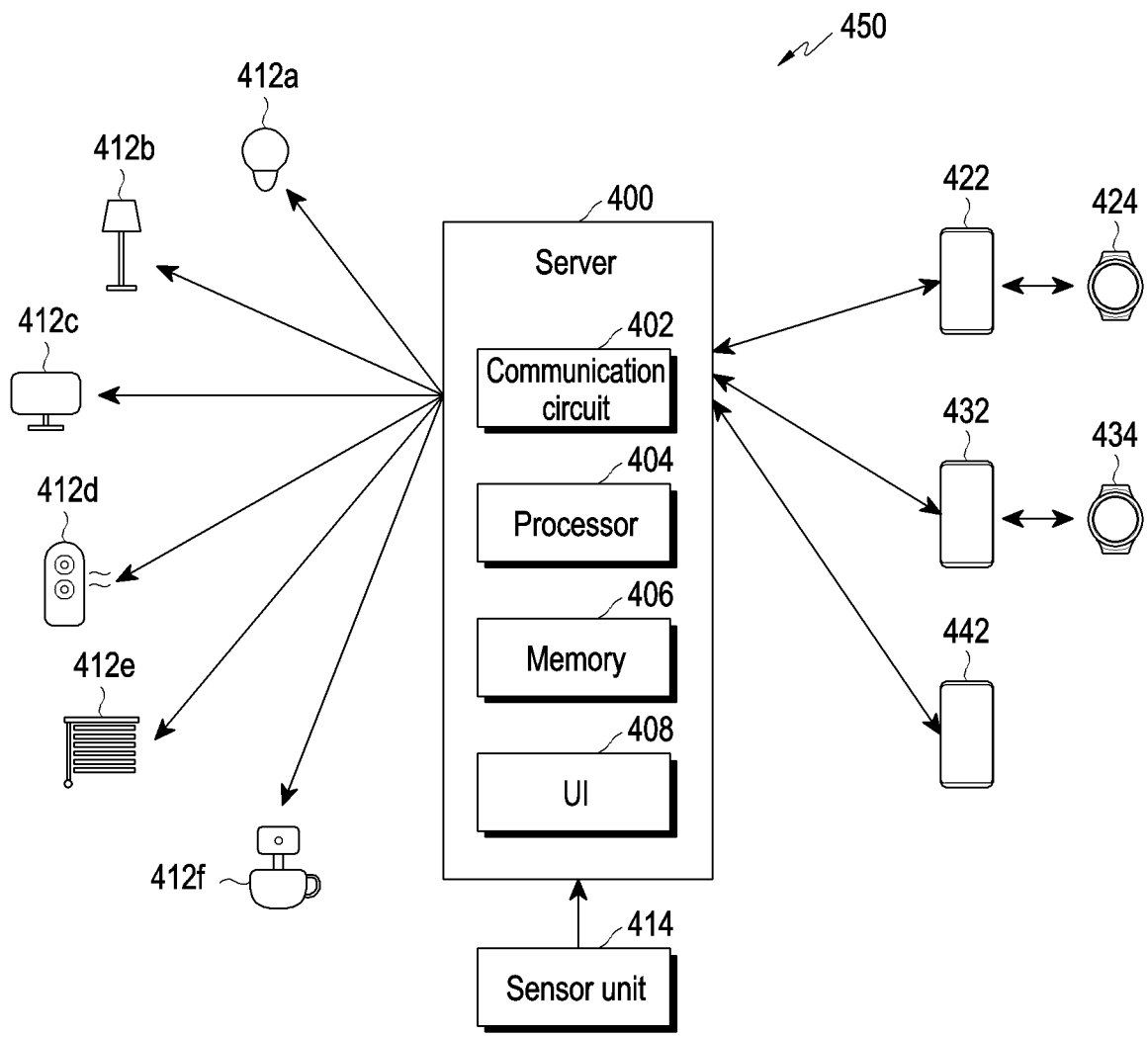
FIG. 4 is a block diagram illustrating a configuration of a home network environment according to an embodiment of the disclosure.

FIG. 4 is a block diagram illustrating a configuration of a home network environment according to an embodiment of the disclosure.

Referring to FIG. 4, a home network 450 may include at least one of a server 400 (e.g., the first IoT server 110), at least one electronic device 422, 432, and 442 (e.g., the device 124 or electronic device 201) which may operate as controller devices, at least one home device 412a, 412b, 412c, 412d, 412e, and 412f (e.g., target devices 121, 122, and 123) which may operate as controlled devices, and a sensor unit 414.

In an embodiment of the disclosure, each of the electronic devices 422, 432, and 442 may identify the states of the home devices 412a, 412b, 412c, 412d, 412e, and 412f to be used by the user in the smart home service or control the operation of the home devices 412a, 412b, 412c, 412d, 412e, and 412f. For example, each electronic device 422, 432, and 442 may be an electronic device equipped with a display and a user interface, such as a personal electronic device, such as a smartphone, a television (TV), or a control console. The electronic devices 422, 432, and 442 may correspond to different users, respectively, or at least one user. In an embodiment of the disclosure, the electronic devices 422, 432, and 442 may communicate with the server 400 by using a long-range communication network, such as the Internet, communication network (e.g., LAN or WAN), or cellular network, or through a short-range communication network, such as Bluetooth or Wi-Fi. In an embodiment of the disclosure, the electronic devices 422, 432, and 442 may communicate with the home devices 412a, 412b, 412c, 412d, 412e, and 412f using a long-range communication network or through a short-range communication network.

In an embodiment of the disclosure, the home devices 412a, 412b, 412c, 412d, 412e, and 412f may be controlled by at least one of the server 400 or the electronic devices 422, 432, and 442 and may be home appliances, such as a lighting device, a television, an air conditioner, a window treatment, a coffee machine, or a washing machine. The home devices 412a, 412b, 412c, 412d, 412e, and 412f may be connected to the server 400 and/or at least one of the electronic devices 422, 432, and 442 using wired communication or wireless communication.

In an embodiment of the disclosure, the sensor unit 414 may include at least one sensor (e.g., a motion sensor, a sound sensor, and/or a temperature sensor) capable of detecting an environment inside and/or outside the home network and report the sensor data collected by the at least one sensor to the server 400 or may directly (e.g., without passing through the server 400) report it to at least one designated electronic device (e.g., the electronic device 422). In an embodiment of the disclosure, the sensor unit 414 may include an occupancy sensor for detecting a motion or sound in each room (e.g., living room, bed room, kitchen, or bathroom) included in the home network 450 to determine whether the user is in the room.

In an embodiment of the disclosure, the server 400 may be an electronic device operating the smart home service, e.g., a home server or home gateway disposed in the house or a smart home server disposed outside the house. The server 400 may store and manage information for the smart home service (e.g., at least one of home information 700, home automation configuration information 900, sleep preparation setting information 1302, sleep start setting information 1312, and wakeup alarm setting information 1314), receive information or commands related to the control of the home devices 412a, 412b, 412c, 412d, 412e, and 412f from the electronic devices 422, 432, and 442, and/or the sensor unit 414, and transmit control commands for performing a specific operation to the home devices 412a, 412b, 412c, 412d, 412e, and 412f.

In an embodiment of the disclosure, the server 400 may provide a mode service for simultaneously controlling one or more home devices (e.g., at least one of the home devices 412a, 412b, 412c, 412d, 412e, and 412f) through a single command. In an embodiment of the disclosure, the mode service may set a condition for executing a specific control command per designated operation mode (e.g., go out mode, back home mode, sleep mode, or wakeup mode). In an embodiment of the disclosure, in response to a condition set for the designated operation mode being met, the server 400 may transmit a specific control command to at least one home device (e.g., at least one of the home devices 412a, 412b, 412c, 412d, 412e, and 412f) or may transmit a specific control command to at least one home device (e.g., at least one of the home devices 412a, 412b, 412c, 412d, 412e, and 412f) at the request of any one (e.g., the electronic device 422) of the electronic devices 422, 432, and 442.

In an embodiment of the disclosure, the server 400 may include a communication circuit 402, a processor 404, a memory 406 and a user interface (UI) 408. In an embodiment of the disclosure, the communication circuit 402 may include at least one communication module for long-range communication and/or short-range communication and communicate with the electronic devices 422, 432, and 442 and the home devices 412a, 412b, 412c, 412d, 412e, and 412f through long-range communication network and/or short-range communication network.

In an embodiment of the disclosure, wearable devices 424 and 434 corresponding to at least some (e.g., the electronic devices 422 and 432) among the electronic devices 422, 432, and 442 may be included in the home network 450. In an embodiment of the disclosure, the server 400 may store and manage, in the memory 406, device information related to the electronic devices 422, 432, and 442 for each of one or more users registered in the home network 450 and wearable devices 424 and 434 corresponding thereto. As an example, the device information may be configured as shown in Table 1 below.

TABLE 1

| user | device | location | wearables | position |
|---|---|---|---|---|
| user #1 | electronic device #1 | living room | wearable device #1 | bedroom #1 |
| user #2 | electronic device #2 | bedroom #1 | wearable device #2 | bedroom #1 |
| user #3 | electronic device #3 | bedroom #2 | (no wearable registered) | — |

As an example, registration information may include electronic device #1 (e.g., the electronic device 422) and wearable device #1 (e.g., the wearable device 424) for user #1, electronic device #2 (e.g., the electronic device 432) and wearable device #2 (e.g., the wearable device 434) for user #2, and electronic device #3 (e.g., the electronic device 442) and 'no wearable registered' for user #3.

In an embodiment of the disclosure, the server 400 may store and manage, in the memory 406, home device information related to the types, locations, and controllable functions of the home devices 412a, 412b, 412c, 412d, 412e, and 412f registered in the home network 450. As an example, the home device information may be configured as shown in Table 2 below.

TABLE 2

| device | Type | location | function |
|---|---|---|---|
| home device #1 | light #1 | living room | on, off, brightness level |
| home device #2 | light #2 | bedroom #1 | on, off, brightness level |
| home device #3 | television | living room | on, off, volume level |
| home device #4 | air conditioner | living room | on, off, desired temperature |
| home device #5 | curtain | living room | close, open, open steps |
| home device #6 | coffee machine | kitchen | on, off |

For example, home devices #1 to 6 may be the home devices 412a, 412b, 412c, 412d, 412e, and 412f.

In an embodiment of the disclosure, the server 400 may be a computer device, a home gateway, or an electronic device (e.g., the electronic device 422) and be disposed inside or outside the home network 450 and is not limited in type.

Figure 16:
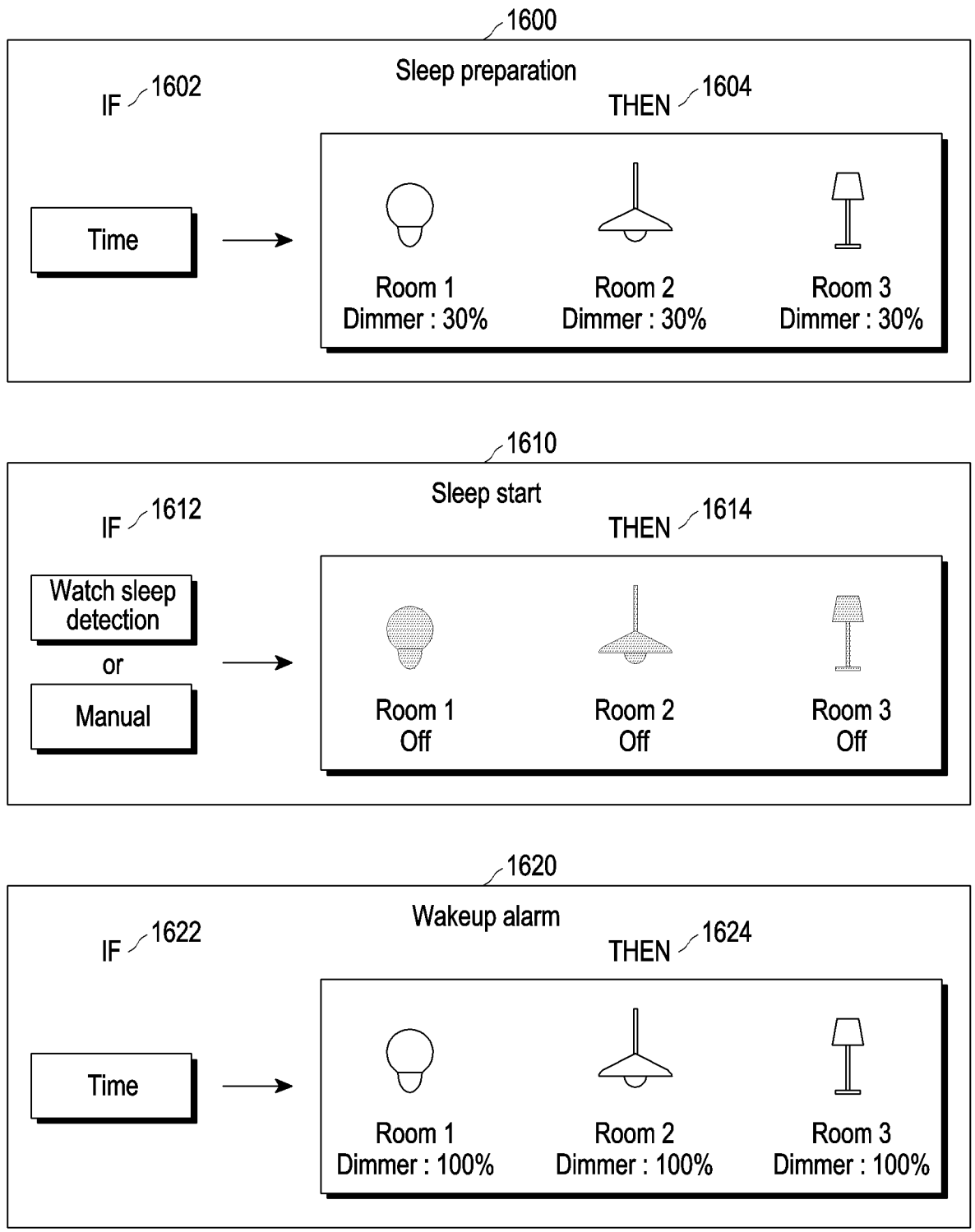
FIG. 16 is a view illustrating a home network control based on sleep detection according to an embodiment of the disclosure.
Figure 17:
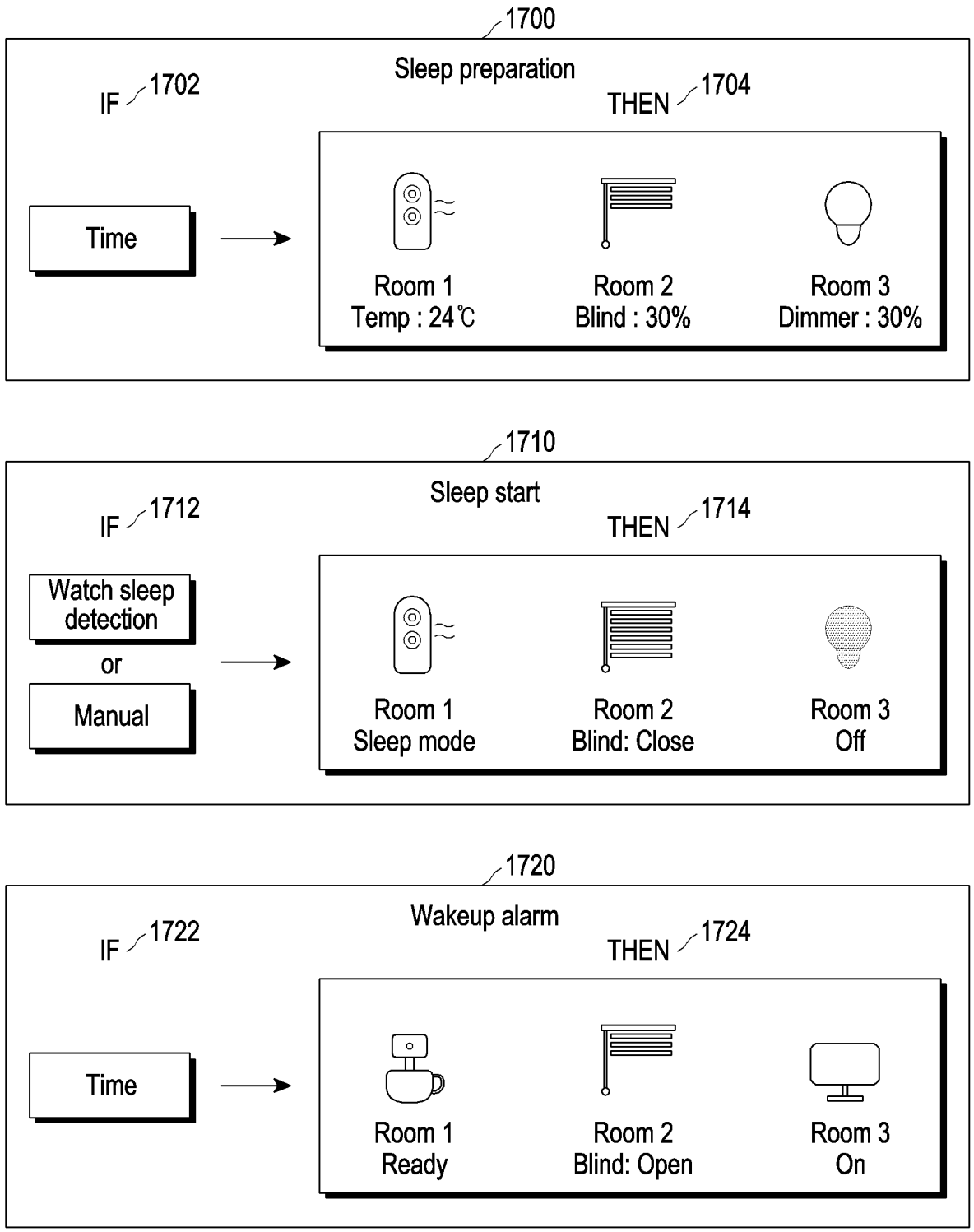
FIG. 17 is a view illustrating a home network control based on sleep detection according to an embodiment of the disclosure.
Figure 18:
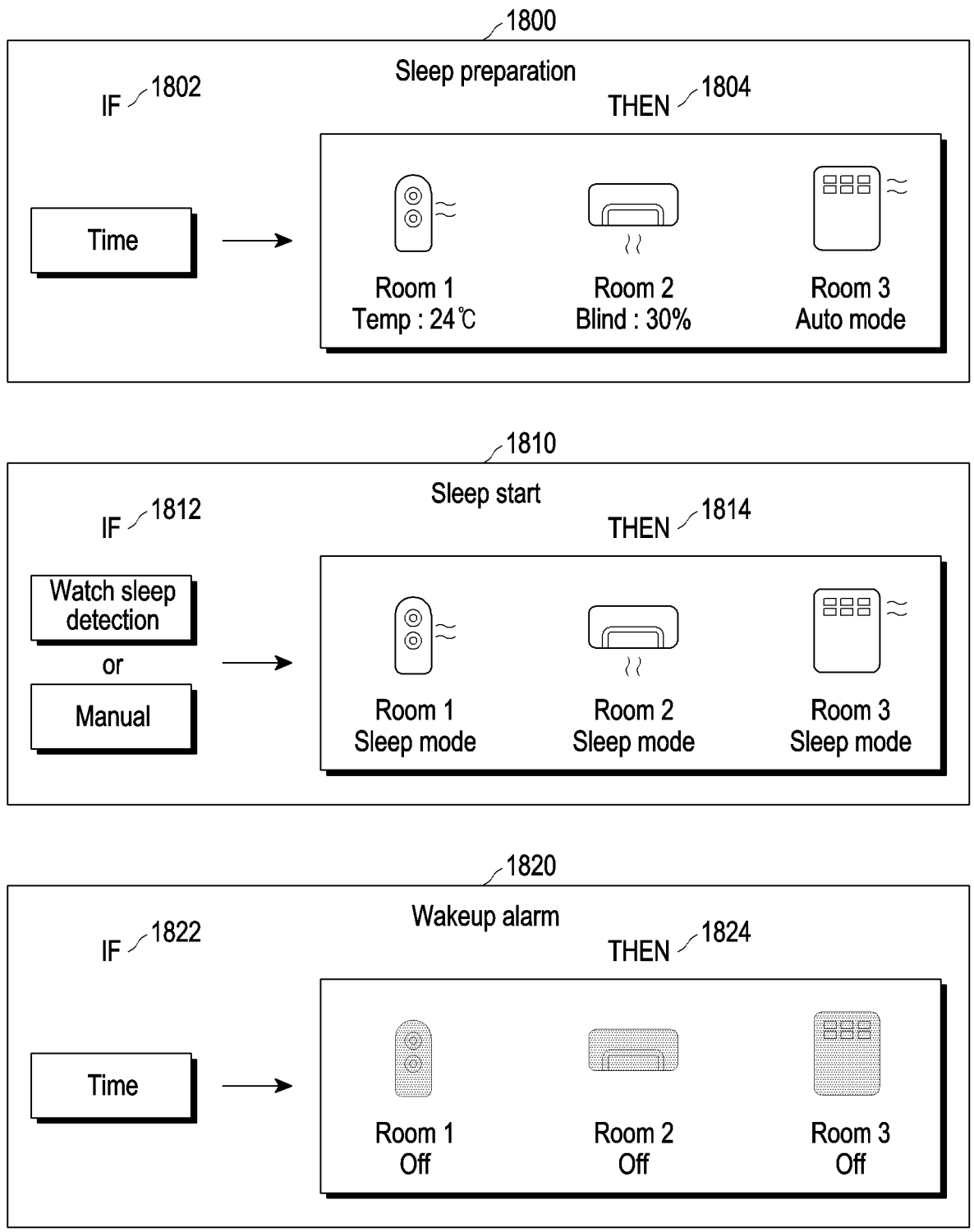
FIG. 18 is a view illustrating a home network control based on sleep detection according to an embodiment of the disclosure.

For example, the sleep preparation setting information 1302 may be the sleep preparation setting information 1600 of FIG. 16, the sleep preparation setting information 1700 of FIG. 17, or the sleep preparation setting information 1800 of FIG. 18. For example, the sleep start setting information 1312 may be the sleep start setting information 1610 of FIG. 16, the sleep start setting information 1710 of FIG. 17, or the sleep start setting information 1810 of FIG. 18. For example, the wakeup alarm setting information 1314 may be the wakeup alarm setting information 1620 of FIG. 16, the wakeup alarm setting information 1720 of FIG. 17, or the wakeup alarm setting information 1820 of FIG. 18.

Figure 5:
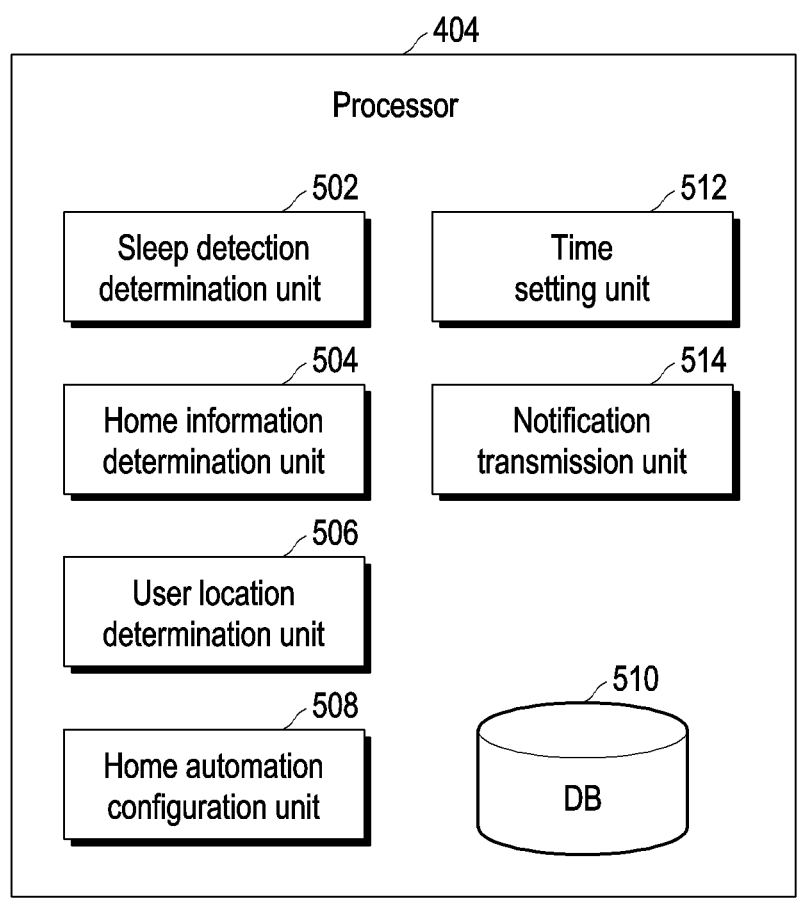
FIG. 5 is a view illustrating functions of a server according to an embodiment of the disclosure.

FIG. 5 is a view illustrating functions of a server according to an embodiment of the disclosure.

Referring to FIG. 5, the processor 404 of the server 400 may include at least one of a sleep detection determination unit 502, a home information determination unit 504, a user location determination unit 506, a home automation configuration unit 508, a database (DB) 510, a time setting unit 512, or an alarm transmission unit 514. At least one of the illustrated components 502, 504, 506, 508, 512, and 514 may be implemented in software executed by the processor 404. The database 510 may be a component of the processor 404 or the memory 406.

In an embodiment of the disclosure, the sleep detection determination unit 502 may be configured to detect the sleep state of users located in the home network (e.g., the home network 450). In an embodiment of the disclosure, the sleep detection determination unit 502 may detect the user's sleep state through the electronic device (e.g., at least one of the electronic devices 422, 432, and 442) carried by the user. In an embodiment of the disclosure, the sleep detection determination unit 502 may detect the user's sleep state through the wearable device (e.g., at least one of the wearable devices 424 and 434) worn by the user. In an embodiment of the disclosure, the sleep detection determination unit 502 may determine the user's sleep state by detecting the motion, sound, and/or occupancy through a sensor unit (e.g., the sensor unit 414) in the home network 450. The sleep detection determination unit 502 is an example, and may be further described in connection with FIG. 6.

In an embodiment of the disclosure, the home information determination unit 504 may collect, analyze, and store information related to the configuration of the home network (e.g., the home network 450) (hereinafter referred to as home information). In an embodiment of the disclosure, the home information may include the location and configuration of the house in which the home network 450 is installed (e.g., the number, type, and arrangement of the rooms constituting the home network 450). According to an embodiment of the disclosure, the home information may identify electronic devices (e.g., the electronic devices 422, 432, and 442 and/or the wearable devices 424 and 434) registered in the home network 450. In an embodiment of the disclosure, the home network may identify home devices (e.g., home devices 412a, 412b, 412c, 412d, 412e, and 412f) registered in the home network 9450. The home information determination unit 504 is an example, and may be further described in connection with FIG. 7.

In an embodiment of the disclosure, the user location determination unit 506 may determine and store the locations of users registered in the home network 450. In an embodiment of the disclosure, the location may indicate whether the user is located within the home network 450, the geographic location of the user and/or the space (room) in which each user is located. In an embodiment of the disclosure, the location may be identified by the electronic device (e.g., any one of the electronic devices 422, 432, and 442) carried by the user and/or the wearable device (e.g., any one of the wearable devices 424 and 434) worn by the user. The user location determination unit 506 is an example, and may be further described in connection with FIG. 8.

In an embodiment of the disclosure, the home automation configuration unit 508 may create and manage home automation configuration information including conditions and operations for home automation operations according to at least one or a combination of embodiments of the disclosure. In an embodiment of the disclosure, the home automation configuration information may include conditions and operations according to a designated operation mode (e.g., go out mode, back home mode, sleep mode, or wakeup mode). As an example, the condition may be set through the user interface 408, an electronic device (e.g., any one of the electronic devices 422, 432, and 442), and/or the Internet and be stored in the server 400. In an embodiment of the disclosure, the condition may include time, device status, and/or member location. In an embodiment of the disclosure, the operation may control the home devices (e.g., the home devices 412a, 412b, 412c, 412d, 412e, and 412f). The home automation configuration unit 508 is an example, and may be further described in connection with FIG. 9.

In an embodiment of the disclosure, the database 510 may store the users' sleep states determined by the sleep detection determination unit 502, the home information determined by the home information determination unit 504, the user location information determined by the user location determination unit 506, and/or the home automation configuration information generated by the home automation configuration unit 508.

In an embodiment of the disclosure, the time setting unit 512 may receive settings of the bedtime and/or wakeup alarm time according to at least one or a combination of embodiments of the disclosure, through, e.g., the electronic device (e.g., any one of the electronic devices 422, 432, and 442) or the user interface 408 and store them. In an embodiment of the disclosure, the time setting unit 512 may receive and store detailed settings for a sleep preparation operation and a wakeup alarm operation. The time setting unit 512 is an example, and may be further described in connection with FIG. 14.

In an embodiment of the disclosure, the notification transmission unit 514 may detect and trigger an occurrence of a notification according to at least one or a combination of embodiments of the disclosure, determine the content of the notification, and transmit the generated notification to the target of the notification. The target of the notification may be an electronic device (e.g., any one of the electronic devices 422, 432, and 442) or a wearable device (e.g., any one of the wearable devices 424 and 434). The notification transmission unit 514 is an example, and may be further described in connection with FIG. 15.

Figure 6:
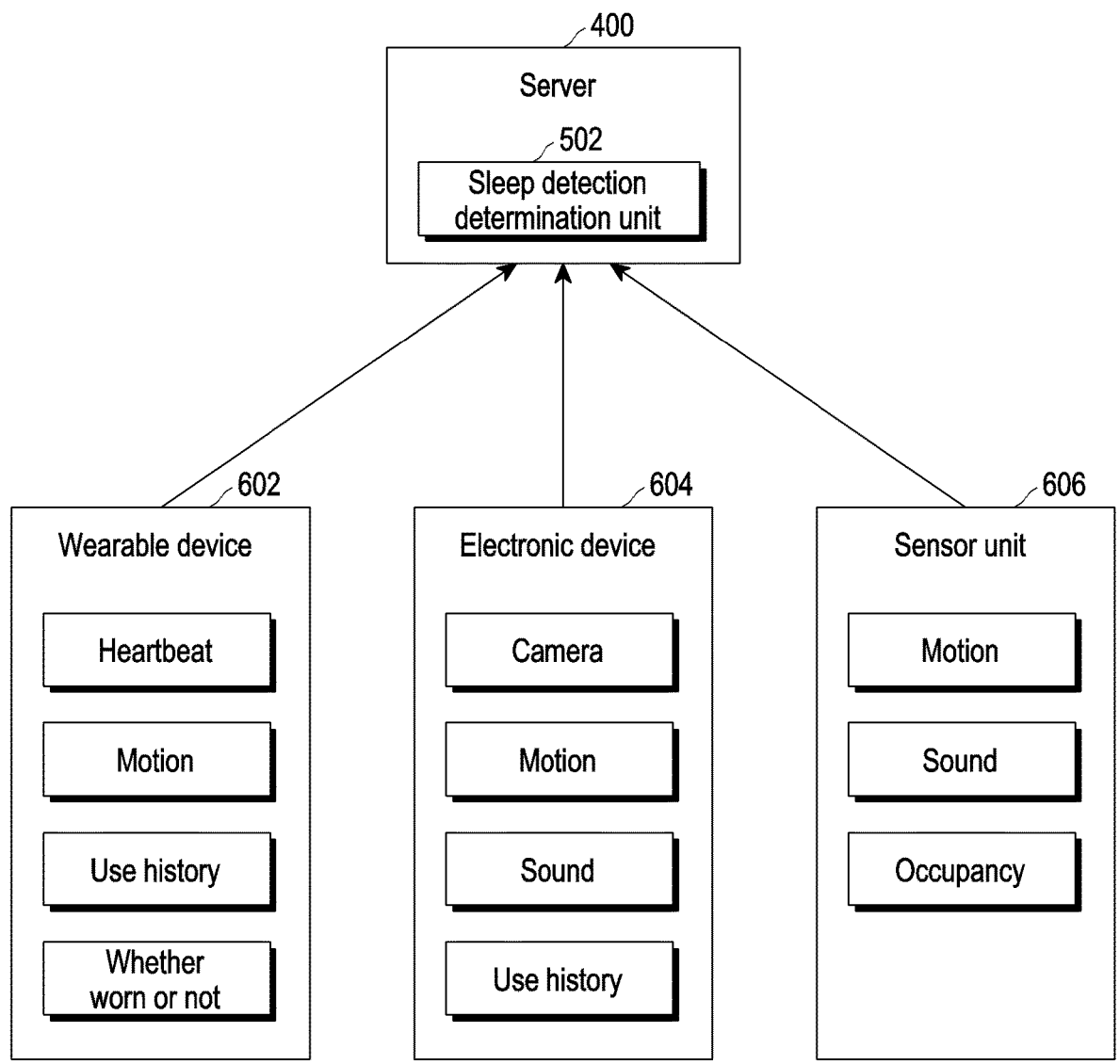
FIG. 6 is a view illustrating sleep detection according to an embodiment of the disclosure.

FIG. 6 is a view illustrating sleep detection according to an embodiment of the disclosure.

Referring to FIG. 6, the server 400 (e.g., the sleep detection determination unit 502) may receive information related to the sleep state from a wearable device 602 (e.g., any one of the wearable devices 424 and 434), an electronic device 604 (e.g., any one of the electronic devices 422, 432, and 442), and/or the sensor unit 606 (e.g., the sensor unit 414).

In an embodiment of the disclosure, the wearable device 602 may detect at least one of the user's heartbeat, motion, use history, or whether worn or not, and report the detected result to the server 400 (e.g., the sleep detection determination unit 502) periodically or at the request of the server 400 (e.g., the sleep detection determination unit 502). In an embodiment of the disclosure, the wearable device 602 may report the detected result, as it is, to the server 400 (e.g., the sleep detection determination unit 502) or report a sleep state (e.g., sleep or non-sleep) analyzed based on the detected result to the server 400 (e.g., the sleep detection determination unit 502).

In an embodiment of the disclosure, the electronic device 604 may collect the results detected through the camera, motion sensor, and/or sound sensor and/or use history and report the collected results to the server 400 (e.g., the sleep detection determination unit 502) periodically or at the request of the server 400 (e.g., the sleep detection determination unit 502). In an embodiment of the disclosure, the electronic device 604 may detect the movement or motion of the electronic device 604 through the camera. In an embodiment of the disclosure, the electronic device 604 may detect the motion or sound through the motion sensor or sound sensor. The detected result may be used to analyze the user's sleep or non-sleep by the electronic device 604 or the server 400 (e.g., the sleep detection determination unit 502). In an embodiment of the disclosure, the wearable device 602 may report the collected results, as it is, to the server 400 (e.g., the sleep detection determination unit 502) or report a sleep state (e.g., sleep or non-sleep) analyzed based on the detected result to the server 400 (e.g., the sleep detection determination unit 502).

In an embodiment of the disclosure, the sensor unit 606 may collect the results detected through the motion sensor, sound sensor, and/or occupancy sensor and report the collected results to the server 400 (e.g., the sleep detection determination unit 502) periodically or at the request of the server 400 (e.g., the sleep detection determination unit 502). The detected result may be used to analyze the user's sleep or non-sleep by the server 400 (e.g., the sleep detection determination unit 502).

In an embodiment of the disclosure, the server 400 (e.g., the sleep detection determination unit 502) may determine the user's sleep or non-sleep corresponding to the wearable device 602 and/or the electronic device 604 based on various information reported from the wearable device 602, the electronic device 604, and/or the sensor unit 606. In an embodiment of the disclosure, the server 400 (e.g., the sleep detection determination unit 502) may determine the user's location (e.g., a bedroom) corresponding to the wearable device 602 and/or the electronic device 604 through the sensor unit 606 and determine whether a motion and/or sound is detected in the user's location, thereby determining whether the user sleeps.

In embodiments of the disclosure, other various methods not disclosed herein may be used to determine whether the user sleeps, and embodiments of the disclosure are not limited to such methods.

Figure 7:
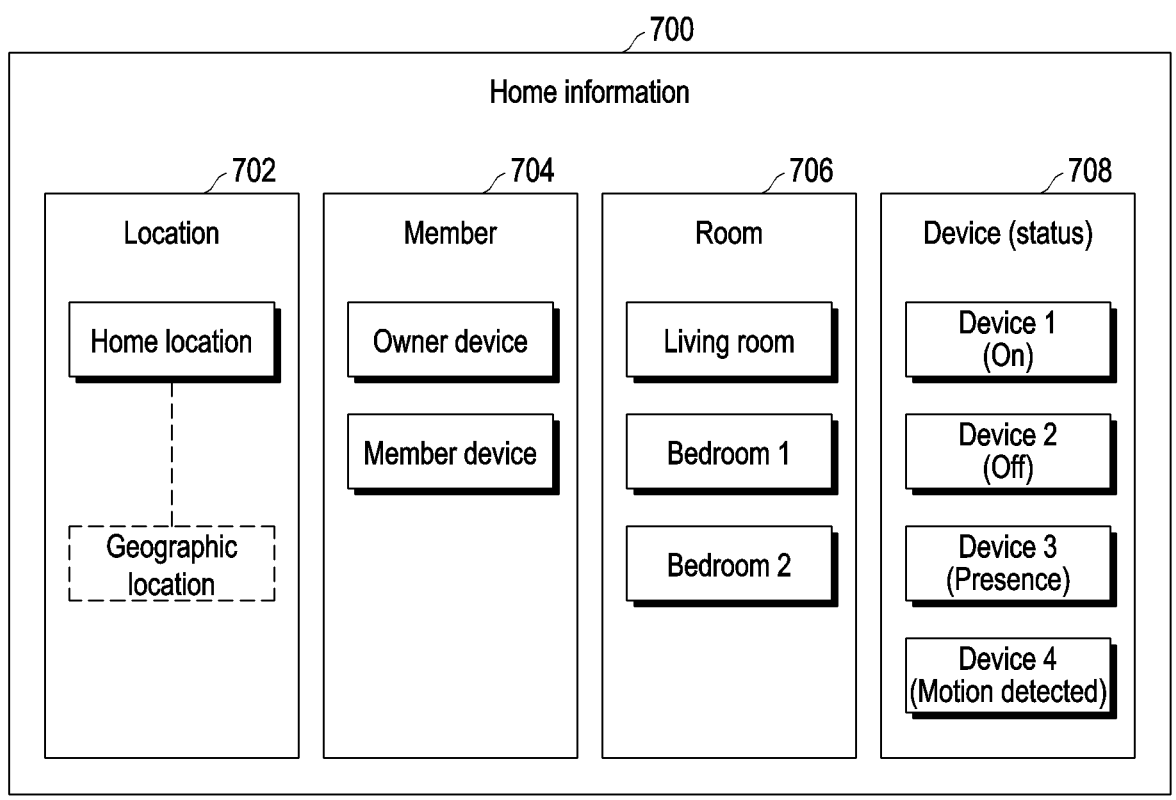
FIG. 7 is a view illustrating home information according to an embodiment of the disclosure.

FIG. 7 is a view illustrating home information according to an embodiment of the disclosure.

Referring to FIG. 7, the server 400 (e.g., the home information determination unit 504) may manage various home information 700. In an embodiment of the disclosure, the home information 700 may include at least one of location information 702, member information 704, room information 706, or device information 708.

In an embodiment of the disclosure, the location information 702 may include the home location and/or each user's geographic location indicating whether the users registered in the home network (e.g., the home network 450) are located in the home. In an embodiment of the disclosure, the server 400 (e.g., the home information determination unit 504) may determine the home location and/or geographic location of each user based on the locations of the electronic devices (e.g., the electronic devices 422, 432, and 442 and/or wearable devices 424 and 434) corresponding to the users registered in the home network 450 and store them in the location information 702.

In an embodiment of the disclosure, the member information 704 may include identification information (e.g., unique number and/or media access control (MAC) address) about the electronic devices (e.g., the electronic devices 422, 432, and 442 and/or the wearable devices 424 and 434) registered in the home network 450 and additional information (e.g., model name, version, priority, and/or supportable functions).

In an embodiment of the disclosure, the electronic devices may have priorities settable by the user. In an embodiment of the disclosure, the electronic devices may include an owner device (e.g., the electronic device 422) and at least one member device (e.g., the electronic devices 432 and 442). For example, the owner device may have a higher priority than the member device. For example, the owner device may have a setting authority for the server 400. In an embodiment of the disclosure, by the setting authority, the owner device may input at least one of the sleep preparation setting information, sleep start setting information, and wakeup alarm setting information to the server 400.

In an embodiment of the disclosure, the room information 706 may include the number, names, and/or types of the rooms constituting the home network 450. As an example, the room information 706 may include a living room, bedroom 1, and/or bedroom 2. In an embodiment of the disclosure, the device information 708 may include identification information (e.g., unique number and/or media access control (MAC) address) about the home devices (e.g., the home devices 412a, 412b, 412c, 412d, 412e, and 412f and/or the sensor unit 414) registered in the home network 450 and additional information (e.g., model name, version, location, operational state, and/or supportable functions). In an embodiment of the disclosure, the device information 708 may include 'On' as state information about device 1 (e.g., a lighting device in the living room), 'Off' as state information about device 2 (e.g., a lighting device in room 1), 'presence' as state information about device 3 (e.g., an occupancy sensor in the kitchen), and 'motion detected' as state information about device 4 (e.g., a motion sensor in the entrance).

Figure 8:
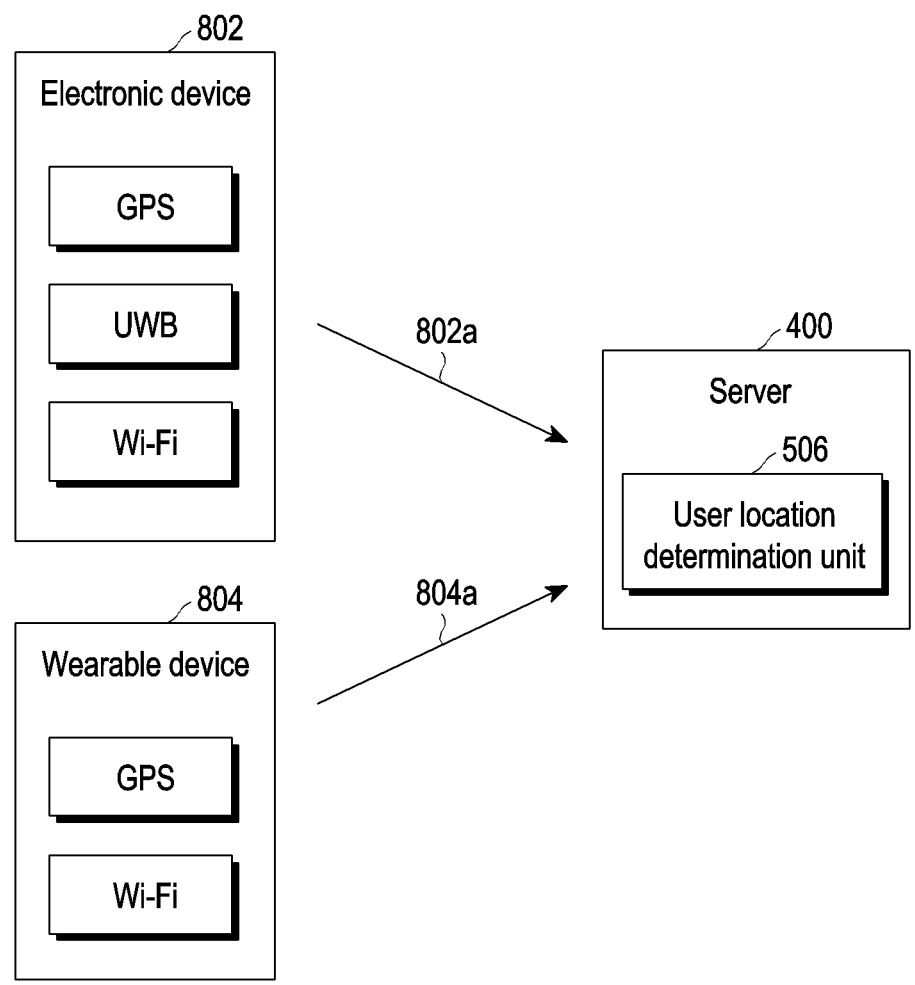
FIG. 8 is a view illustrating determination of a user's location according to an embodiment of the disclosure.

FIG. 8 is a view illustrating determination of a user's location according to an embodiment of the disclosure.

Referring to FIG. 8, the server 400 (e.g., the user location determination unit 506) may receive information related to the user's location from an electronic device 802 (e.g., any one of the electronic devices 422, 432, and 442) and/or the wearable device 804 (e.g., any one of the wearable devices 424 and 434).

In an embodiment of the disclosure, the electronic device 802 may identify the location of the electronic device 802 (e.g., any one room or geographic location in the home network 450) using at least one of, e.g., the global positioning system (GPS), ultra-wide band (UWB), or Wi-Fi and report information 802a about the identified location to the server 400 (e.g., the user location determination unit 506). In an embodiment of the disclosure, the information 802a about the location may be reported periodically or at the request of the server 400 (e.g., the user location determination unit 506). The server 400 (e.g., the user location determination unit 506) may determine and store the user's location corresponding to the electronic device 802 using the information 802a about the location.

In an embodiment of the disclosure, the wearable device 804 may identify the location of the wearable device 804 (e.g., any one room or geographic location in the home network 450) using at least one of, e.g., GPS or Wi-Fi and report information 804a about the identified location to the server 400 (e.g., the user location determination unit 506). In an embodiment of the disclosure, the information 804a about the location may be reported periodically or at the request of the server 400 (e.g., the user location determination unit 506). The server 400 (e.g., the user location determination unit 506) may determine the user's location corresponding to the wearable device 804 using the information 804a about the location and store it in, e.g., the location information 702 of the home information 700.

In an embodiment of the disclosure, in response to the location information 802a and 804a about the electronic device 802 and the wearable device 804 corresponding to the same user doing not match, the server 400 (e.g., the user location determination unit 506) may determine that the location information 804a about the wearable device 804 is exact or may transmit a signal to request information about the user's location to the electronic device 802 and/or wearable device 804.

Figure 9:
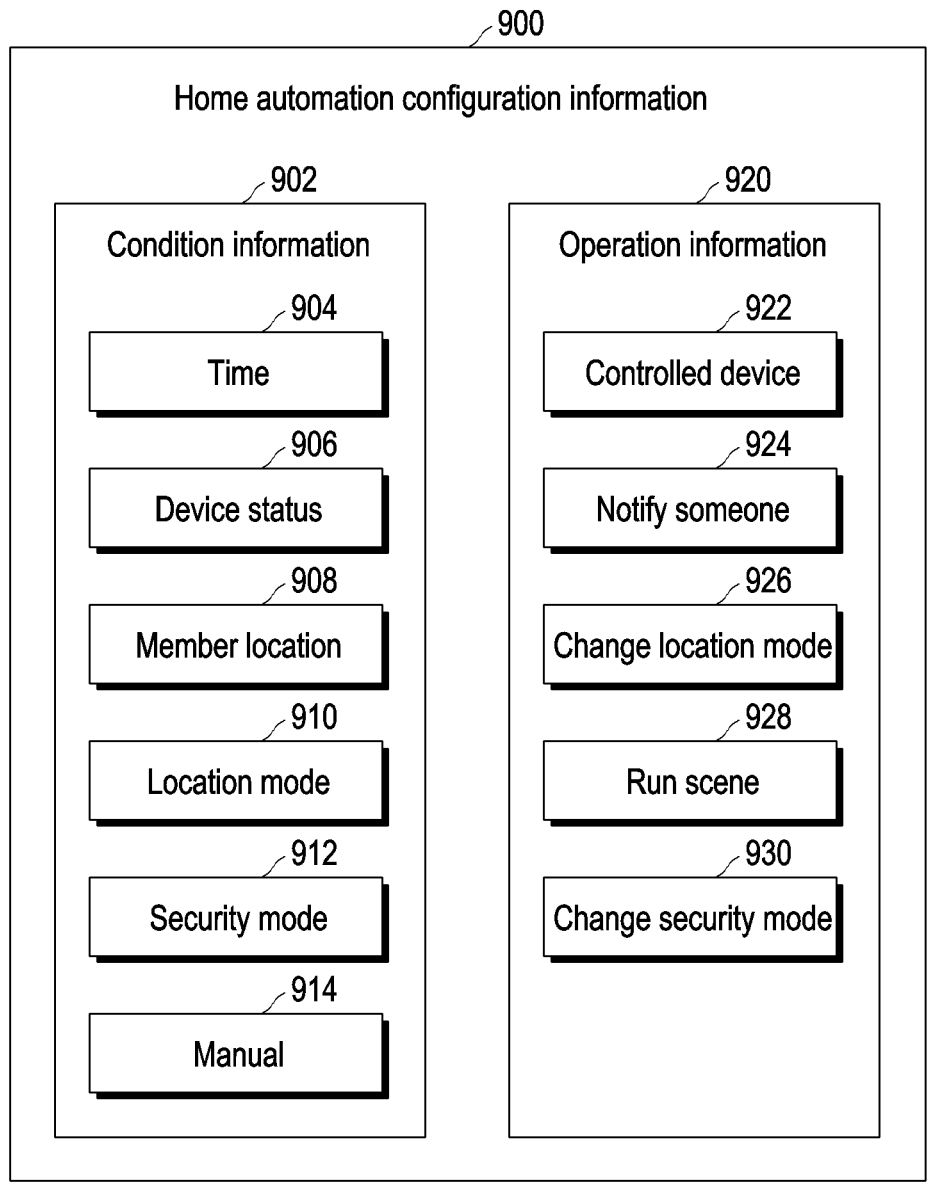
FIG. 9 is a view illustrating home automation configuration information according to an embodiment of the disclosure.

FIG. 9 is a view illustrating home automation configuration information according to an embodiment of the disclosure.

Referring to FIG. 9, the server 400 (e.g., the home automation configuration unit 508) may manage various home automation configuration information 900. In an embodiment of the disclosure, the home automation configuration information 900 may include condition information 902 and operation information 920. The condition information 902 may include a condition that may be designated by the user, and the operation information 920 may include an operation that should be performed by the target home device (e.g., at least one of the home devices 412a, 412b, 412c, 412d, 412e, and 412f) corresponding to the condition.

In an embodiment of the disclosure, the condition information 902 may include at least one of a time 904, a device status 906, a member location 908, a location mode 910, a security mode 912, or a manual setting 914. In an embodiment of the disclosure, the location mode 910 may include operation modes according to the users' locations, e.g., go out mode in which all the users are out, or occupancy mode in which at least one user is located in the home network 450. In an embodiment of the disclosure, the security mode 912 may include at least one of operation modes, e.g., high security mode or normal mode, according to the security level that may be set by the user.

In an embodiment of the disclosure, the operation information 920 may include at least one of controlled device 922, notify someone 924, change location mode 926, run scene 928, or change security mode 930.

In an embodiment of the disclosure, the server 400 (e.g., the home automation configuration unit 508) may generate home automation configuration information 900 based on the information input through the user interface 408, the electronic device (e.g., at least one of the electronic devices 422, 432, and 442), or the Internet. The home automation configuration information 900 may include, e.g., sleep preparation setting information for the sleep preparation operation, sleep start setting information for the sleep start operation, and/or the wakeup alarm setting information for the wakeup alarm operation. Example methods constituting the home automation configuration information 900 may be described in connection with FIGS. 10A, 10B, 11A to 11D, 12A, and 12B.

Figure 10A:
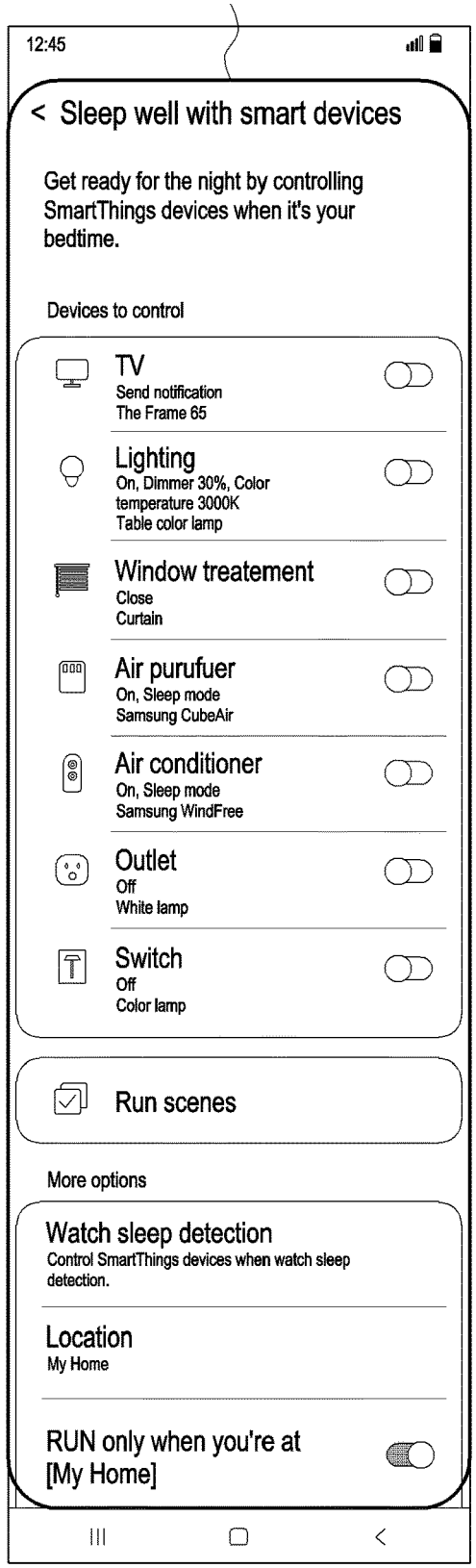
FIGS. 10A, 10B, and 10C are views illustrating a home automation configuration according to various embodiments of the disclosure.
Figure 10B:
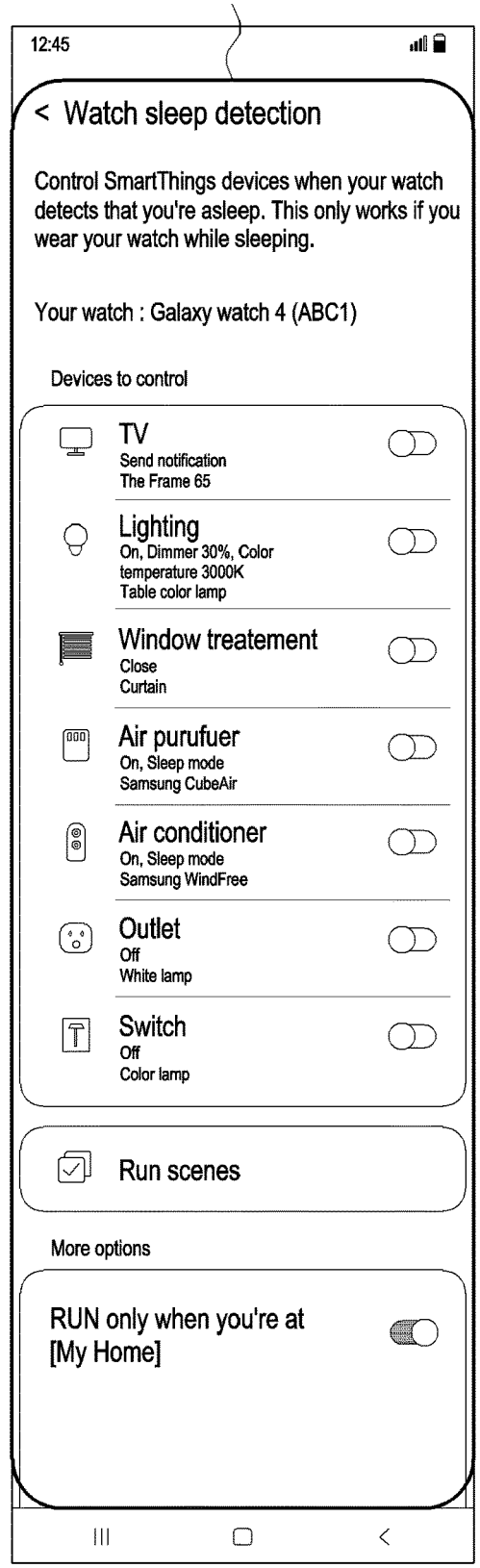
Figure 10C:
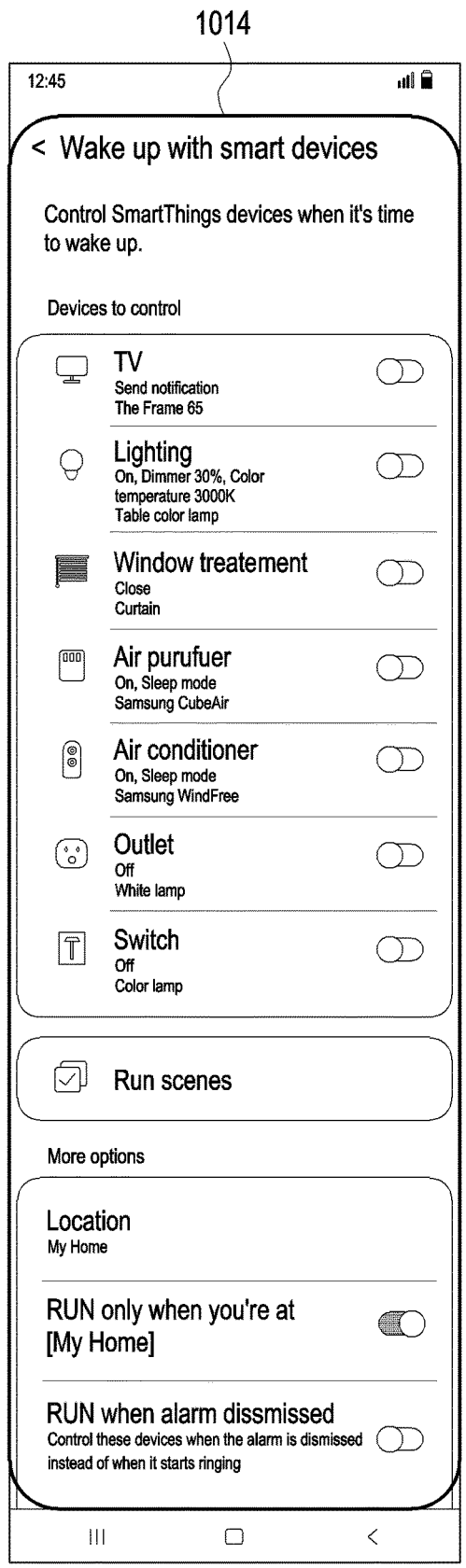

FIGS. 10A, 10B, and 10C are views illustrating a home automation configuration according to various embodiments of the disclosure.

Referring to FIG. 10A, the sleep preparation automation setting information 1002 may be displayed through the user interface 408 of the electronic device (e.g., at least one of the electronic devices 422, 432, and 442) or the server 400 and may provide menus for setting conditions and execution operation for the sleep preparation operation to control the home devices at the bedtime set by the user. As an example, the sleep preparation automation setting screen 1002 may include home devices to be controlled (e.g., TV, Lighting, Window treatment, Air purifier, Air conditioner, Outlet, or Switch), Run scenes, Watch sleep detection, location, or menu items for setting whether to perform the sleep preparation operation.

Referring to FIG. 10B, the sleep start automation setting screen 1012 may be displayed through the user interface 408 of the electronic device (e.g., at least one of the electronic devices 422, 432, and 442) or the server 400 and may provide menus for setting conditions and execution operation for the sleep start operation to control the home devices when detecting that the user is in the sleep state after the sleep preparation operation. As an example, the sleep start automation setting screen 1012 may include home devices to be controlled (e.g., TV, Lighting, Window treatment, Air purifier, Air conditioner, Outlet, or Switch), Run scenes, or menu items for setting whether to perform the sleep start operation.

Referring to FIG. 10C, the wakeup alarm automation setting information 1014 may be displayed through the user interface 408 of the electronic device (e.g., at least one of the electronic devices 422, 432, and 442) or the server 400 and may provide menus for setting conditions and execution operation for the wakeup alarm operation to control the home devices at the wakeup time set by the user. As an example, the wakeup alarm automation setting screen 1014 may include home devices to be controlled (e.g., TV, Lighting, Window treatment, Air purifier, Air conditioner, Outlet, or Switch), Run scenes, whether to run the wakeup alarm operation, or menu items for setting whether to perform the alarm release.

FIGS. 11A, 11B, 11C, and 11D are views illustrating settings of sleep preparation and wakeup alarm according to various embodiments of the disclosure.

Figure 11A:
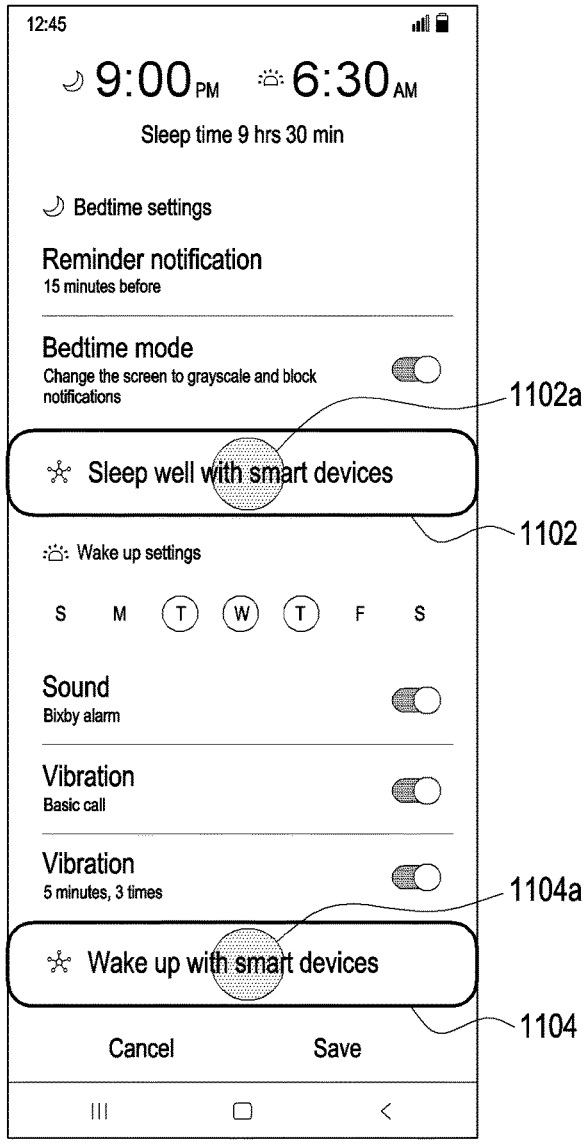
FIGS. 11A, 11B, 11C, and 11D are views illustrating settings of sleep preparation and wakeup alarm according to various embodiments of the disclosure.

Referring to FIG. 11A, the electronic device (e.g., at least one of the electronic devices 422, 432, and 442) may display a bedtime setting menu 1102 and/or a wakeup time setting menu 1104 upon running a clock application. Upon detecting a user input 1102a on the bedtime setting menu 1102, the electronic device (e.g., at least one of the electronic devices 422, 432, and 442) may display the sleep preparation automation setting screen 1110 of FIG. 11C. Upon detecting a user input 1104a on the wakeup time setting menu 1104, the electronic device (e.g., at least one of the electronic devices 422, 432, and 442) may display a wakeup alarm automation setting screen 1120 of FIG. 11D.

Figure 11B:
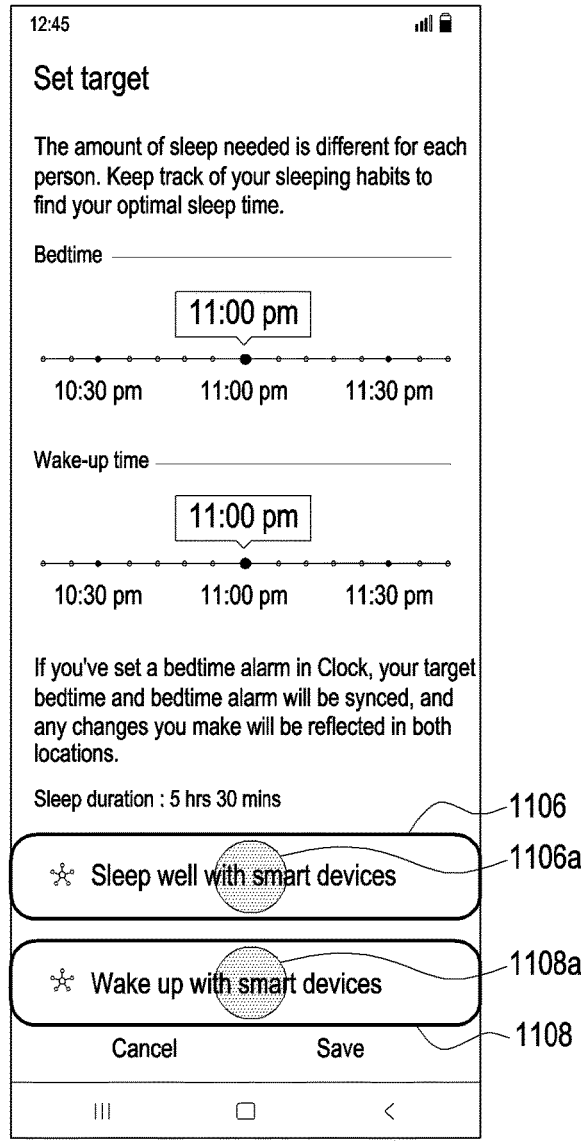

Referring to FIG. 11B, the electronic device (e.g., at least one of the electronic devices 422, 432, and 442) may display a bedtime setting menu 1106 and/or a wakeup time setting menu 1108 upon running a health application. Upon detecting a user input 1106a on the bedtime setting menu 1106, the electronic device (e.g., at least one of the electronic devices 422, 432, and 442) may display the sleep preparation automation setting screen 1110 of FIG. 11C. Upon detecting a user input 1108a on the wakeup time setting menu 1108, the electronic device (e.g., at least one of the electronic devices 422, 432, and 442) may display the wakeup alarm automation setting screen 1120 of FIG. 11D.

Figure 11C:
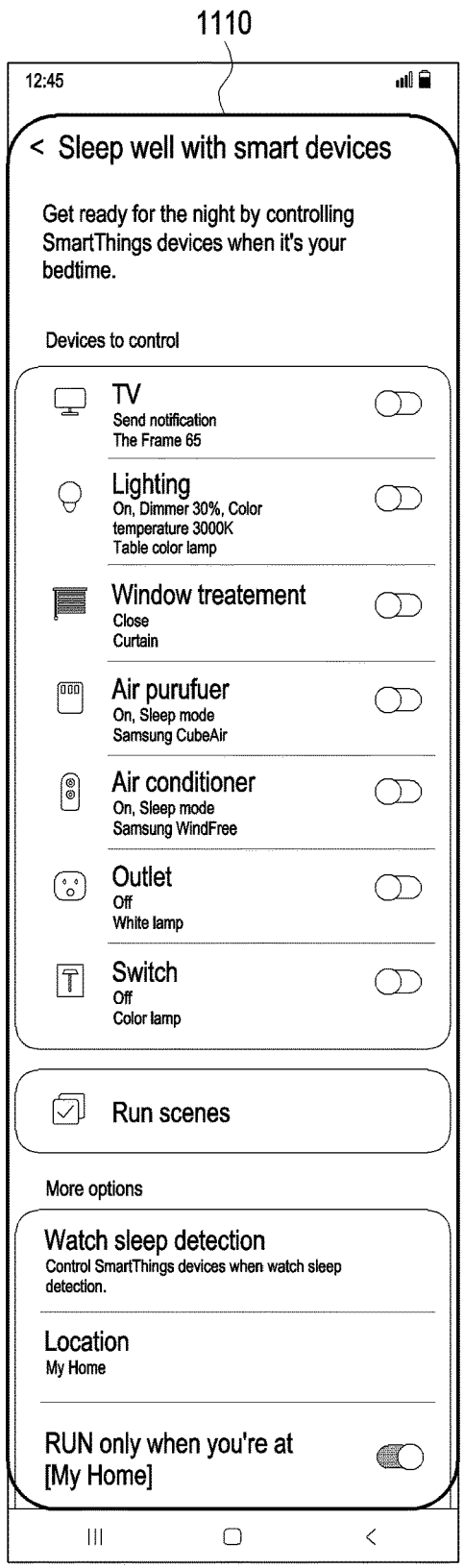

Referring to FIG. 11C, the sleep preparation automation setting screen 1110 may be the same as the sleep preparation automation setting screen 1002 of FIG. 10A as an example.

Figure 11D:
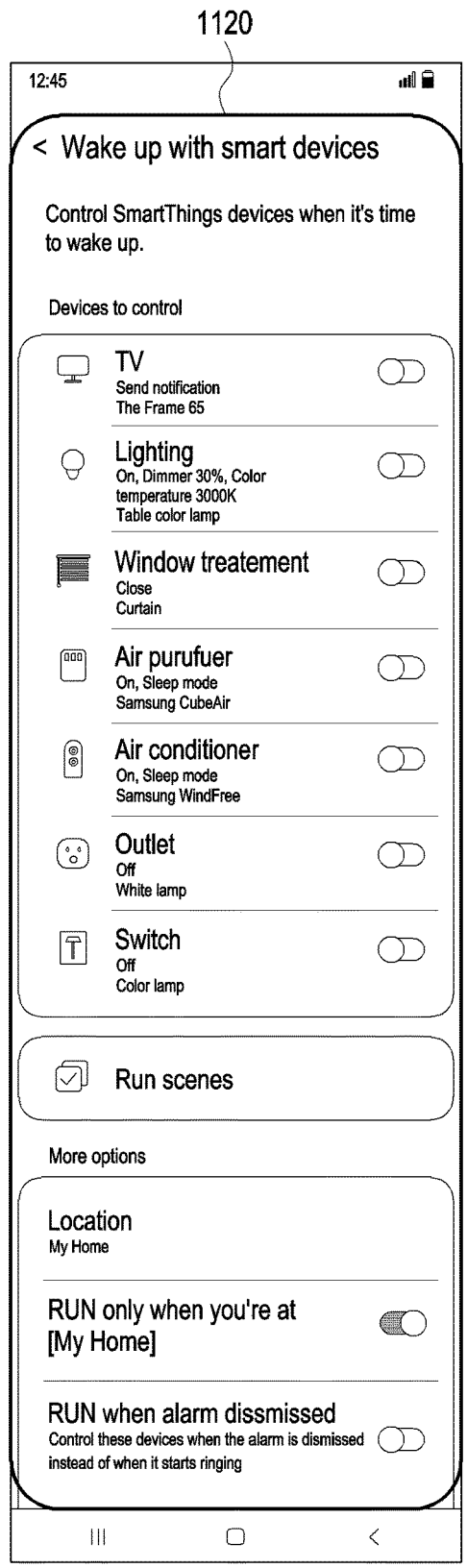

Referring to FIG. 11D, the wakeup alarm automation setting screen 1120 may be the same as the wakeup alarm automation setting screen 1014 of FIG. 10C as an example.

Figure 12A:
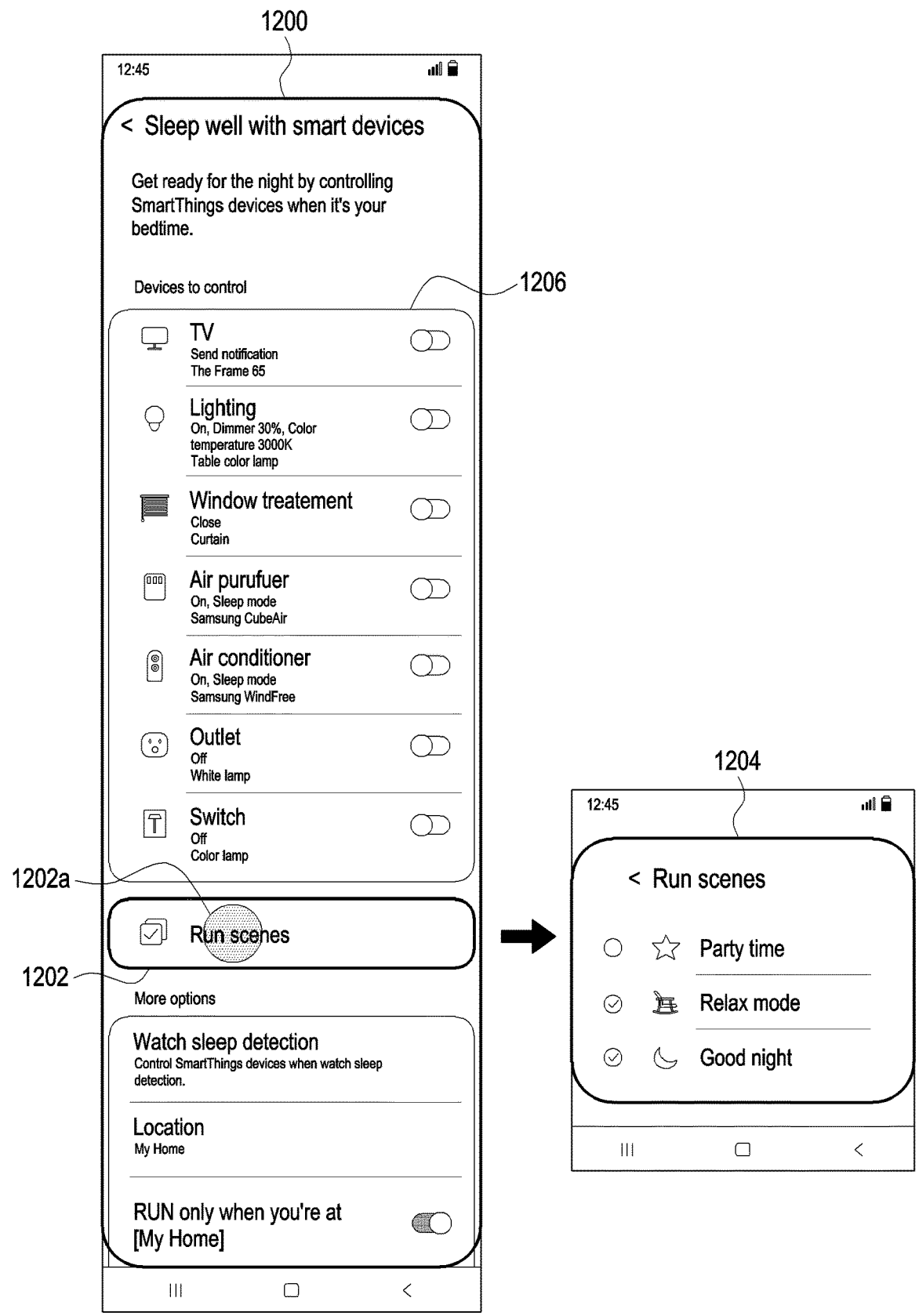
FIGS. 12A and 12B are views illustrating a sleep preparation setting according to various embodiments of the disclosure.
Figure 12B:
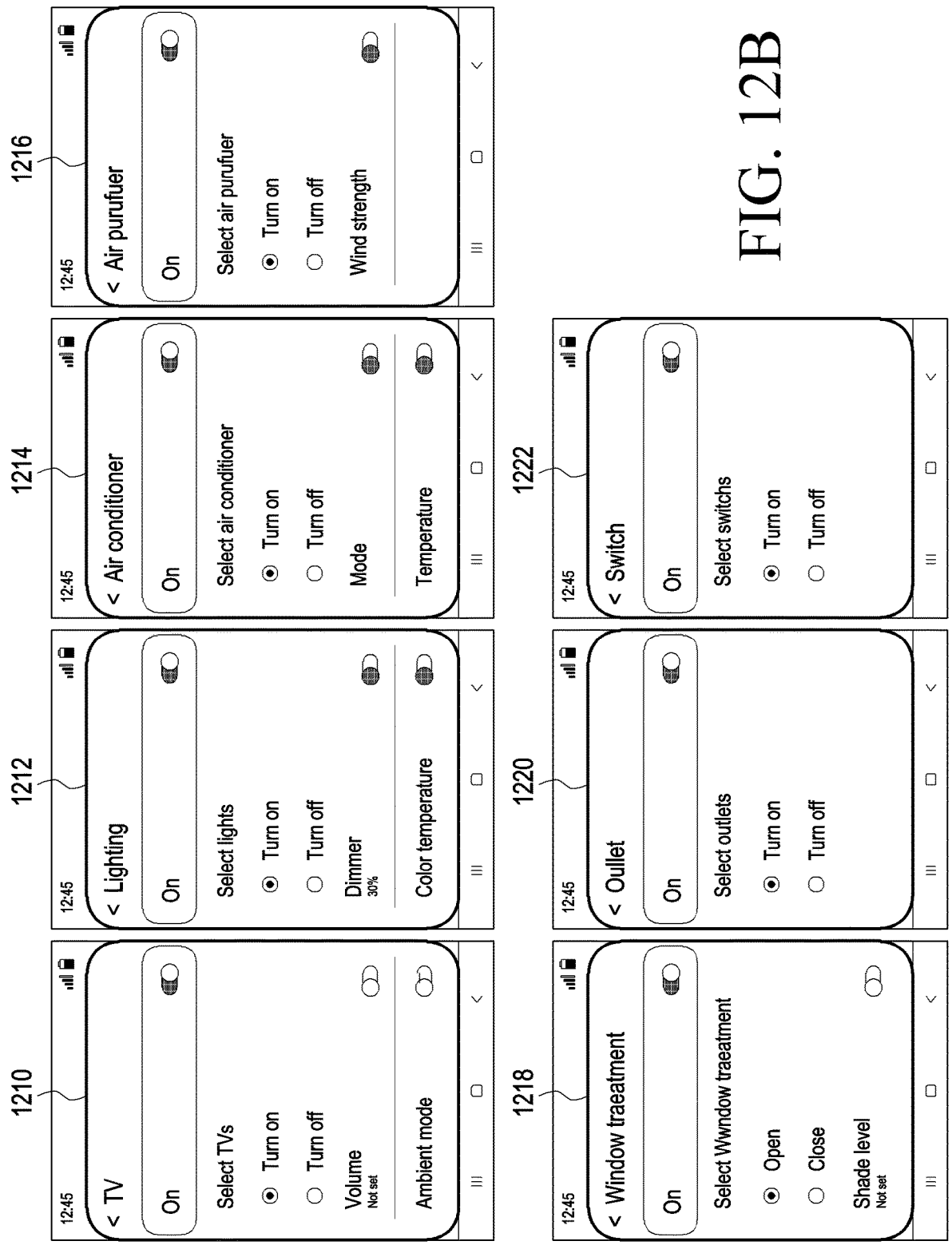

FIGS. 12A and 12B are views illustrating a sleep preparation setting according to various embodiments of the disclosure.

Referring to FIG. 12A, a sleep preparation automation setting screen 1200 (e.g., the sleep preparation automation setting screen 1002) may include a run scene menu 1202 and detailed device settings menus 1206. Upon detecting a user input 1202a on the run scene menu 1202, the electronic device (e.g., at least one of the electronic devices 422, 432, and 442) may display a mode selection screen 1204. The mode selection screen 1204 may select at least one of a party time, a relaxation mode, and a good night mode, as an example.

Referring to FIG. 12B, upon detecting a user input for one home device on the detailed device settings menus 1206, the electronic device (e.g., at least one of the electronic devices 422, 432, and 442) may display a detailed setting screen 1210, 1212, 1214, 1216, 1218, 1220, or 1222 for the sleep preparation execution operation of the corresponding home device. As an example, the detailed setting screen 1210 of the TV may set turn on/off, volume, and/or standby mode. As an example, the detailed setting screen 1212 of the lighting device may set turn on/off, dimmer, color temperature, and/or color control. As an example, the detailed setting screen 1214 of the air conditioner may set turn on/off, mode, temperature, fan speed, and/or wind free. As an example, the detailed setting screen 1216 of the air purifier may set turn on/off and/or wind strength. As an example, the detailed setting screen 1218 of the window treatment may set open/close and shade level. As an example, the detailed setting screen 1220 of the outlet may set turn on/off. As an example, the detailed setting screen 1222 of the switch may set turn on/off.

Figure 13:
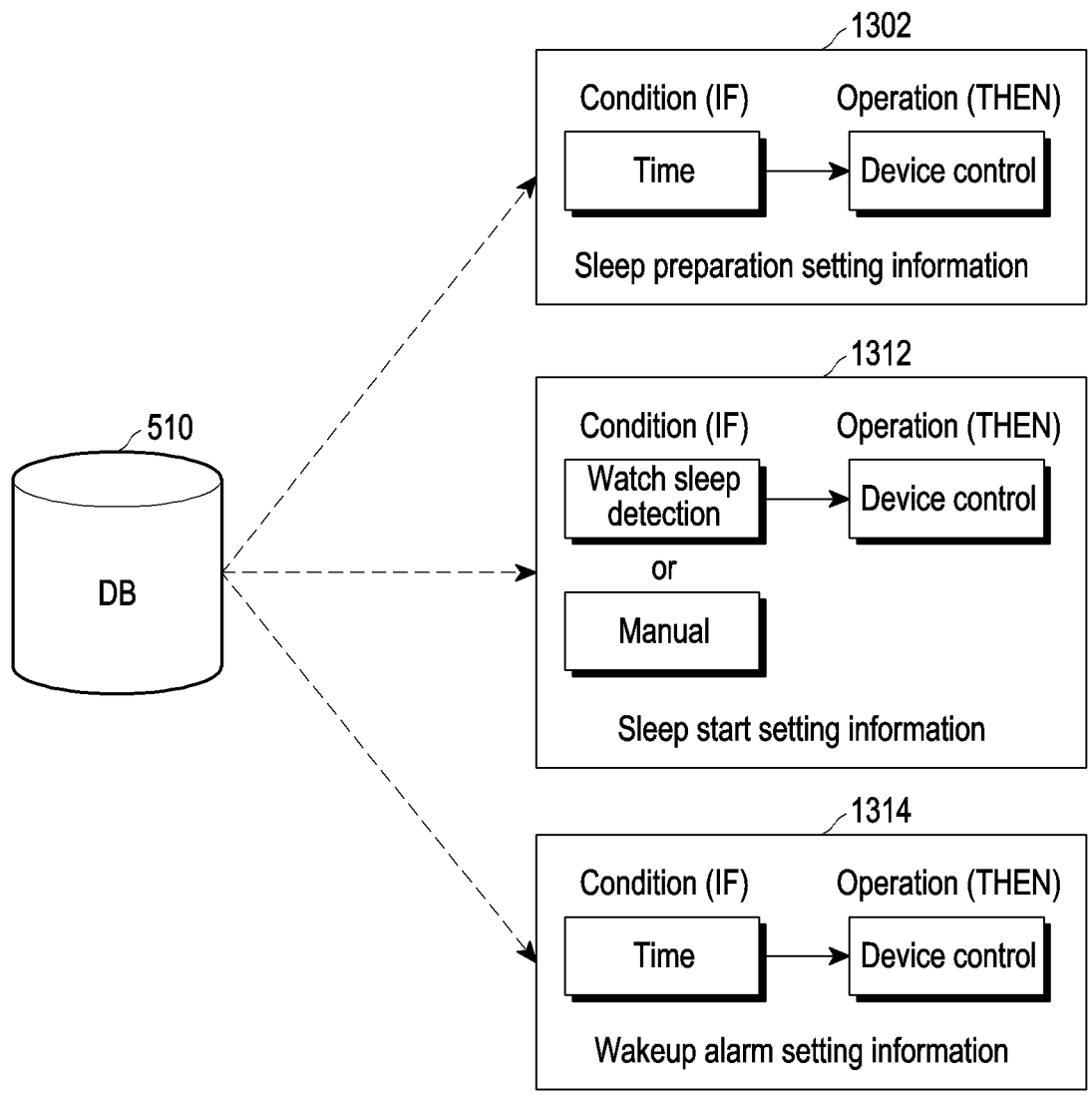
FIG. 13 is a view illustrating a type of home automation configuration information according to an embodiment of the disclosure.

FIG. 13 is a view illustrating a type of home automation configuration information according to an embodiment of the disclosure.

Referring to FIG. 13, the server 400 (e.g., home automation configuration unit 508) may store at least one of the sleep preparation setting information 1302, the sleep start setting information 1312, or the wakeup alarm setting information 1314 in the database 510.

In an embodiment of the disclosure, the sleep preparation setting information 1302 may include condition information indicating the bedtime and operation information indicating the controlled device (e.g., lighting device) and the execution operation (e.g., dimmer), through the sleep preparation automation setting screen 1002.

In an embodiment of the disclosure, the sleep start setting information 1312 may include condition information indicating watch sleep detection and/or manual and operation information indicating the controlled device (e.g., lighting device) and the execution operation (e.g., turn-off), through the sleep start automation setting screen 1012.

In an embodiment of the disclosure, the wakeup alarm setting information 1314 may set condition information indicating the wakeup time and operation information indicating the controlled device (e.g., lighting device) and execution operation (e.g., turn-off), through the wakeup alarm automation setting screen 1014.

Figure 14:
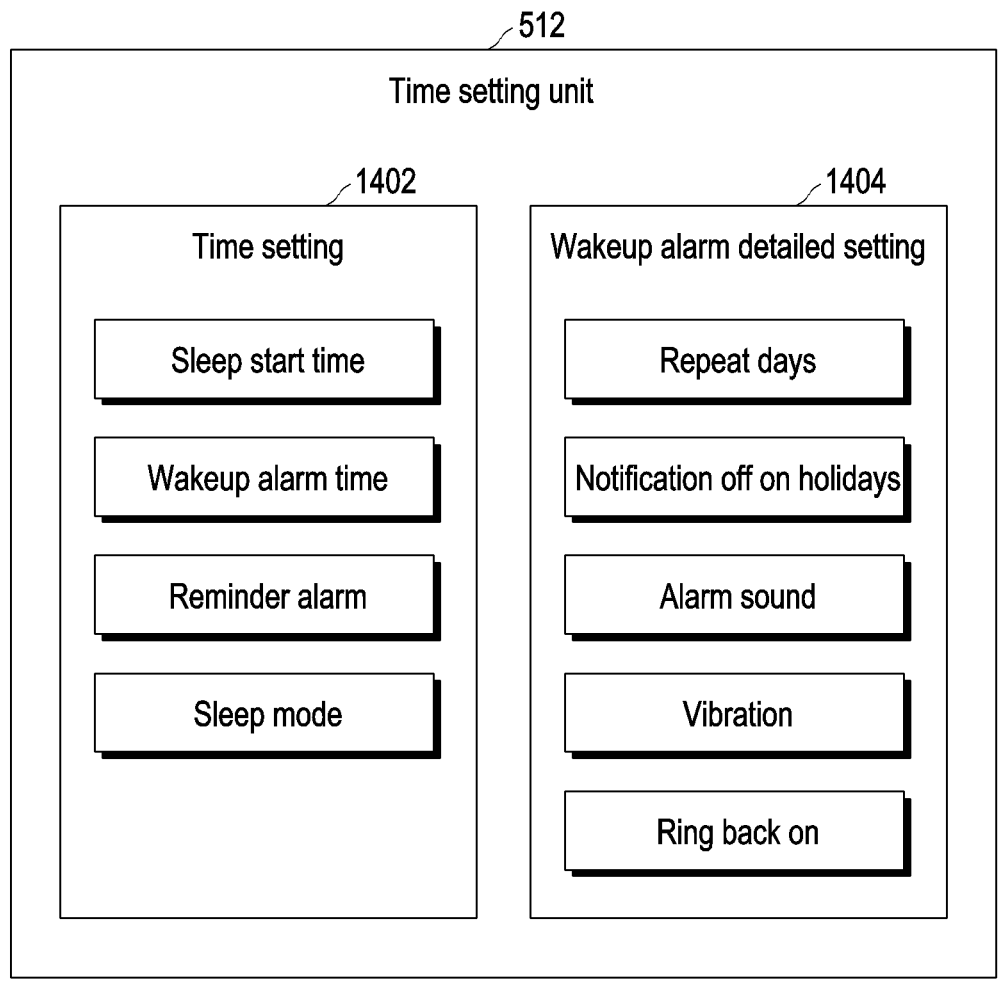
FIG. 14 is a view illustrating settings of a bedtime and a wakeup time according to an embodiment of the disclosure.

FIG. 14 is a view illustrating settings of a bedtime and a wakeup time according to an embodiment of the disclosure.

Referring to FIG. 14, the server 400 (e.g., time setting unit 512) may receive, from the user, and store time setting information 1402 and wakeup alarm detailed setting information 1404. In an embodiment of the disclosure, the time setting information 1402 may include a bedtime start time for the sleep preparation operation, a wakeup alarm time for the wakeup alarm operation, a reminder alarm, and/or a sleep mode. In an embodiment of the disclosure, the wakeup alarm detailed setting information 1404 may include repeat, notification off on holidays, alarm sound, vibration, and/or ring back on. As an example, the sleep start time of the time setting information 1402 may be stored in the sleep preparation setting information 1302. As an example, the wakeup alarm time of the time setting information 1402 may be stored in the wakeup alarm setting information 1314.

In an embodiment of the disclosure, the server 400 may determine to run the sleep preparation operation upon meeting the sleep preparation execution condition (e.g., upon reaching the sleep start time) according to the time setting information 1402. In an embodiment of the disclosure, the server 400 may determine to run the wakeup alarm operation upon meeting the wakeup alarm execution condition (e.g., upon reaching the wakeup alarm time) according to the wakeup alarm time setting information 1402.

Figure 15:
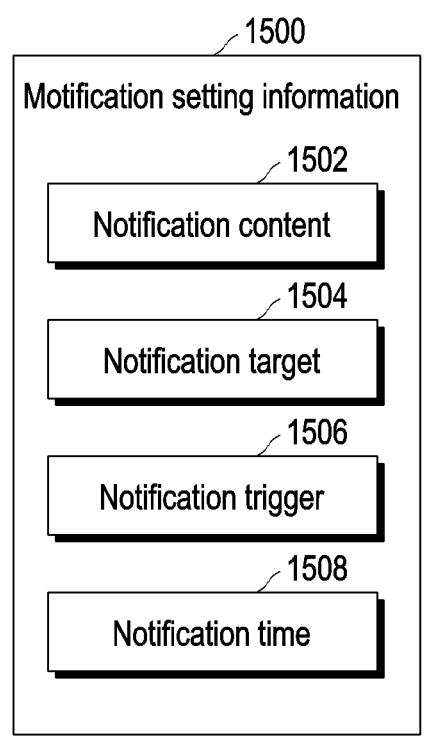
FIG. 15 is a view illustrating notification transmission according to an embodiment of the disclosure.

FIG. 15 is a view illustrating notification transmission according to an embodiment of the disclosure.

Referring to FIG. 15, the server 400 (e.g., the notification transmission unit 514) may receive notification setting information 1500 through, e.g., the electronic device (e.g., any one of the electronic devices 422, 432, and 442) or user interface 408 and store it. In an embodiment of the disclosure, the notification setting information 1500 may include notification content 1502, notification target 1504, notification trigger condition 1506, and/or notification time 1508. In an embodiment of the disclosure, the notification trigger condition 1506 may include the execution of the sleep preparation operation, the notification target 1504 may be the electronic device (e.g., the electronic device 422) having the wearable device (e.g., the wearable device 424), and the notification content 1502 may include a request for wearing or charging the wearable device.

In an embodiment of the disclosure, the server 400 (e.g., the notification transmission unit 514) may transmit a notification signal including the notification content 1502 through the communication circuit 402 to the electronic device (e.g., the electronic device 422) or wearable device (e.g., the wearable device 424) corresponding to the notification target 1504.

FIG. 16 is a view illustrating a home network control based on sleep detection according to an embodiment of the disclosure.

Referring to FIG. 16, the sleep preparation setting information 1600 for the sleep preparation operation may include condition information 1602 indicating a set sleep time and operation information 1604 indicating the controlled device (e.g., target home device) and execution operation. In an embodiment of the disclosure, the condition information 1602 may indicate 11:00 PM, and the operation information 1604 may include dimmer 30% for the lighting device in bedroom 1, dimmer 30% for the lighting device in bedroom 2, and dimmer 30% for the lighting device in bedroom 3.

In an embodiment of the disclosure, the sleep start setting information 1610 for the sleep start operation may include condition information 1612 indicating detect sleep or manual start and operation information 1614 indicating the controlled device and execution operation. In an embodiment of the disclosure, the condition information 1612 may indicate detect sleep, and the operation information 1614 may include turn-off for the lighting device in bedroom 1, turn-off for the lighting device in bedroom 2, and turn-off for the lighting device in bedroom 3.

In an embodiment of the disclosure, the wakeup alarm setting information 1620 for the wakeup alarm operation may include condition information 1622 indicating a set wakeup time and operation information 1624 indicating the controlled device and execution operation. In an embodiment of the disclosure, the condition information 1622 may indicate 7:00 AM, and the operation information 1624 may include dimmer 100% for the lighting device in bedroom 1, dimmer 100% for the lighting device in bedroom 2, and dimmer 100% for the lighting device in bedroom 3.

FIG. 17 is a view illustrating a home network control based on sleep detection according to an embodiment of the disclosure.

Referring to FIG. 17, the sleep preparation setting information 1700 for the sleep preparation operation may include condition information 1702 indicating a set sleep time and operation information 1704 indicating the controlled device (e.g., target home device) and execution operation. In an embodiment of the disclosure, the condition information 1702 may indicate 11:00 PM, and the operation information 1704 may include temperature 24° C. for the air conditioner in bedroom 1, shade level 30% for the window blind in bedroom 2, and dimmer 30% for the lighting device in bedroom 3.

In an embodiment of the disclosure, the sleep start setting information 1710 for the sleep start operation may include condition information 1712 indicating detect sleep or manual start and operation information 1714 indicating the controlled device and execution operation. In an embodiment of the disclosure, the condition information 1712 may indicate detect sleep, and the operation information 1714 may include sleep mode for the air conditioner in bedroom 1, close for the window blind in bedroom 2, and turn-off for the lighting device in bedroom 3.

In an embodiment of the disclosure, the wakeup alarm setting information 1720 for the wakeup alarm operation may include condition information 1722 indicating a set wakeup time and operation information 1724 indicating the controlled device and execution operation. In an embodiment of the disclosure, the condition information 1722 may indicate 7:00 AM, and the operation information 1724 may include preparation mode for the coffee machine in bedroom 1, open for the window blind in bedroom 2, and turn-on for the TV in bedroom 3.

FIG. 18 is a view illustrating a home network control based on sleep detection according to an embodiment of the disclosure.

Referring to FIG. 18, the sleep preparation setting information 1800 for the sleep preparation operation may include condition information 1802 indicating a set sleep time and operation information 1804 indicating the controlled device (e.g., target home device) and execution operation. In an embodiment of the disclosure, the condition information 1802 may indicate 11:00 PM, and the operation information 1804 may include temperature 24° C. for the air conditioner in bedroom 1, temperature 24° C. for the air conditioner in bedroom 2, and automatic mode for the air purifier in bedroom 3.

In an embodiment of the disclosure, the sleep start setting information 1810 for the sleep start operation may include condition information 1812 indicating detect sleep or manual start and operation information 1814 indicating the controlled device and execution operation. In an embodiment of the disclosure, the condition information 1812 may indicate detect sleep, and the operation information 1814 may include sleep mode for the air conditioner in bedroom 1, sleep mode for the air conditioner in bedroom 2, and sleep mode for the air purifier in bedroom 3.

In an embodiment of the disclosure, the wakeup alarm setting information 1820 for the wakeup alarm operation may include condition information 1822 indicating a set wakeup time and operation information 1824 indicating the controlled device and execution operation. In an embodiment of the disclosure, the condition information 1822 may indicate 7:00 AM, and the operation information 1724 may include turn-off for the air conditioner in bedroom 1, turn-off for the air conditioner in bedroom 2, and turn-off for the air conditioner in bedroom 3.

Figure 19:
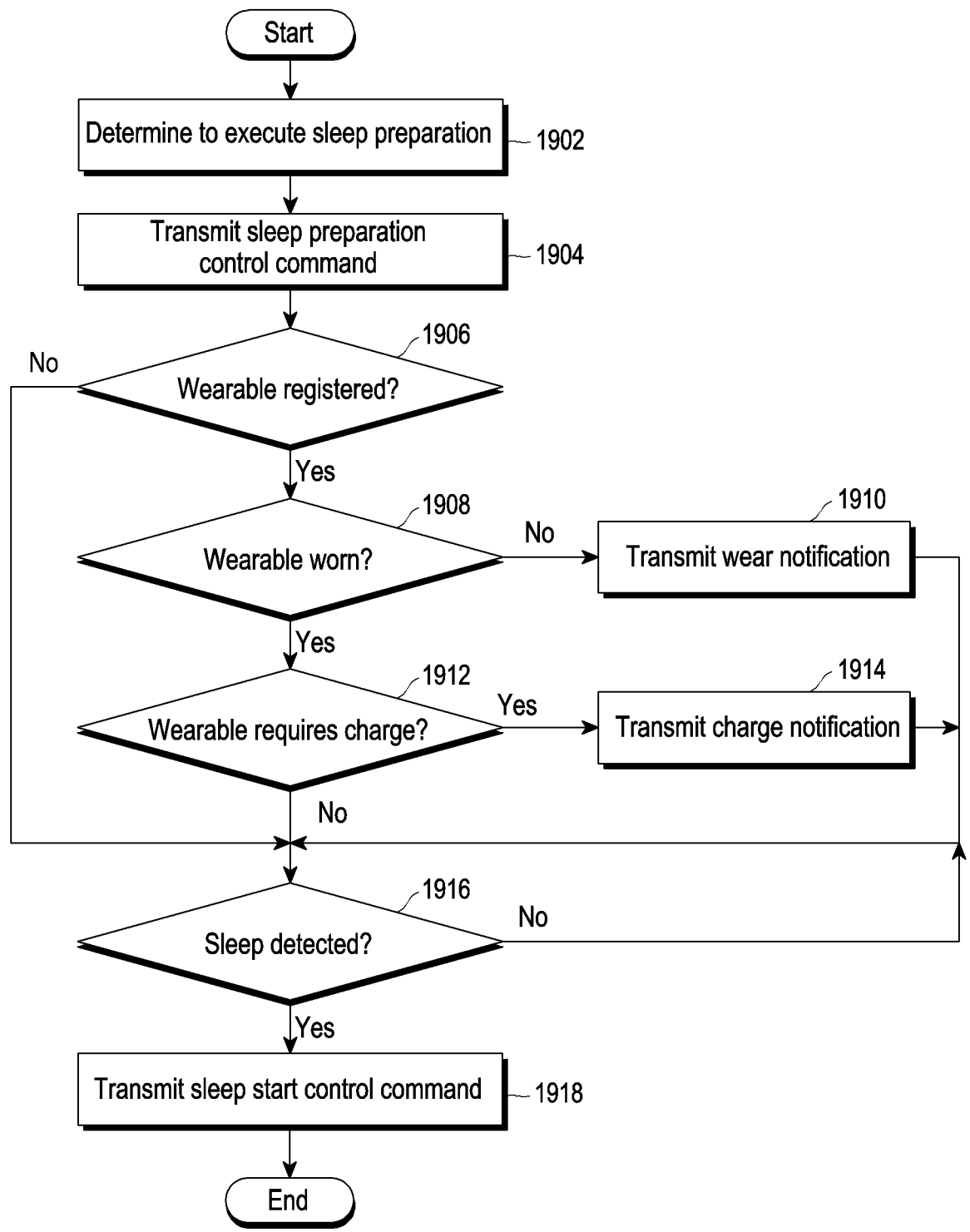
FIG. 19 is a flowchart illustrating home network control based on a user's sleep detection according to an embodiment of the disclosure.

FIG. 19 is a flowchart illustrating home network control based on a user's sleep detection according to an embodiment of the disclosure. At least one of the operations shown may be executed by the processor 404 of the server 400. In embodiments of the disclosure, at least some of the operations to be described below may be omitted, modified, or reordered.

Referring to FIG. 19, in operation 1902, the server 400 (e.g., the processor 404) may determine to execute a sleep preparation operation. In an embodiment of the disclosure, the server 400 (e.g., the processor 404) may determine to execute the sleep preparation operation according to the condition information of the sleep preparation setting information (e.g., the sleep preparation setting information 1302). As an example, the server 400 (e.g., the processor 404) may determine to execute the sleep preparation operation upon reaching the bedtime included in the condition information. In an embodiment of the disclosure, rather than directly determining whether to execute the sleep preparation operation, the server 400 (e.g., the processor 404) may receive a signal to request execution of the sleep preparation operation from the user through the Internet or from the electronic device (e.g., the electronic device 422) and determine to execute the sleep preparation operation.

In operation 1904, the server 400 (e.g., the processor 404) may transmit sleep preparation control commands to target home devices according to the sleep preparation operation. In an embodiment of the disclosure, the server 400 (e.g., the processor 404) may determine the target home devices and the content of the sleep preparation control command based on the operation information of the sleep preparation setting information (e.g., the sleep preparation setting information 1302). As an example, the server 400 (e.g., the processor 404) may transmit control commands to indicate dimmer 30% to the lighting device in bedroom 1, the lighting device in bedroom 2, and the lighting device in bedroom 3 according to the operation information 1604 of the sleep preparation setting information 1600.

In operation 1906, the server 400 (e.g., the processor 404) may determine whether the wearable device registered in the home network (e.g., the home network 450) is located in the home network 450. If the wearable device is not located, operation 1916 may proceed. In contrast, if the wearable device (e.g., the wearable device 424) is present, operation 1908 may proceed. In an embodiment of the disclosure, the server 400 (e.g., the processor 404) may identify that the wearable device 424 is included in the member information 704 of the home information 700 and identify that the wearable device 424 is located in the house corresponding to the home network 450.

In operation 1908, the server 400 (e.g., the processor 404) may determine whether the wearable device 424 is worn. If the wearable device 424 is worn, the server 400 (e.g., the processor 404) may perform operation 1912. In contrast, unless the wearable device 424 is worn, in operation 1910, the server 400 (e.g., the processor 404) may transmit a wear notification signal to the electronic device (e.g., the electronic device 422) corresponding to the wearable device 424 and perform operation 1916. In an embodiment of the disclosure, the electronic device 422 may display a wear notification message on the display module (e.g., the display module 260) in response to the wear notification signal.

Figure 21A:
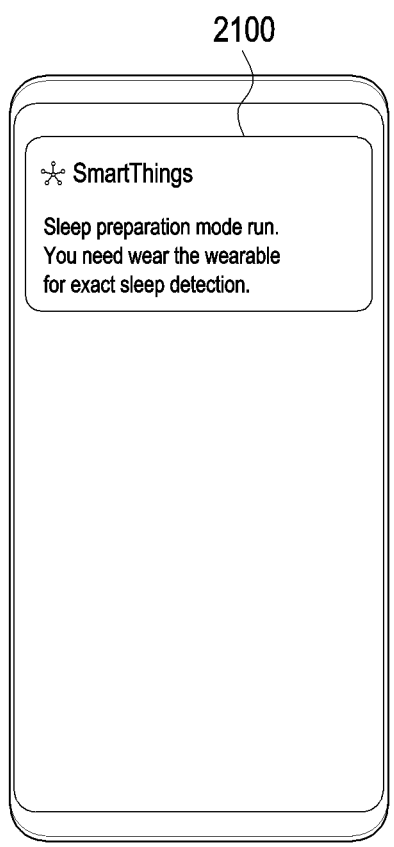
FIGS. 21A and 21B are views illustrating a wearing notification and a charging notification according to various embodiments of the disclosure.
Figure 21B:
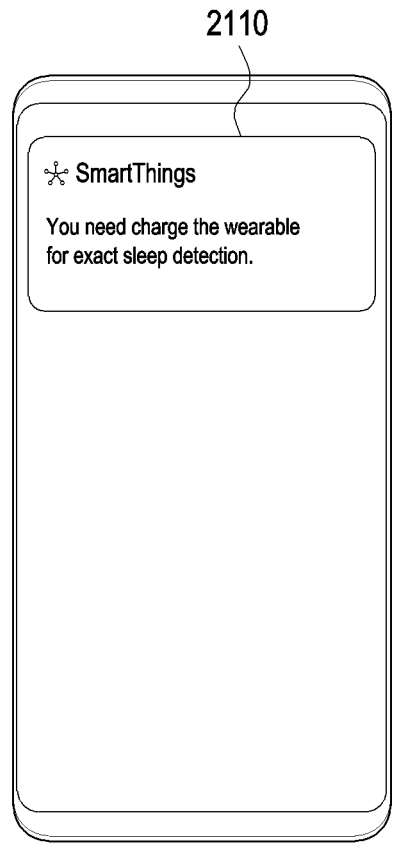

FIGS. 21A and 21B are views illustrating a wearing notification and a charging notification according to various embodiments of the disclosure.

Referring to FIGS. 21A and 21B, the wear notification message 2100 and 2110 may include "You need wear the wearable device for exact sleep detection". In an embodiment of the disclosure, the server 400 (e.g., the processor 404) may directly transmit the wear notification signal to the wearable device 424, and the wearable device 424 may output the wear notification message along with a sound or light in response to the wear notification signal.

In operation 1912, the server 400 (e.g., the processor 404) may identify the battery level of the wearable device 424 through the electronic device 422 and, as a result of the identification, determine whether to charge the wearable device 424. If the wearable device 424 need not be charged, e.g., if the battery level of the wearable device 424 is a designated threshold (e.g., 50%) or more, the server 400 (e.g., the processor 404) may perform operation 1916.

If the wearable device 424 need be charged, e.g., if the battery level of the wearable device 424 is less than the designated threshold (e.g., 50%), in operation 1914, the server 400 (e.g., the processor 404) may transmit a charge notification signal to the electronic device 422 and perform operation 1916. In an embodiment of the disclosure, the electronic device 422 may display a charge notification message on the display module (e.g., the display module 260) in response to the charge notification signal.

Referring to FIG. 21B, the wear notification message may include "You need charge the wearable device for exact sleep detection". In an embodiment of the disclosure, the server 400 (e.g., the processor 404) may directly transmit the charge notification signal to the wearable device 424, and the wearable device 424 may output the charge notification message along with a sound or light in response to the charge notification signal.

In operation 1916, the server 400 (e.g., the processor 404) may detect the user's sleep state through the electronic device 422 and/or the wearable device 424. In an embodiment of the disclosure, in response to the wearable device 424 being not present or worn, the server 400 (e.g., the processor 404) may determine whether the user sleeps based on the information related to the sleep state (e.g., the result of detection and/or use history detected through the camera, motion sensor, and/or sound sensor) provided from the electronic device 422. In an embodiment of the disclosure, in response to the wearable device 424 being worn, the server 400 (e.g., the processor 404) may determine whether the user sleeps based on the information related to the sleep state (e.g., heartrate, motion, and/or use history) provided from the electronic device 422 and/or the wearable device 424. If the user's sleep state is not detected as a result of the determination, the server 400 (e.g., the processor 404) may repeatedly or periodically perform operation 1916. In contrast, in response to the user's sleep state being detected, operation 1918 may proceed.

In operation 1918, the server 400 (e.g., the processor 404) may transmit sleep start control commands to target home devices according to the sleep start operation. In an embodiment of the disclosure, the server 400 (e.g., the processor 404) may determine the target home devices and the content of the sleep start control command based on the operation information of the sleep start setting information (e.g., the sleep start setting information 1312). As an example, the server 400 (e.g., the processor 404) may transmit control commands to indicate turn-off to the lighting device in bedroom 1, the lighting device in bedroom 2, and the lighting device in bedroom 3 according to the operation information 1614 of the sleep start setting information 1610. After transmitting the sleep start control command, the server 400 (e.g., the processor 404) may manage the target home devices in the sleep mode.

Figure 20:
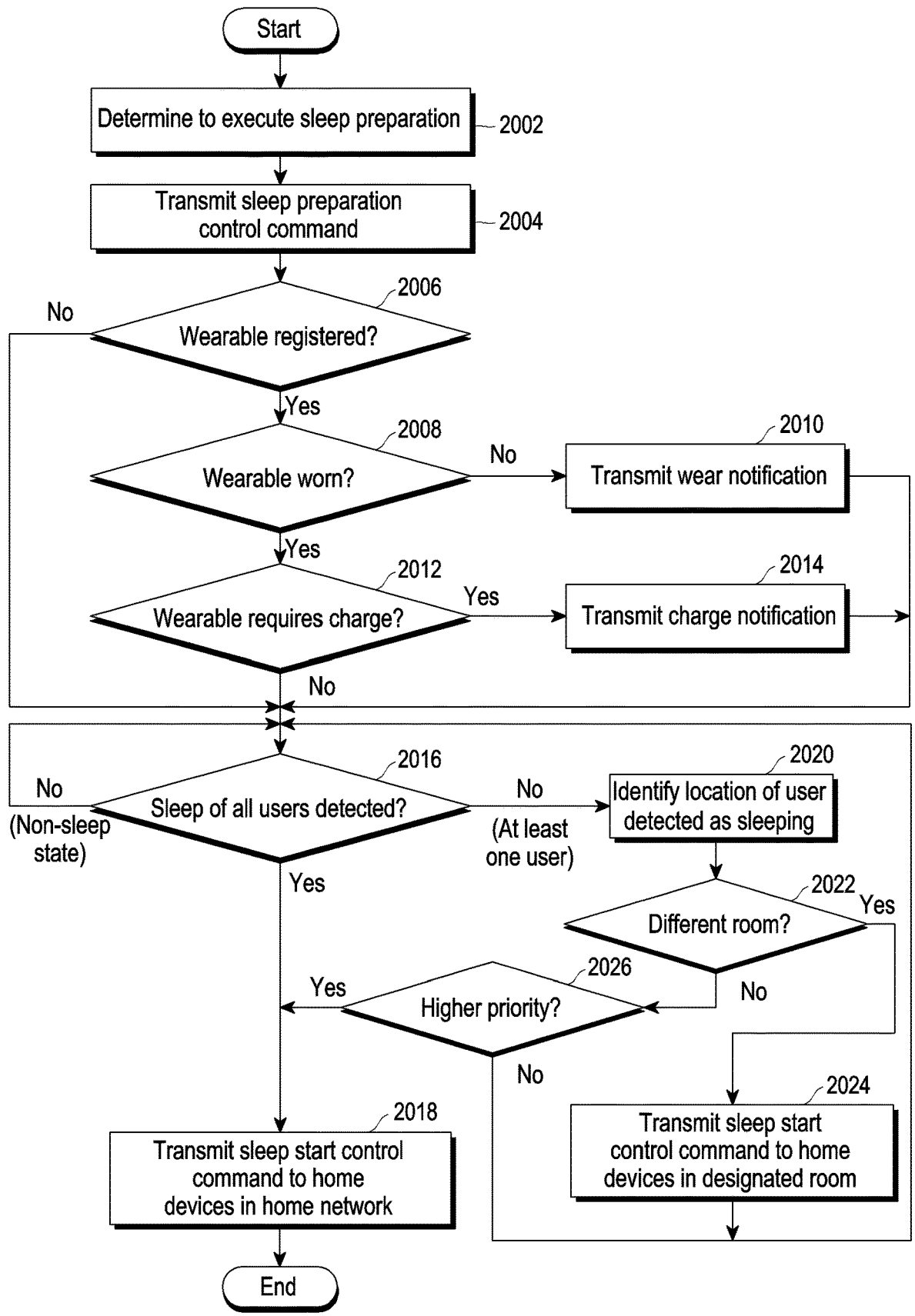
FIG. 20 is a flowchart illustrating home network control based on multiple users' sleep detection according to an embodiment of the disclosure.

FIG. 20 is a flowchart illustrating home network control based on multiple users' sleep detection according to an embodiment of the disclosure. At least one of the operations shown may be executed by the processor 404 of the server 400. In embodiments of the disclosure, at least some of the operations to be described below may be omitted, modified, or reordered.

Referring to FIG. 20, in operation 2002, the server 400 (e.g., the processor 404) may determine to execute a sleep preparation operation. In an embodiment of the disclosure, the server 400 (e.g., the processor 404) may determine to execute the sleep preparation operation according to the condition information of the sleep preparation setting information (e.g., the sleep preparation setting information 1302). As an example, the server 400 (e.g., the processor 404) may determine to execute the sleep preparation operation upon reaching the bedtime included in the condition information. In an embodiment of the disclosure, rather than directly determining whether to execute the sleep preparation operation, the server 400 (e.g., the processor 404) may receive a signal to request execution of the sleep preparation operation from the user through the Internet or from the electronic device (e.g., any one of the electronic devices 422, 432, and 442) and determine to execute the sleep preparation operation.

In operation 2004, the server 400 (e.g., the processor 404) may transmit sleep preparation control commands to target home devices according to the sleep preparation operation. In an embodiment of the disclosure, the server 400 (e.g., the processor 404) may determine the target home devices and the content of the sleep preparation control command based on the operation information of the sleep preparation setting information (e.g., the sleep preparation setting information 1302). As an example, the server 400 (e.g., the processor 404) may transmit control commands to indicate dimmer 30% to the lighting device in bedroom 1, the lighting device in bedroom 2, and the lighting device in bedroom 3 according to the operation information 1604 of the sleep preparation setting information 1600.

In operation 2006, the server 400 (e.g., the processor 404) may determine whether at least one wearable device registered in the home network (e.g., the home network 450) is located in the home network 450. If at least one wearable device is not present in the home network 450, operation 2016 may proceed. In contrast, if at least one wearable device (e.g., the wearable device 424 or 434) is present, operation 2008 may proceed. In an embodiment of the disclosure, the server 400 (e.g., the processor 404) may identify that at least one wearable device 424 or 434 is included in the member information 704 of the home information 700 and identify that the at least one wearable device 424 or 434 is located in the house corresponding to the home network 450.

In operation 2008, the server 400 (e.g., the processor 404) may determine whether at least one wearable device 424 or 434 is worn. If at least one wearable device 424 or 434 all is worn, the server 400 (e.g., the processor 404) may perform operation 2012. In contrast, unless at least one wearable device 424 or 434 is worn, in operation 2010, the server 400 (e.g., the processor 404) may transmit a wear notification signal to the electronic device (e.g., the electronic device 422 or 432) corresponding to the at least one wearable device 424 or 434 and perform operation 2016.

As an example, when the wearable device 424 is worn, and the wearable device 434 is not worn, the server 400 (e.g., the processor 404) may transmit a wear notification signal to the electronic device 432. In an embodiment of the disclosure, the electronic device 432 may display a wear notification message on the display module (e.g., the display module 260) in response to the wear notification signal. The wear notification message may include "You need wear the wearable device for exact sleep detection" as shown in FIG. 21A, as an example. In an embodiment of the disclosure, the server 400 (e.g., the processor 404) may directly transmit the wear notification signal to the wearable device 434, and the wearable device 434 may output the wear notification message along with a sound or light in response to the wear notification signal.

In operation 2012, the server 400 (e.g., the processor 404) may identify the battery level of the at least one wearable device 424 or 434 worn, through the electronic device 422 or 432 and, as a result of the determination, determine whether the wearable device 424 or 434 need be charged. If the wearable device 424 or 434 need not be charged, the server 400 (e.g., the processor 404) may perform operation 2016. In contrast, if the wearable device 424 or 434 need be charged, in operation 2014, the server 400 (e.g., the processor 404) may transmit a charge notification signal to the electronic device 422 or 432 and perform operation 2016. As an example, when the wearable device 424 has a battery level of 50% or more, and the wearable device 434 has a battery level less than 50%, the server 400 (e.g., the processor 404) may transmit a charge notification signal to the electronic device 432.

In an embodiment of the disclosure, the electronic device 432 may display a charge notification message on the display module (e.g., the display module 260) in response to the charge notification signal. The wear notification message may include "You need charge the wearable device for exact sleep detection" as shown in FIG. 21B, as an example. In an embodiment of the disclosure, the server 400 (e.g., the processor 404) may directly transmit the charge notification signal to the wearable device 434, and the wearable device 434 may output the charge notification message along with a sound or light in response to the charge notification signal.

In an embodiment of the disclosure, the server 400 (e.g., the processor 404) may perform operation 2016 after operation 2004.

In operation 2016, the server 400 (e.g., the processor 404) may detect the sleep states of a plurality of users through a plurality of electronic devices (e.g., the electronic devices 422, 432, and 442) and/or at least one wearable device 424 or 434 present in the home network 450. In an embodiment of the disclosure, when the wearable device 424 or 434 is not present in the home network 450 or not worn, the server 400 (e.g., the processor 404) may determine whether the users sleep based on the information related to the sleep state (e.g., the result of detection and/or use history detected through the camera, motion sensor, and/or sound sensor) provided from the electronic devices 422, 432, and 442. In an embodiment of the disclosure, when the wearable device 424 or 434 is worn, the server 400 (e.g., the processor 404) may determine whether the users sleep based on the information related to the sleep state (e.g., heartrate, motion, and/or use history) provided from the electronic devices 422, 432, and 442 and/or the wearable device 424 or 434.

When the sleep states of all the users are not detected as a result of the determination, e.g., when at least one user does not sleep, the server 400 (e.g., the processor 404) may perform operation 2020. In contrast, when the users' sleep states are detected, operation 2018 may proceed. In an embodiment of the disclosure, when none of the users sleep, the server 400 (e.g., the processor 404) may repeat operation 2016 until the sleep state of at least one user is detected.

In operation 2018, the server 400 (e.g., the processor 404) may transmit sleep start control commands to target home devices according to the sleep start operation. In an embodiment of the disclosure, the server 400 (e.g., the processor 404) may determine the target home devices and the content of the sleep start control command based on the operation information of the sleep start setting information (e.g., the sleep start setting information 1312). As an example, the server 400 (e.g., the processor 404) may transmit control commands to indicate turn-off to the lighting device in bedroom 1, the lighting device in bedroom 2, and the lighting device in bedroom 3 according to the operation information 1614 of the sleep start setting information 1610.

In operation 2020, the server 400 (e.g., the processor 404) may identify the locations of the plurality of users located in the home network 450. In an embodiment of the disclosure, the server 400 (e.g., the processor 404) may identify each user's location using location information (e.g., the location information 804a) received from the wearable devices (e.g., the wearable devices 424 and 434) and/or location information (e.g., the location information 802a) received from the electronic devices (e.g., the electronic devices 422, 432, and 442) corresponding to the users. In an embodiment of the disclosure, the server 400 (e.g., the processor 404) may identify which room in the home network 450 each user is located in.

In operation 2022, the server 400 (e.g., the processor 404) may identify whether at least one user detected as sleeping based on the identified location is located in a different room (e.g., another room) from the other users (non-sleeping users). If at least one sleeping user is located in the same room as the other users, the server 400 (e.g., the processor 404) may perform operation 2026.

In contrast, when at least one sleeping user is located in a different room from the other users (at least one non-sleeping user), in operation 2024, the server 400 (e.g., the processor 404) may transmit a sleep start control command to the home devices in the room where the at least one sleeping user is located. In an embodiment of the disclosure, the server 400 (e.g., the processor 404) may determine the target home devices and the content of the sleep start control command based on the operation information of the sleep start setting information (e.g., the sleep start setting information 1312). As an example, the server 400 (e.g., the processor 404) may transmit a control command to indicate turn-off to the lighting device in bedroom 1 where the sleeping user is located according to the operation information 1614 of the sleep start setting information 1610 and may transmit no control commands to turn off to the lighting devices in bedrooms 1 and 2 where the non-sleeping users are located.

As an example, in a context where users 1, 2, and 3 are preset in the home network 450, the server 400 (e.g., the processor 404) may detect that users 1 and 2 sleep, and user 3 does not sleep, through the electronic devices 422, 432, and 442 and/or the wearable devices 424 and 434 corresponding to users 1, 2, and 3. Further, the server 400 (e.g., the processor 404) may identify that users 1 and 2 are located in bedroom 1, and user 3 is located in bedroom 2 through the electronic devices 422, 432, and 442 and/or the wearable devices 424 and 434. Since no non-sleeping user is present in bedroom 1, the server 400 (e.g., the processor 404) may transmit sleep start control commands to the target home devices in bedroom 1.

In operation 2026, the server 400 (e.g., the processor 404) may determine whether at least one sleeping user has a higher priority than at least one non-sleeping user. If the at least one sleeping user has a higher priority than the at least one non-sleeping user, in operation 2018, the server 400 (e.g., the processor 404) may transmit a sleep start control command to the target home devices in the home network 450. For example, the server 400 (e.g., the processor 404) may identify that user 1 in the sleep state and user 2 in the non-sleep state are located in the same room (e.g., bedroom 1), and user 1 has a higher priority than user 2. Then, the server 400 (e.g., the processor 404) may transmit sleep start control commands to the target home devices in bedroom 1.

In contrast, unless the at least one sleeping user has a higher priority than the at least one non-sleeping user, the server 400 (e.g., the processor 404) may perform operation 2016 without performing the control according to the sleep start operation.

Figure 22:
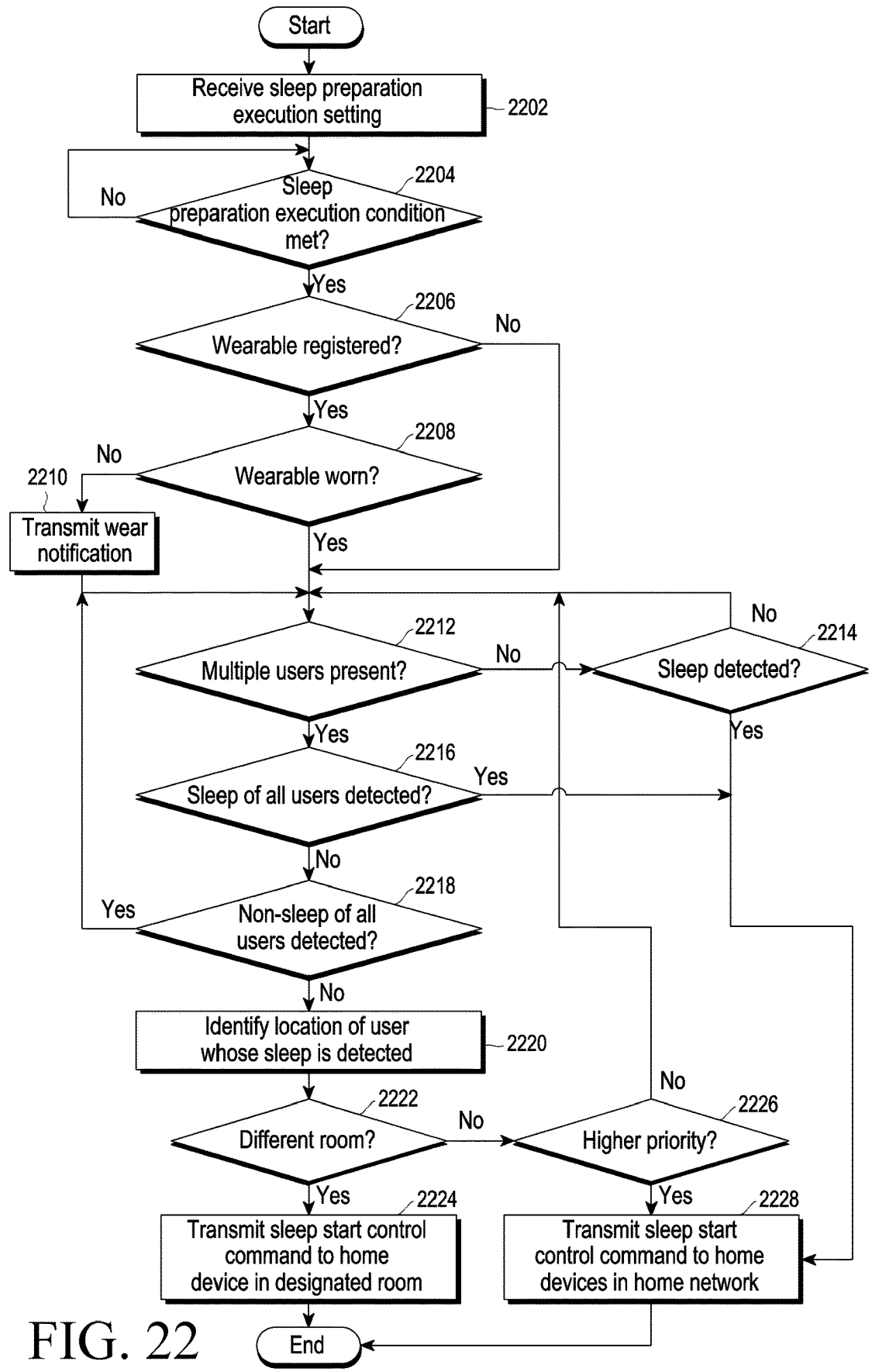
FIG. 22 is a flowchart illustrating home network control based on sleep detection of one or more users according to an embodiment of the disclosure.

FIG. 22 is a flowchart illustrating home network control based on sleep detection of one or more users according to an embodiment of the disclosure. At least one of the operations shown may be executed by the processor 404 of the server 400. In embodiments of the disclosure, at least some of the operations to be described below may be omitted, modified, or reordered.

Referring to FIG. 22, in operation 2202, the server 400 (e.g., the processor 404) may receive setting information for executing the sleep preparation operation (e.g., the sleep preparation setting information 1302). In an embodiment of the disclosure, the server 400 (e.g., the processor 404) may receive the setting information through the user interface 408 of the server 400 or the Internet, from the electronic device (e.g., any one of the electronic devices 422, 432, and 442). In operation 2204, the server 400 (e.g., the processor 404) may determine whether the sleep preparation execution condition is met based on the setting information. As an example, if the sleep time indicated by the setting information is reached, the server 400 (e.g., the processor 404) may determine that the sleep preparation execution condition is met. In response to the sleep preparation execution condition being met, the server 400 (e.g., the processor 404) may perform operation 2206.

In an embodiment of the disclosure, instead of executing operations 2202 and 2204, the server 400 (e.g., the processor 404) may receive a signal to request execution of the sleep preparation operation from the electronic device (e.g., any one of the electronic devices 422, 432, and 442) or through the Internet from the user and determine that the sleep preparation execution condition is met. In an embodiment of the disclosure, the server 400 (e.g., the processor 404) may transmit a sleep preparation control command to the target home devices according to the sleep preparation operation in response to the sleep preparation execution condition being met. In an embodiment of the disclosure, the server 400 (e.g., the processor 404) may determine the content of the sleep preparation control command and the target home devices based on the setting information. As an example, the server 400 (e.g., the processor 404) may transmit control commands to indicate dimmer 30% to the lighting device in bedroom 1, the lighting device in bedroom 2, and the lighting device in bedroom 3 according to the setting information (e.g., the operation information 1604 of the sleep preparation setting information 1600).

In operation 2206, the server 400 (e.g., the processor 404) may determine whether at least one wearable device registered in the home network (e.g., the home network 450) is located in the home network 450. If at least one wearable device is not present in the home network 450, operation 2212 may proceed. In contrast, if at least one wearable device (e.g., the wearable device 424 or 434) is present, operation 2208 may proceed. In an embodiment of the disclosure, the server 400 (e.g., the processor 404) may identify that at least one wearable device 424 or 434 is included in the member information 704 of the home information 700 and identify that the at least one wearable device 424 or 434 is located in the house corresponding to the home network 450.

In operation 2208, the server 400 (e.g., the processor 404) may determine whether at least one wearable device 424 or 434 is worn. If at least one wearable device 424 or 434 all is worn, the server 400 (e.g., the processor 404) may perform operation 2212. In contrast, unless at least one wearable device 424 or 434 is worn, in operation 2210, the server 400 (e.g., the processor 404) may transmit a wear notification signal to the electronic device (e.g., the electronic device 422 or 432) corresponding to the at least one non-worn wearable device 424 or 434 and perform operation 2212. In an embodiment of the disclosure, the server 400 (e.g., the processor 404) may identify the battery level of the wearable device 424 or 434 through the electronic device 422 or 432 and transmit a charge notification signal to the electronic device 422 or 432 corresponding to at least one wearable device 424 or 434 which needs to be charged.

In operation 2212, the server 400 (e.g., the processor 404) may determine whether a plurality of users are located in the house. In an embodiment of the disclosure, the server 400 (e.g., the processor 404) may determine whether each user is present in the house based on home information (e.g., location information 702) about the users registered in the home network 450. When a plurality of users exist, the server 400 (e.g., the processor 404) may perform operation 2216 and, when only one user exists, perform operation 2214. If no user is present in the house, the server 400 (e.g., the processor 404) may terminate the procedure.

In operation 2214, the server 400 (e.g., the processor 404) may detect the user's sleep state through the electronic device 422 and/or the wearable device 424 of the user present in the house. If the user's sleep state is not detected as a result of the determination, the server 400 (e.g., the processor 404) may return to operation 2212. In contrast, when the user's sleep state is detected, operation 2228 may proceed. In operation 2228, the server 400 (e.g., the processor 404) may transmit sleep start control commands to target home devices according to the sleep start operation. As an example, the server 400 (e.g., the processor 404) may transmit control commands to indicate turn-off to the lighting device in bedroom 1, the lighting device in bedroom 2, and the lighting device in bedroom 3 according to the operation information 1614 of the sleep start setting information 1610. After transmitting the sleep start control command, the server 400 (e.g., the processor 404) may manage the target home devices in the sleep mode.

In operation 2216, the server 400 (e.g., the processor 404) may detect the sleep states of a plurality of users through a plurality of electronic devices (e.g., the electronic devices 422, 432, and 442) and/or at least one wearable device 424 or 434 present in the home network 450. When the sleep states of all the users are not detected as a result of the determination, e.g., when at least one user does not sleep, the server 400 (e.g., the processor 404) may perform operation 2218. In contrast, when the users' sleep states are detected, operation 2228 may proceed. In an embodiment of the disclosure, unless all of the users sleep, the server 400 (e.g., the processor 404) may perform operation 2212.

In operation 2218, the server 400 (e.g., the processor 404) may determine whether the non-sleep states of all the users are detected. When the non-sleep states of all the users are detected as a result of the determination, the server 400 (e.g., the processor 404) may perform operation 2212. In contrast, when the sleep state of at least one user is detected, the server 400 (e.g., the processor 404) may perform operation 2220.

In operation 2220, the server 400 (e.g., the processor 404) may identify the locations of the plurality of users located in the home network 450. In an embodiment of the disclosure, the server 400 (e.g., the processor 404) may identify which room in the home network 450 each user is located in using location information (e.g., the location information 804a) received from the wearable devices (e.g., the wearable devices 424 and 434) and/or location information (e.g., the location information 802a) received from the electronic devices (e.g., the electronic devices 422, 432, and 442) corresponding to the users.

In operation 2222, the server 400 (e.g., the processor 404) may identify whether at least one user detected as sleeping based on the identified locations is located in a different room (e.g., another room) from the other users (non-sleeping users). If at least one sleeping user is located in the same room as the other users, the server 400 (e.g., the processor 404) may perform operation 2226.

In contrast, when at least one sleeping user is located in a different room from the other users (the non-sleeping user), in operation 2224, the server 400 (e.g., the processor 404) may transmit a sleep start control command to the home devices in the room where the at least one sleeping user is located. As an example, the server 400 (e.g., the processor 404) may transmit a control command to indicate turn-off to the lighting device in bedroom 1 where the sleeping user is located according to the operation information 1614 of the sleep start setting information 1610 and may transmit no control commands to turn off to the lighting devices in bedrooms 1 and 2 where the non-sleeping users are located.

In operation 2226, the server 400 (e.g., the processor 404) may determine whether at least one user in the sleep state has a higher priority than the other users (non-sleeping users). If the at least one sleeping user has a higher priority than the non-sleeping user, in operation 2018, the server 400 (e.g., the processor 404) may transmit a sleep start control command to the target home devices in the home network 450. For example, the server 400 (e.g., the processor 404) may identify that user 1 in the sleep state and user 2 in the non-sleep state are located in the same room (e.g., bedroom 1), and user 1 has a higher priority than user 2. Then, the server 400 (e.g., the processor 404) may transmit sleep start control commands to the target home devices in bedroom 1. After transmitting the sleep start control command, the server 400 (e.g., the processor 404) may manage the target home devices in the sleep mode.

In contrast, unless the at least one sleeping user has a higher priority than the non-sleeping user, the server 400 (e.g., the processor 404) may perform operation 2212 without performing the control according to the sleep start operation.

Figure 23:
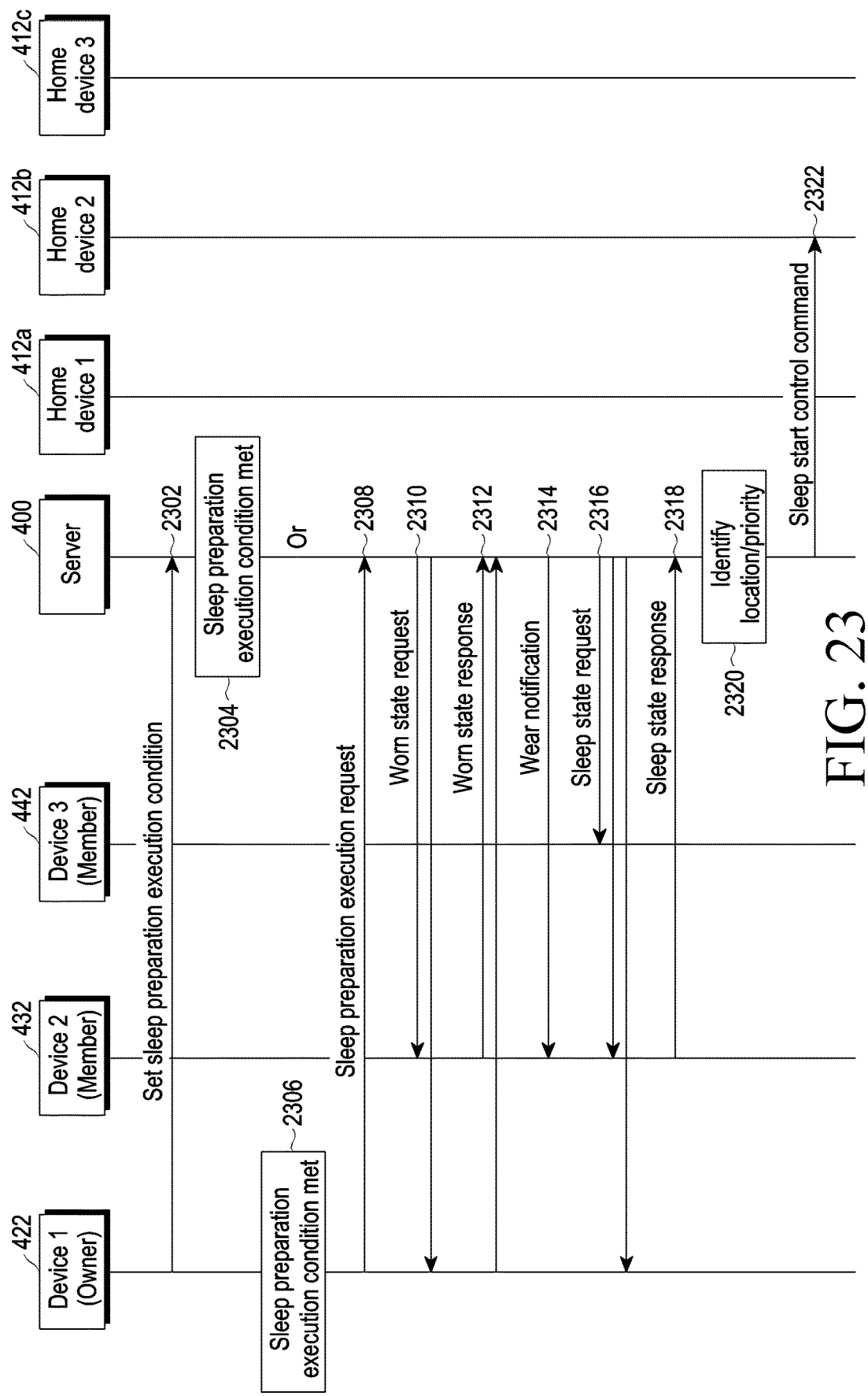
FIG. 23 is a signal flowchart illustrating a home network control based on multiple users' sleep detection according to an embodiment of the disclosure.

FIG. 23 is a signal flowchart illustrating a home network control based on multiple users' sleep detection according to an embodiment of the disclosure.

Referring to FIG. 23, in operation 2302, the server 400 (e.g., the processor 404) may receive a setting signal including the sleep preparation execution condition from electronic device 1 422. In an embodiment of the disclosure, the setting signal may include condition information (e.g., the condition information 1602) for the sleep preparation operation. In an embodiment of the disclosure, the setting signal may include operation information (e.g., the operation information 1604) for the sleep preparation operation. In operation 2304, the server 400 (e.g., the processor 404) may determine whether the sleep preparation execution condition is met based on the condition information 1602. In an embodiment of the disclosure, if the sleep time indicated by the condition information 1602 is reached, the server 400 (e.g., the processor 404) may determine that the sleep preparation execution condition is met and perform operation 2310.

In an embodiment of the disclosure, instead of operations 2302 and 2304, operations 2306 and 2308 may be executed.

In operation 2306, electronic device 1 422 may store condition information (e.g., the condition information 1602) for the sleep preparation operation and determine whether the sleep preparation execution condition is met based on the condition information 1602. In an embodiment of the disclosure, if the sleep time indicated by the condition information 1602 is reached, electronic device 1 422 may determine whether the sleep preparation execution condition is met. Upon determining that the sleep preparation execution condition is met, in operation 2308, electronic device 1 422 may transmit a sleep preparation execution request to the server 400. The server 400 (e.g., the processor 404) may perform operation 2310 in response to reception of the sleep preparation execution request.

In operation 2310, the server 400 (e.g., the processor 404) may identify that electronic devices (e.g., electronic device 1 422, electronic device 2 432, and electronic device 3 442), and wearable devices (e.g., wearable device 1 424 and wearable device 2 434) corresponding to electronic device 1 422 and electronic device 2 432 are present in the home network 450 and transmit signals to request the worn states of wearable device 1 424 and wearable device 2 434 to electronic device 1 422 and electronic device 2 432.

In operation 2312, the server 400 (e.g., the processor 404) may receive response signals indicating the worn states of wearable device 1 424 and wearable device 2 434 from electronic device 1 422 and electronic device 2 432. As an example, the response signal from electronic device 1 422 may indicate that wearable device 1 424 is worn, and the response signal from electronic device 2 432 may indicate that wearable device 2 434 is not worn. In an embodiment of the disclosure, upon failing to receive a response signal according to the worn state request from electronic device 2 432, the server 400 (e.g., the processor 404) may determine that wearable device 2 434 is not worn. In operation 2314, the server 400 (e.g., the processor 404) may transmit a wear notification signal to request to wear the wearable device to electronic device 2 432.

In an embodiment of the disclosure, the server 400 (e.g., the processor 404) may transmit the signals to request the worn state to wearable device 1 424 and wearable device 2 434 directly without passing through electronic device 1 422 and electronic device 2 432, receive a response signal for the worn state, and transmit a wear notification signal directly to wearable device 2 434.

In operation 2316, the server 400 (e.g., the processor 404) may transmit request signals for requesting the users' sleep states to electronic device 1 422, electronic device 2 432, and electronic device 3 442. In operation 2318, the server 400 (e.g., the processor 404) may receive the response signal indicating that user 2 sleeps, from electronic device 2 432. As an example, the server 400 (e.g., the processor 404) may receive a response signal indicating that users 1 and 3 do not sleep, from electronic device 1 422 and electronic device 3 442. As an embodiment of the disclosure, the server 400 (e.g., the processor 404) may determine that user 2 sleeps by not receiving the response signal indicating that user 2 does not sleep from electronic device 2 432, instead of performing operation 2316.

In an embodiment of the disclosure, the server 400 (e.g., the processor 404) may transmit request signals to request the sleep state to wearable device 1 424 and wearable device 2 434, as well as to electronic device 1 422, electronic device 2 432, and electronic device 3 442, and receive response signals for the sleep state.

In operation 2320, the server 400 (e.g., the processor 404) may identify that user 2 is present in a room different from users 1 and 3 or that user 2 is present in the same room as users 1 and 3 but has a higher priority than them. In operation 2322, the server 400 (e.g., the processor 404) may identify at least one home device (e.g., home device 2 412*b*) located in the room (e.g., bedroom 1) where among the target home devices (e.g., home device 1 412*a*, home device 2 412*b*, and home device 3 412*c*) according to the sleep start operation, user 2 is identified to be present and transmit a sleep start control command to home device 2 412b. In an embodiment of the disclosure, home device 2 412b may be turned off in response to the sleep start control command.

Figure 24:
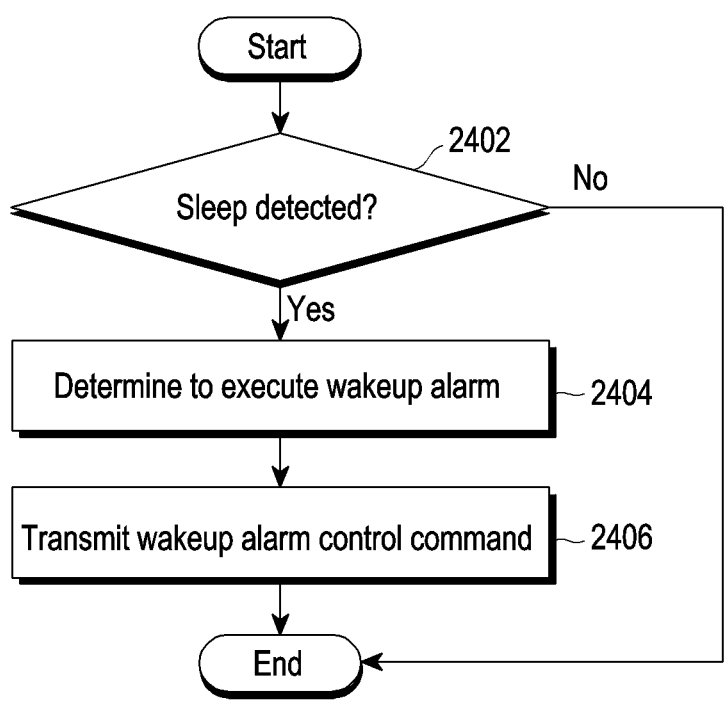
FIG. 24 is a flowchart illustrating home network control for a user's wakeup notification according to an embodiment of the disclosure.

FIG. 24 is a flowchart illustrating home network control for a user's wakeup notification according to an embodiment of the disclosure. At least one of the operations shown may be executed by the processor 404 of the server 400. In embodiments of the disclosure, at least some of the operations to be described below may be omitted, modified, or reordered.

Referring to FIG. 24, in operation 2402, the server 400 (e.g., the processor 404) may continuously determine whether the sleep state of the user present in the home network (e.g., the home network 450) is detected. In an embodiment of the disclosure, the server 400 (e.g., the processor 404) may transmit a sleep start control command to the target home devices in the home network 450 and, while managing them in the sleep mode, detect whether the user sleeps through one of the electronic devices (e.g., the electronic devices 422, 432, and 442) and/or the wearable devices (one of 424 and 434) corresponding to the user.

When the user is determined to sleep, in operation 2404, the server 400 (e.g., the processor 404) may determine to execute the wakeup alarm operation. In an embodiment of the disclosure, when the wakeup time indicated by the condition information of the wakeup alarm setting information (e.g., the wakeup alarm setting information 1314) is reached, the server 400 (e.g., the processor 404) may determine to execute the wakeup alarm operation. In an embodiment of the disclosure, upon receiving a wakeup alarm execution request from the electronic device (e.g., at least one of the electronic devices 422, 432, and 442), the server 400 (e.g., the processor 404) may determine to execute the wakeup alarm operation.

In operation 2406, the server 400 (e.g., the processor 404) may transmit a wakeup alarm control command to indicate execution of the wakeup alarm operation to home devices designated by the wakeup alarm setting information (e.g., the wakeup alarm setting information 1314). As an example, the server 400 (e.g., the processor 404) may transmit control commands to indicate dimmer 100% to the lighting device in bedroom 1, the lighting device in bedroom 2, and the lighting device in bedroom 3 according to the operation information 1624 of the wakeup alarm setting information 1620.

In an embodiment of the disclosure, when it is determined that the user is in the non-sleep state in operation 2402, the server 400 (e.g., the processor 404) may determine not to execute the wakeup alarm operation.

Figure 25:
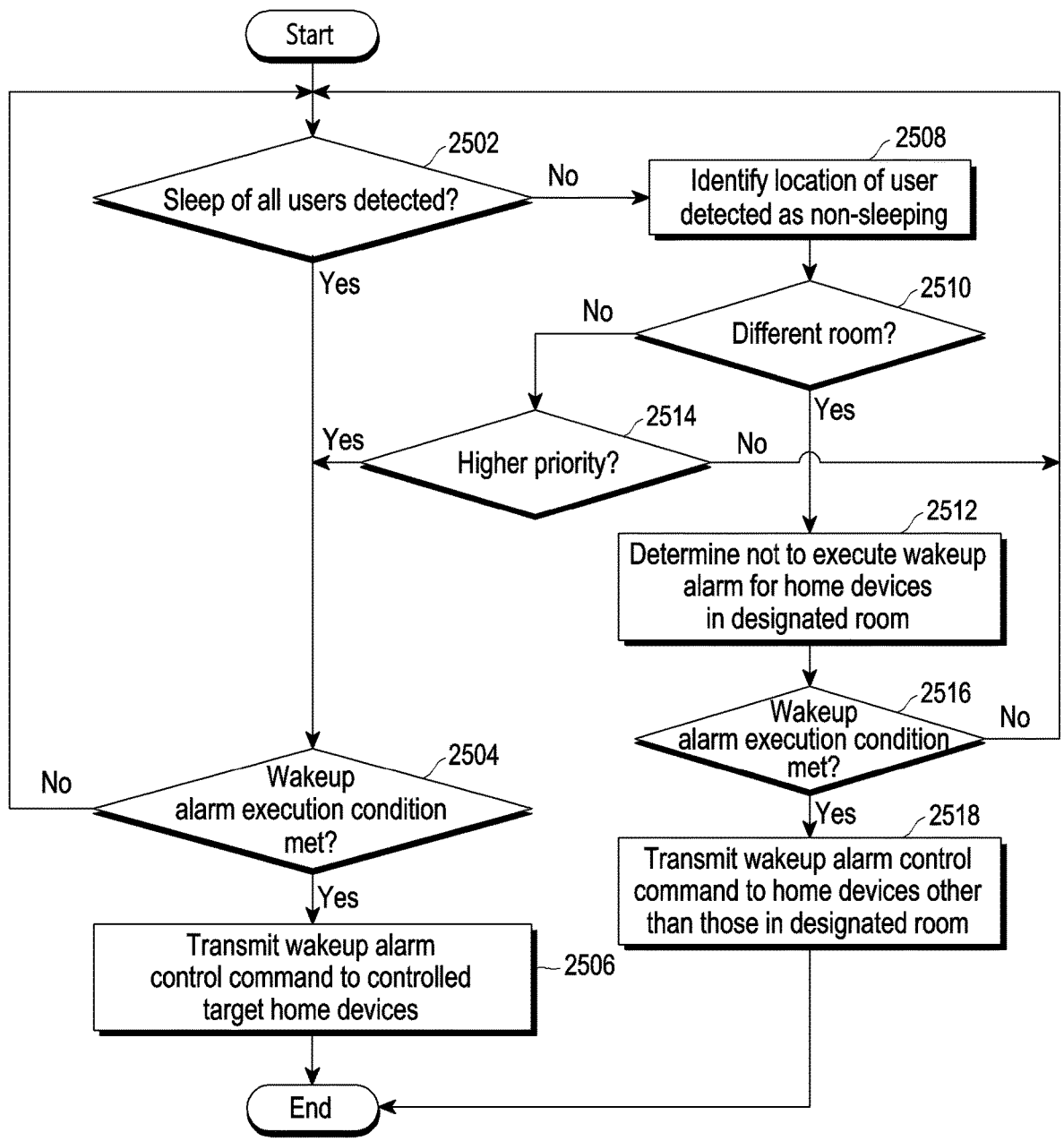
FIG. 25 is a flowchart illustrating home network control for a wakeup alarm of a plurality of users according to an embodiment of the disclosure.

FIG. 25 is a flowchart illustrating home network control for a wakeup alarm of a plurality of users according to an embodiment of the disclosure. At least one of the operations shown may be executed by the processor 404 of the server 400. In embodiments of the disclosure, at least some of the operations to be described below may be omitted, modified, or reordered.

Referring to FIG. 25, in operation 2502, the server 400 (e.g., the processor 404) may continuously determine whether the sleep states of the plurality of users present in the home network (e.g., the home network 450) are detected. In an embodiment of the disclosure, the server 400 (e.g., the processor 404) may transmit a sleep start control command to the target home devices in the home network 450 and, while managing them in the sleep mode, detect whether the users sleep through at least one of the electronic devices (e.g., the electronic devices 422, 432, and 442) and/or at least one of the wearable devices 424 and 434 corresponding to the plurality of users.

If all the users are determined to be in the sleep state, in operation 2504, the server 400 (e.g., the processor 404) may determine whether the execution condition of the wakeup alarm operation is met. In an embodiment of the disclosure, when the wakeup time indicated by the condition information of the wakeup alarm setting information (e.g., the wakeup alarm setting information 1314) is reached, the server 400 (e.g., the processor 404) may determine that the execution condition of the wakeup alarm operation is met. In an embodiment of the disclosure, upon receiving a wakeup alarm execution request from the electronic device (e.g., at least one of the electronic devices 422, 432, and 442), the server 400 (e.g., the processor 404) may determine that the execution condition of the wakeup alarm operation is met. If the execution condition of the wakeup alarm operation is not met, the server 400 (e.g., the processor 404) may return to operation 2502. In response to the execution condition of the wakeup alarm operation being met, the server 400 (e.g., the processor 404) may perform operation 2506.

In operation 2506, the server 400 (e.g., the processor 404) may transmit a wakeup alarm control command to indicate execution of the wakeup alarm operation to home devices designated by the wakeup alarm setting information (e.g., the wakeup alarm setting information 1314). As an example, the server 400 (e.g., the processor 404) may transmit control commands to indicate dimmer 100% to the lighting device in bedroom 1, the lighting device in bedroom 2, and the lighting device in bedroom 3 according to the operation information 1624 of the wakeup alarm setting information 1620.

In an embodiment of the disclosure, when the sleep state of at least one of the users is not detected or the non-sleep state is detected in operation 2502, the server 400 (e.g., the processor 404) may perform operation 2508.

In operation 2508, the server 400 (e.g., the processor 404) may identify the locations of the plurality of users located in the home network 450. In an embodiment of the disclosure, the server 400 (e.g., the processor 404) may identify which room in the home network 450 each user is located in using location information (e.g., the location information 804a) received from the wearable devices (e.g., the wearable devices 424 and 434) and/or location information (e.g., the location information 802a) received from the electronic devices (e.g., the electronic devices 422, 432, and 442) corresponding to the users.

In operation 2510, the server 400 (e.g., the processor 404) may identify whether at least one user detected as not sleeping based on the identified locations is located in a different room (e.g., another room) from the other users (sleeping users). If at least one non-sleeping user is located in the same room as the other users, the server 400 (e.g., the processor 404) may perform operation 2514.

In operation 2514, the server 400 (e.g., the processor 404) may determine whether at least one user in the non-sleep state has a higher priority than the other users (sleeping users). When at least one user in the non-sleep state has a higher priority than the user in the sleep state, in operation 2504, the server 400 (e.g., the processor 404) may determine whether the execution condition of the wakeup alarm operation is met. In response to the execution condition of the wakeup alarm operation being met, the server 400 (e.g., the processor 404) may perform operation 2506.

When at least one user in the non-sleep state is determined to be located in a different room from the other users (sleeping users) in operation 2510, in operation 2512, the server 400 (e.g., the processor 404) may determine not to execute the wakeup alarm operation for the home devices in the room where the at least one non-sleeping user is located and perform operation 2516.

In operation 2516, the server 400 (e.g., the processor 404) may determine whether the execution condition of the wakeup alarm operation is met. If the execution condition of the wakeup alarm operation is not met, the server 400 (e.g., the processor 404) may return to operation 2502. In response to the execution condition of the wakeup alarm operation being met, the server 400 (e.g., the processor 404) may perform operation 2518.

In operation 2518, the server 400 (e.g., the processor 404) may transmit a wakeup alarm control command to indicate execution of the wakeup alarm operation to home devices other than those in the designated room of operation 2512 among the home devices designated by the wakeup alarm setting information (e.g., the wakeup alarm setting information 1314). As an example, the server 400 (e.g., the processor 404) may detect that user 2 is in the non-sleep state through electronic device 2 (e.g., the electronic device 432) located in bedroom 2 in the sleep mode and transmit control commands to indicate dimmer 100% to the lighting devices in the other rooms (e.g., bedroom 1 and bedroom 3) than bedroom 2 according to the operation information 1624 of the wakeup alarm setting information 1620.

Figure 26:
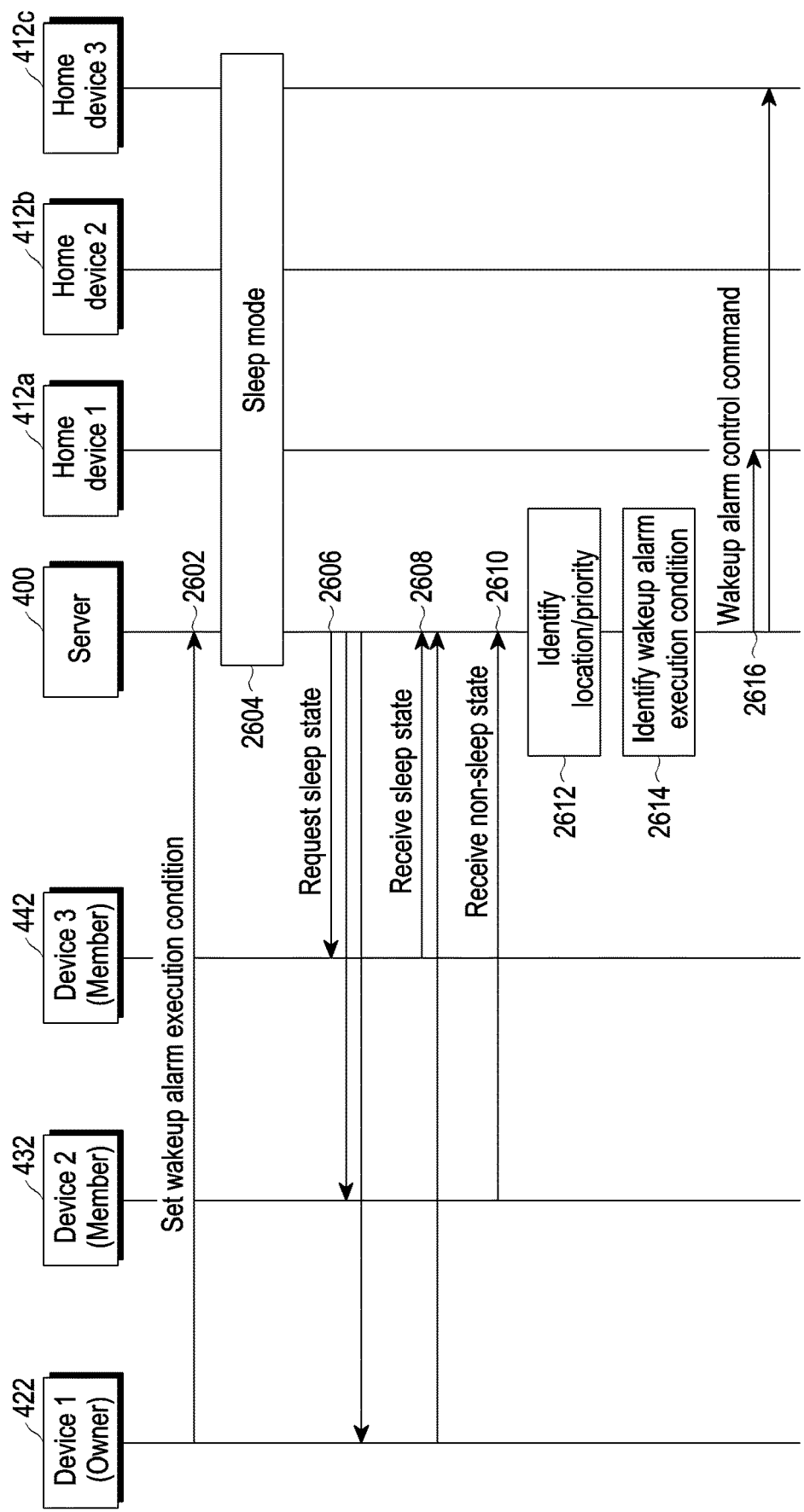
FIG. 26 is a signal flowchart illustrating a home network control for a wakeup alarm of a plurality of users according to an embodiment of the disclosure.

FIG. 26 is a signal flowchart illustrating a home network control for a wakeup alarm of a plurality of users according to an embodiment of the disclosure.

Referring to FIG. 26, in operation 2602, the server 400 (e.g., the processor 404) may receive a setting signal including the wakeup alarm execution condition from electronic device 1 422. In an embodiment of the disclosure, the setting signal may include condition information (e.g., the condition information 1622) for the wakeup alarm operation. In an embodiment of the disclosure, the setting signal may include operation information (e.g., the operation information 1624) for the sleep preparation operation. In an embodiment of the disclosure, operation 2602 may be omitted.

In operation 2604, the server 400 (e.g., the processor 404) may operate in the sleep mode. In an embodiment of the disclosure, while operating in the sleep mode, the target home devices (e.g., home device 1 412a, home device 2 412b, and home device 3 412c) of the sleep start operation may be in the turn-off state according to the sleep start control command.

In operation 2606, the server 400 (e.g., the processor 404) may transmit request signals to request the sleep states of the users (e.g., users 1, 2, and 3) to electronic device 1 422, electronic device 2 432, and electronic device 3 442 present in the home network (e.g., the home network 450). In operation 2608, the server 400 (e.g., the processor 404) may receive response signals indicating that users 1 and 3 are in the sleep state from electronic device 1 422 and electronic device 3 442. In an embodiment of the disclosure, operation 2606 may be omitted. In operation 2610, the server 400 (e.g., the processor 404) may receive the response signal indicating that user 2 does not sleep, from electronic device 2 432. At least one of operations 2608 and 2610 may be omitted. As an embodiment of the disclosure, the server 400 (e.g., the processor 404) may determine that user 2 does not sleep by not receiving the response signal indicating that user 2 sleeps from electronic device 2 432, instead of performing operation 2610.

In an embodiment of the disclosure, the server 400 (e.g., the processor 404) may transmit request signals to request the sleep state to wearable device 1 424 and wearable device 2 434, as well as to electronic device 1 422, electronic device 2 432, and electronic device 3 442, and receive response signals for the sleep state.

In operation 2612, the server 400 (e.g., the processor 404) may identify that user 2 is present in a room different from users 1 and 3 or that user 2 is present in the same room as users 1 and 3 but has a lower priority than them. In operation 2614, the server 400 (e.g., the processor 404) may identify that the wakeup alarm execution condition for the wakeup alarm operation is met (e.g., reaches the wakeup alarm time).

In operation 2616, the server 400 (e.g., the processor 404) may identify at least one home device (e.g., home device 1 412a and home device 3 412c) located in the other rooms than the room (e.g., bedroom 1) where among the target home devices (e.g., home device 1 412a, home device 2 412b, and home device 3 412c) according to the wakeup alarm operation, user 2 is identified to be present and transmit the wakeup alarm control commands to home device 1 412a and home device 3 412c. In an embodiment of the disclosure, home device 1 412a and home device 3 412c may be turned on in response to the wakeup alarm control commands.

As an example, the server 400 (e.g., the processor 404) may transmit a control command to indicate turn-on to the lighting devices in bedrooms 1 and 3 where users 1 and 3 who are sleeping are located according to the operation information 1614 of the sleep start setting information 1610 and may transmit no control commands to turn on to the lighting device in bedroom 2 where user 2 who is not sleeping is located.

According to embodiments of the disclosure, it is possible to control the home devices installed in the same space (room) as each user by automatically detecting the user's sleep state in the home network.

According to embodiments of the disclosure, it is possible to detect the sleep states of a plurality of users using a personal electronic device and/or wearable device and to control the home devices located around a sleeping user to operate in sleep mode.

According to an embodiment of the disclosure, a server 400 may comprise a communication circuit 402 and at least one processor 404. The at least one processor may be configured to identify whether a designated sleep preparation execution condition is met. The at least one processor may be configured to, in response to the sleep preparation execution condition being met, determine whether sleep states of one or more users corresponding to one or more electronic devices present in the home network 450 are detected. The at least one processor may be configured to, when the sleep states of the one or more users are detected, transmit a first control command indicating a designated first sleep start operation to a plurality of home devices present in the home network through the communication circuit.

In an embodiment of the disclosure, the at least one processor may be configured to detect that among the one or more users, a first user is in a sleep state, and a second user, not the first user, is in a non-sleep state, identify locations of the first user and the second user using at least one wearable device related to at least one of the first user and the second user and/or the one or more electronic devices, determine whether the first user is located in a room different from the second user in the home network based on the identified locations, and if the first user is located in the different room from the second user, transmit a second control command indicating a designated second sleep start operation to at least one first home device included in the room where the first user is located among the plurality of home devices.

In an embodiment of the disclosure, the at least one processor may be configured to determine that the sleep preparation execution condition is met if a designated start time is reached.

In an embodiment of the disclosure, the at least one processor may be configured to detect that among the one or more users, a first user is in a sleep state, and a second user, not the first user, is in a non-sleep state, identify locations of the first user and the second user using at least one wearable device related to at least one of the first user and the second user and/or the one or more electronic devices, determine whether the first user is located in a room different from the second user in the home network based on the identified locations, if the first user is located in the same room as the second user, determine whether the first user has a higher priority than the second user, and if the first user has the higher priority than the second user, transmit the first control command to a plurality of home devices present in the home network through the communication circuit.

In an embodiment of the disclosure, the at least one processor may be configured to identify that at least one wearable device is present in the home network if the sleep preparation execution condition is met, determine whether the at least one wearable device is worn, identify a first wearable device not worn among the at least one wearable device as a result of the determination, and transmit a wear notification to the identified first wearable device through the communication circuit.

In an embodiment of the disclosure, the at least one processor may be configured to identify a battery level of a second wearable device worn among the at least one wearable device and, upon identifying that the battery level of the second wearable device is less than a designated threshold, transmit a charge notification to the second wearable device through the communication circuit.

In an embodiment of the disclosure, the at least one processor may be configured to receive information about sleep states of the one or more users through the communication circuit from at least one wearable device and/or the one or more electronic devices corresponding to the one or more users.

In an embodiment of the disclosure, the at least one processor may be configured to determine whether the one or more users are in a sleep state while managing the plurality of home devices in a sleep mode, detect that among the one or more users, a first user is in the sleep state, and a second user, not the first user, is in a non-sleep state as a result of the determination, identify locations of the first user and the second user using at least one wearable device related to at least one of the first user and the second user and/or the one or more electronic devices, identify whether the second user is located in a room different from the first user in the home network based on the identified locations, identify whether a designated wakeup alarm execution condition is met when the second user is located in the room different from the first user, and transmit a control command indicating a designated wakeup alarm operation to at least one first home device located in a remaining room except for the room where the second user is located among the plurality of home devices if the wakeup alarm execution condition is met.

In an embodiment of the disclosure, the at least one processor may be configured to determine that the wakeup alarm execution condition is met if a designated wakeup time is reached.

In an embodiment of the disclosure, the at least one processor may be configured to, if the second user is located in the same room as the first user, determine whether the second user has a higher priority than the first user, identify whether the wakeup alarm execution condition is met if the second user has the higher priority than the first user, and transmit a control command indicating a designated wakeup alarm operation to at least one first home device located in a remaining room except for the room where the second user is located among the plurality of home devices if the wakeup alarm execution condition is met.

According to an embodiment of the disclosure, a method for operating a server 400 may comprise identifying at operation 2204 whether a designated sleep preparation execution condition is met. The method may comprise, if the sleep preparation execution condition is met, determining at operation 2216 whether sleep states of one or more users corresponding to one or more electronic devices present in a home network are detected. The method may comprise, when the sleep states of the one or more users are detected, transmitting at operation 2228 a first control command indicating a designated first sleep start operation to a plurality of home devices present in the home network through the communication circuit.

In an embodiment of the disclosure, the method may further comprise detecting at operation 2218 that among the one or more users, a first user is in a sleep state, and a second user, not the first user, is in a non-sleep state, identifying at operation 2220 locations of the first user and the second user using at least one wearable device related to at least one of the first user and the second user and/or the one or more electronic devices, determining at operation 2222 whether the first user is located in a room different from the second user in the home network based on the identified locations, and if the first user is located in the different room from the second user, transmitting at operation 2224 a second control command indicating a designated second sleep start operation to at least one first home device included in the room where the first user is located among the plurality of home devices.

In an embodiment of the disclosure, the method may further comprise determining that the sleep preparation execution condition is met if a designated start time is reached.

In an embodiment of the disclosure, the method may further comprise detecting at operation 2218 that among the one or more users, a first user is in a sleep state, and a second user, not the first user, is in a non-sleep state, identifying at operation 2220 locations of the first user and the second user using at least one wearable device related to at least one of the first user and the second user and/or the one or more electronic devices, determining at operation 2222 whether the first user is located in a room different from the second user in the home network based on the identified locations, if the first user is located in the same room as the second user, determining at operation 2226 whether the first user has a higher priority than the second user, and if the first user has the higher priority than the second user, transmitting at operation 2228 the first control command to a plurality of home devices present in the home network.

In an embodiment of the disclosure, the method may further comprise identifying at operation 2006 that at least one wearable device is present in the home network if the sleep preparation execution condition is met, determining at operation 2008 whether the at least one wearable device is worn, identifying a first wearable device not worn among the at least one wearable device as a result of the determination, and transmitting (2010) a wear notification to the identified first wearable device.

In an embodiment of the disclosure, the method may further comprise identifying a battery level of a second wearable device worn among the at least one wearable device, identifying at operation 2012 that the battery level of the second wearable device is less than a designated threshold, and transmitting at operation 2014 a charge notification to the second wearable device.

In an embodiment of the disclosure, the method may further comprise receiving information about sleep states of the one or more users from at least one wearable device and/or the one or more electronic devices corresponding to the one or more users.

In an embodiment of the disclosure, the method may further comprise determining whether the one or more users are in a sleep state while managing the plurality of home devices in a sleep mode, detecting at operation 2502 that among the one or more users, a first user is in a sleep state, and a second user, not the first user, is in a non-sleep state as a result of the determination, identifying at operation 2508 locations of the first user and the second user using at least one wearable device related to at least one of the first user and the second user and/or the one or more electronic devices, identifying at operation 2510 whether the second user is located in a room different from the first user in the home network based on the identified locations, identifying at operation 2516 whether a designated wakeup alarm execution condition is met when the second user is located in the room different from the first user, and transmitting at operation 2518 a control command indicating a designated wakeup alarm operation to at least one first home device located in a remaining room except for the room where the second user is located among the plurality of home devices if the wakeup alarm execution condition is met.

In an embodiment of the disclosure, the method may further comprise determining that the wakeup alarm execution condition is met if a designated wakeup time is reached.

In an embodiment of the disclosure, the method may further comprise, if the second user is located in the same room as the first user, determining at operation 2514 whether the second user has a higher priority than the first user, identifying at operation 2504 whether the wakeup alarm execution condition is met if the second user has the higher priority than the first user, and transmitting at operation 2506 a control command indicating a designated wakeup alarm operation to at least one first home device located in a remaining room except for the room where the second user is located among the plurality of home devices if the wakeup alarm execution condition is met.

The electronic device according to various embodiments of the disclosure may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment of the disclosure, the module may be implemented in a form of an application-specific integrated circuit (ASIC).

Various embodiments as set forth herein may be implemented as software (e.g., the program 240) including one or more instructions that are stored in a storage medium (e.g., an internal memory 236 or an external memory 238) that is readable by a machine (e.g., the electronic device 201). For example, a processor (e.g., the processor 220) of the machine (e.g., the electronic device 201) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment of the disclosure, a method according to various embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments of the disclosure, each component (e.g., a module or a program) of the above-described components may include a single entity or multiple entities. Some of the plurality of entities may be separately disposed in different components. According to various embodiments of the disclosure, one or more of the above-described components may be omitted, or one or more other components may be added. Alternatively or additionally, a plurality of components (e.g., modules or programs) may be integrated into a single component. In such a case, according to various embodiments of the disclosure, the integrated component may still perform one or more functions of each of the plurality of components in the same or similar manner as they are performed by a corresponding one of the plurality of components before the integration. According to various embodiments of the disclosure, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the scope of the disclosure as defined by the appended claims and their equivalents.

What is claimed is:

1. A server comprising:
communication circuitry;
memory storing one or more computer programs; and
one or more processors communicatively coupled to the communication circuitry and the memory,
wherein the one or more computer programs include computer-executable instructions that, when executed by the one or more processors individually or collectively, cause the server to:
identify whether a sleep preparation execution condition is met,
based on the sleep preparation execution condition being met, determine whether sleep and/or non-sleep states of one or more users corresponding to one or more electronic devices, respectively, present in a home network are detected by one or more sensors of the home network, the one or more electronic devices, or one or more wearable devices,
based on a first user among the one or more users being in a sleep state, transmit, through the communication circuitry to at least one first home device among a plurality of home devices present in the home network, a first control command indicating a designated first sleep start operation, and
based on a second user among the one or more users and different from the first user being in a non-sleep state and a designated wakeup alarm execution condition being met, transmit, through the communication circuitry to at least one home device among the plurality of home devices and located in a remaining room different from a room where the second user is located, a control command indicating a designated wakeup alarm operation.

2. The server of claim 1, wherein the one or more computer programs further include computer-executable instructions that, when executed by the one or more processors individually or collectively, cause the server to:
detect that the first user among the one or more users is in the sleep state, and that the second user among the one or more users and different from the first user is in the non-sleep state,
identify a first location of the first user and a second location of the second user using at least one wearable device related to at least one of the first user or the second user or the one or more electronic devices,
determine whether the first user is located in a room different from the second user in the home network based on the first location and the second location, and
based on the first user is being located in the room different from the second user, transmit, through the communication circuitry to the at least one first home device among the plurality of home devices and included in the room where the first user is located, a second control command indicating a designated second sleep start operation.

3. The server of claim 1, wherein the one or more computer programs further include computer-executable instructions that, when executed by the one or more processors individually or collectively, cause the server to;
determine that the sleep preparation execution condition is met based on a designated start time being reached.

4. The server of claim 1, wherein the one or more computer programs further include computer-executable instructions that, when executed by the one or more processors individually or collectively, cause the server to:
detect that the first user among the one or more users is in the sleep state and that a third user among the one or more users and different from the first user and the second user is in the non-sleep state,
identify a first location of the first user and a second location of the third user using at least one wearable device related to at least one of the first user or the third user or the one or more electronic devices,
determine whether the first user is located in a room different from the third user in the home network based on the first location and the second location,
based on the first user being located in a same room as the third user, determine whether the first user has a higher priority than the third user, and
based on the first user having the higher priority than the third user, transmit, through the communication circuitry to the at least one first home device among the plurality of home devices present in the home network, the first control command.

5. The server of claim 1, wherein the one or more computer programs further include computer-executable instructions that, when executed by the one or more processors individually or collectively, cause the server to:
identify that at least one wearable device is present in the home network based on the sleep preparation execution condition being met,
determine whether the at least one wearable device is being worn,
based on a result of determining whether the at least one wearable device is being worn, identify a first wearable device not being worn among the at least one wearable device, and
transmit, through the communication circuitry to the first wearable device not being worn, a wear notification.

6. The server of claim 5, wherein the one or more computer programs further include computer-executable instructions that, when executed by the one or more processors individually or collectively, cause the server to:
identify a battery level of a second wearable device being worn among the at least one wearable device, and
in response to identifying that the battery level of the second wearable device is less than a designated threshold, transmit, through the communication circuitry to the second wearable device, a charge notification.

7. The server of claim 1, wherein the one or more computer programs further include computer-executable instructions that, when executed by the one or more processors individually or collectively, cause the server to:
receive, through the communication circuitry from at least one wearable device or the one or more electronic devices corresponding to the one or more users, respectively, information about sleep states of the one or more users.

8. The server of claim 1, wherein the one or more computer programs further include computer-executable instructions that, when executed by the one or more processors individually or collectively, cause the server to:
determine whether the one or more users are in the sleep state while managing the plurality of home devices in a sleep mode,
based on a result of determining whether the one or more users are in the sleep state, detect that the first user among the one or more users is in the sleep state, and that the second user among the one or more users and different from the first user is in the non-sleep state,
identify a first location of the first user and a second location of the second user using at least one wearable device related to at least one of the first user or the second user or the one or more electronic devices,
identify whether the second user is located in the room different from the first user in the home network based on the first location and the second location,
based on identifying that the second user is located in the room different from the first user, identify whether the designated wakeup alarm execution condition is met, and
based on identifying that the designated wakeup alarm execution condition is met, transmit, through the communication circuitry to the at least one home device among the plurality of home devices and located in the remaining room different from the room where the second user is located, the control command indicating the designated wakeup alarm operation.

9. The server of claim 8, wherein the one or more computer programs further include computer-executable instructions that, when executed by the one or more processors individually or collectively, cause the server to;
determine that the designated wakeup alarm execution condition is met based on a designated wakeup time being reached.

10. The server of claim 8, wherein the one or more computer programs further include computer-executable instructions that, when executed by the one or more processors individually or collectively, cause the server to:
based on the second user being located in a same room as the first user, determine whether the second user has a higher priority than the first user,
identify whether the designated wakeup alarm execution condition is met based on the second user having the higher priority than the first user, and
based on identifying that the designated wakeup alarm execution condition is met, transmit, through the communication circuitry to the at least one home device among the plurality of home devices and located in the remaining room different from the room where the second user is located, the control command indicating the designated wakeup alarm operation.

11. A method performed by a server, the method comprising:
identifying, by the server, whether a sleep preparation execution condition is met;
based on identifying that the sleep preparation execution condition is met, determining, by the server, whether sleep and/or non-sleep states of one or more users corresponding to one or more electronic devices, respectively, present in a home network are detected by one or more sensors of the home network, the one or more electronic devices, or one or more wearable devices;
based on determining that a first user among the one or more users is in a sleep state, transmitting, by the server to at least one first home device among a plurality of home devices present in the home network, a first control command indicating a designated first sleep start operation; and
based on a second user among the one or more users and different from the first user being in a non-sleep state and a designated wakeup alarm execution condition being met, transmitting, by the server to at least one home device among the plurality of home devices and located in a remaining room different from a room where the second user is located, a control command indicating a designated wakeup alarm operation.

12. The method of claim 11, further comprising:
detecting, by the server, that the first user among the one or more users is in the sleep state, and that the second user among the one or more users and different from the first user is in the non-sleep state;
identifying, by the server, a first location of the first user and a second location of the second user using at least one wearable device related to at least one of the first user or the second user or the one or more electronic devices;
determining, by the server, whether the first user is located in a room different from the second user in the home network based on the first location and the second location; and
based on determining that the first user is located in the room different from the second user, transmitting, by the server to the at least one first home device among the plurality of home devices and included in the room where the first user is located, a second control command indicating a designated second sleep start operation.

13. The method of claim 11, further comprising:
determining, by the server, that the sleep preparation execution condition is met based on a designated start time being reached.

14. The method of claim 11, further comprising:
detecting, by the server, that the first user among the one or more users is in the sleep state and that a third user among the one or more users and different from the first user and the second user is in the non-sleep state;
identifying, by the server, a first location of the first user and a second location of the third user using at least one wearable device related to at least one of the first user or the third user or the one or more electronic devices;
determining, by the server, whether the first user is located in a room different from the third user in the home network based on the first location and the second location;
based on determining that the first user is located in a same room as the third user, determining, by the server, whether the first user has a higher priority than the third user; and
based on determining that the first user has the higher priority than the third user, transmitting, by the server to the at least one first home device among the plurality of home devices present in the home network, the first control command.

15. The method of claim 11, further comprising:

identifying, by the server, that at least one wearable device is present in the home network based on identifying that the sleep preparation execution condition is met;

determining, by the server, whether the at least one wearable device is being worn;

based on a result of determining whether the at least one wearable device is being worn, identifying, by the server, a first wearable device not being worn among the at least one wearable device; and transmitting, by the server to the first wearable device not being worn, a wear notification.

16. The method of claim 15, further comprising:

identifying, by the server, a battery level of a second wearable device being worn among the at least one wearable device; and in response to identifying that the battery level of the second wearable device is less than a designated threshold, transmitting, by the server to the second wearable device, a charge notification.

17. The method of claim 11, further comprising:

receiving, by the server from at least one wearable device or the one or more electronic devices corresponding to the one or more users, respectively, information about sleep states of the one or more users.

18. The method of claim 11, further comprising:

determining, by the server, whether the one or more users are in the sleep state while managing the plurality of home devices in a sleep mode;

based on a result of determining whether the one or more users are in the sleep state, detecting, by the server, that the first user among the one or more users is in the sleep state and that the second user among the one or more users and different from the first user is in the non-sleep state;

identifying, by the server, a first location of the first user and a second location of the second user using at least one wearable device related to at least one of the first user or the second user or the one or more electronic devices;

identifying, by the server, whether the second user is located in the room different from the first user in the home network based on the first location and the second location;

based on identifying that the second user is located in the room different from the first user, identifying, by the server, whether a designated wakeup alarm execution condition is met; and based on identifying that the designated wakeup alarm execution condition is met, transmitting, by the server to the at least one home device among the plurality of home devices and located in the remaining room different from the room where the second user is located, the control command indicating the designated wakeup alarm operation.

19. The method of claim 18, further comprising:

determining, by the server, that the designated wakeup alarm execution condition is met based on a designated wakeup time being reached.

20. The method of claim 18, further comprising:

based on identifying that the second user is located in a same room as the first user, determining, by the server, whether the second user has a higher priority than the first user;

based on determining that the second user has the higher priority than the first user, identifying, by the server, whether the designated wakeup alarm execution condition is met; and transmitting, by the server to the at least one home device among the plurality of home devices and located in the remaining room different from the room where the second user is located, the control command indicating the designated wakeup alarm operation.

* * * * *